US011857606B2

(12) United States Patent
Ambady et al.

(10) Patent No.: US 11,857,606 B2
(45) Date of Patent: Jan. 2, 2024

(54) THERAPEUTIC BACTERIOCINS

(71) Applicant: Bactoclear Holdings Pte. Ltd., Singapore (SG)

(72) Inventors: Anisha Ambady, Bengaluru (IN); Chemira Biddappa Appaiah, Bengaluru (IN); Deepak Balasubramanian, Chennai (IN); Vivek Daniel Paul, Bangalore (IN); R. Sanjeev Saravanan, Bengaluru (IN); Umender Kumar Sharma, Bengaluru (IN)

(73) Assignee: BACTOCLEAR HOLDINGS PTE. LTD., Singapore (SG)

( * ) Notice: Subject to any disclaimer, the term of this patent is extended or adjusted under 35 U.S.C. 154(b) by 62 days.

(21) Appl. No.: 16/954,120

(22) PCT Filed: Dec. 13, 2018

(86) PCT No.: PCT/IN2018/050837
§ 371 (c)(1),
(2) Date: Jun. 15, 2020

(87) PCT Pub. No.: WO2019/116392
PCT Pub. Date: Jun. 20, 2019

(65) Prior Publication Data
US 2021/0163546 A1  Jun. 3, 2021

(30) Foreign Application Priority Data
Dec. 14, 2017  (IN) .............................. 201741045069

(51) Int. Cl.
*A61K 38/43* (2006.01)
*A01N 63/50* (2020.01)
*A01N 63/10* (2020.01)
*C07K 14/21* (2006.01)
*C07K 14/26* (2006.01)
*C12N 9/36* (2006.01)

(52) U.S. Cl.
CPC .............. *A61K 38/43* (2013.01); *A01N 63/10* (2020.01); *A01N 63/50* (2020.01); *C07K 14/21* (2013.01); *C07K 14/26* (2013.01); *C12N 9/2462* (2013.01)

(58) Field of Classification Search
CPC ........ A61K 38/43; A01N 63/50; A01N 63/10; C07K 14/21; C07K 14/26; C12N 9/2462
See application file for complete search history.

(56) References Cited

U.S. PATENT DOCUMENTS

| 7,700,729 B2 | 4/2010 | Scholl et al. |
| 2013/0156737 A1 | 6/2013 | Mougous et al. |

FOREIGN PATENT DOCUMENTS

| WO | 2016046218 A1 | 3/2016 |

OTHER PUBLICATIONS

Bowie et al (Science, 1990, 257:1306-1310).*
Denayer et al., "Pyocin S2 (Sa) Kills Pseudomonas Aeruginosa Strains Via The Fpva Type I Ferripyoverdine Receptor", Journal of Bacteriology, vol. 189, No. 21, Nov. 2007, pp. 7663-7668.
Patzer et al., "Structural and Mechanistic Studies of Pesticin, a Bacterial Homolog of Phage Lysozymes", The Journal of Biological Chemistry, vol. 287, No. 28, Jul. 6, 2012, pp. 23381-23396.
PCT/IN2018/050837 , "International Search Report and Written Opinion", dated May 28, 2019, 9 pages.

* cited by examiner

Primary Examiner — Robert A Zeman
(74) Attorney, Agent, or Firm — SEED INTELLECTUAL PROPERTY LAW GROUP LLP

(57) ABSTRACT

The present invention provides methods and compositions to reduce growth of microbial colonies, including infections, and includes therapeutic compositions, methods for treatment of infections, and methods for identifying additional such compositions.

10 Claims, 14 Drawing Sheets

Specification includes a Sequence Listing.

SEQUENCE LISTING

<160> NUMBER OF SEQ ID NOS: 44

<210> SEQ ID NO 1
<211> LENGTH: 1689
<212> TYPE: DNA
<213> ORGANISM: Artificial Sequence
<220> FEATURE:
<223> OTHER INFORMATION: NCBI accession AF190857

<400> SEQUENCE: 1

| | |
|---|---|
| atgagtggtg gagacggtcg aggtccgggt aattcaggtc tgggacataa tggtggtcag | 60 |
| gccagtggga atgtgaacgg tacgtctggt aaaggcggcc cttcatcagg tgggggtacg | 120 |
| gatccaaaca gcgggccggg ctggggtacg acgcatacgc taacggaga tattcataac | 180 |
| tacaatccgg gggagtttgg tcacggaggg aataaacccg gtggcaatgg cggtaacagc | 240 |
| ggcaatcatc ccggtagttc tggtggcaga cagtcttcgg ccacagcgat ggccttcggt | 300 |
| ctgcctgctc tggctactcc gggctccggg gggctggctt tagccgtttc cggcgatgcg | 360 |
| ttgtcggcag ccgttgctag tgtgctggct gccctgaaag gccgtttaa gtttggtctg | 420 |
| tgggggattg cgatctacgg tgtgctgcct tctgagattg caaagatga tccgaaaatg | 480 |
| atgtcaaaaa ttatgacgtc attaccggcc gatgcggtga cggagactcc ggcaagtact | 540 |
| ttaccactgg accaggcgac ggttcgtgtc agacaacggg ttgtggatgt ggtgaaggat | 600 |
| gagcggcagc atattgcggt tgtcgcaggt cggccaatga gtgtccctgt ggtggatgcg | 660 |
| aaaccgacaa aacgtccggg ggtattcagt gtgtcgattc cgggtctccc gtctctgcag | 720 |
| gtgagcgtac cgaaaggtgt tccgacagcg aaagccccgc caaaaggcat tgttgctgaa | 780 |
| aaaggtgatt cacgtccggc tggttttaca gccggtggta actcccgtga ggccgttatt | 840 |
| cgtttcccga agagaccgg acagaagccg gtttatgtgt cggtgacaga tgttcttacc | 900 |
| ccggcacagg taaacagcg tcaggaggaa gaaaagcgtc gccagcaggc atgggacgcc | 960 |
| gctcatccgg aagaggggct gaaaagagac tatgataaag cgaaagccga gctggatgcc | 1020 |
| gaagataaaa atattgcgac cttaaacagc gcattgcat cgacagagaa ggcgctcccc | 1080 |
| ggtgcaaggg ctgctgttca ggaagccgat aaaaaggtga agaggcaga ggcgaataag | 1140 |
| gatgattttg tgacttataa ccctcctcat gaatatggct ccgggtggca ggatcaggtt | 1200 |
| cgctatcttg ataaggatat tcagaatcag aatgcgaaat taaagcggc tcaggcatct | 1260 |
| ttaaacgcaa tgaatgaatc cttatccaga gataaggctt gcacttcccg gcgatggag | 1320 |
| agccggaaac aaaaggagaa aaaagcgaag gatgcagaaa ataagttaaa tgaggaaaag | 1380 |
| aaaaaacctc gcaagggagc taaagactac ggccatgatt atcatccagc cccgaaaact | 1440 |
| gaagacataa agggactggg tgacctcaaa aaaggtacac ctaaaacacc aatgcaggga | 1500 |
| ggtggaggta ggcgtaaacg ctggattggt gataaaggcc gtaagattta tgaatgggac | 1560 |
| tcccagcacg gtgagcttga agggtatcgt gccagtgatg gcgaacacct cggggcattt | 1620 |
| gatcctaaaa cgggtaagca aattaaaggt ccggatccga aagggcgaaa cattaaaaaa | 1680 |
| tatctttaa | 1689 |

<210> SEQ ID NO 2
<211> LENGTH: 562
<212> TYPE: PRT
<213> ORGANISM: Artificial Sequence
<220> FEATURE:
<223> OTHER INFORMATION: Amino acid sequence encoded by SEQ ID NO: 1

<400> SEQUENCE: 2

```
Met Ser Gly Gly Asp Gly Arg Pro Gly Asn Ser Gly Leu Gly His
1               5                   10                  15

Asn Gly Gly Gln Ala Ser Gly Asn Val Asn Gly Thr Ser Gly Lys Gly
                20                  25                  30

Gly Pro Ser Ser Gly Gly Thr Asp Pro Asn Ser Gly Pro Gly Trp
            35                  40                  45

Gly Thr Thr His Thr Pro Asn Gly Asp Ile His Asn Tyr Asn Pro Gly
    50                  55                  60

Glu Phe Gly His Gly Gly Asn Lys Pro Gly Gly Asn Gly Gly Asn Ser
65                      70                  75                  80

Gly Asn His Pro Gly Ser Ser Gly Gly Arg Gln Ser Ser Ala Thr Ala
                85                  90                  95

Met Ala Phe Gly Leu Pro Ala Leu Ala Thr Pro Gly Ser Gly Gly Leu
                100                 105                 110

Ala Leu Ala Val Ser Gly Asp Ala Leu Ser Ala Ala Val Ala Ser Val
        115                 120                 125

Leu Ala Ala Leu Lys Gly Pro Phe Lys Phe Gly Leu Trp Gly Ile Ala
        130                 135                 140

Ile Tyr Gly Val Leu Pro Ser Glu Ile Ala Lys Asp Asp Pro Lys Met
145                 150                 155                 160

Met Ser Lys Ile Met Thr Ser Leu Pro Ala Asp Ala Val Thr Glu Thr
                165                 170                 175

Pro Ala Ser Thr Leu Pro Leu Asp Gln Ala Thr Val Arg Val Arg Gln
            180                 185                 190

Arg Val Val Asp Val Val Lys Asp Glu Arg Gln His Ile Ala Val Val
        195                 200                 205

Ala Gly Arg Pro Met Ser Val Pro Val Val Asp Ala Lys Pro Thr Lys
        210                 215                 220

Arg Pro Gly Val Phe Ser Val Ser Ile Pro Gly Leu Pro Ser Leu Gln
225                 230                 235                 240

Val Ser Val Pro Lys Gly Val Pro Thr Ala Lys Ala Pro Pro Lys Gly
                245                 250                 255

Ile Val Ala Glu Lys Gly Asp Ser Arg Pro Ala Gly Phe Thr Ala Gly
                260                 265                 270

Gly Asn Ser Arg Glu Ala Val Ile Arg Phe Pro Lys Glu Thr Gly Gln
            275                 280                 285

Lys Pro Val Tyr Val Ser Val Thr Asp Val Leu Thr Pro Ala Gln Val
        290                 295                 300

Lys Gln Arg Gln Glu Glu Glu Lys Arg Arg Gln Gln Ala Trp Asp Ala
305                 310                 315                 320

Ala His Pro Glu Glu Gly Leu Lys Arg Asp Tyr Asp Lys Ala Lys Ala
            325                 330                 335

Glu Leu Asp Ala Glu Asp Lys Asn Ile Ala Thr Leu Asn Ser Arg Ile
            340                 345                 350

Ala Ser Thr Glu Lys Ala Leu Pro Gly Ala Arg Ala Ala Val Gln Glu
            355                 360                 365

Ala Asp Lys Lys Val Lys Glu Ala Glu Ala Asn Lys Asp Asp Phe Val
        370                 375                 380

Thr Tyr Asn Pro Pro His Glu Tyr Gly Ser Gly Trp Gln Asp Gln Val
385                 390                 395                 400

Arg Tyr Leu Asp Lys Asp Ile Gln Asn Gln Asn Ala Lys Leu Lys Ala
            405                 410                 415
```

```
Ala Gln Ala Ser Leu Asn Ala Met Asn Glu Ser Leu Ser Arg Asp Lys
                420                 425                 430

Ala Cys Thr Ser Arg Ala Met Glu Ser Arg Lys Gln Lys Glu Lys Lys
            435                 440                 445

Ala Lys Asp Ala Glu Asn Lys Leu Asn Glu Glu Lys Lys Pro Arg
450                 455                 460

Lys Gly Ala Lys Asp Tyr Gly His Asp Tyr His Pro Ala Pro Lys Thr
465                 470                 475                 480

Glu Asp Ile Lys Gly Leu Gly Asp Leu Lys Lys Gly Thr Pro Lys Thr
                485                 490                 495

Pro Met Gln Gly Gly Gly Arg Arg Lys Arg Trp Ile Gly Asp Lys
                500                 505                 510

Gly Arg Lys Ile Tyr Glu Trp Asp Ser Gln His Gly Glu Leu Glu Gly
            515                 520                 525

Tyr Arg Ala Ser Asp Gly Glu His Leu Gly Ala Phe Asp Pro Lys Thr
530                 535                 540

Gly Lys Gln Ile Lys Gly Pro Asp Pro Lys Gly Arg Asn Ile Lys Lys
545                 550                 555                 560

Tyr Leu

<210> SEQ ID NO 3
<211> LENGTH: 2298
<212> TYPE: DNA
<213> ORGANISM: Artificial Sequence
<220> FEATURE:
<223> OTHER INFORMATION: NCBI accession: NC_002610.1

<400> SEQUENCE: 3
atgggtggtg gatttaacta taacggggaa ggtgctactg gcaccggatt ggatcgtgat      60
ccatatgttc gcgacagcaa tggtaatgct attggtgtta atcacgcta tcacgcggag     120 tcctatggga cgtcaagtcc agccttaggg cctaatggcg ctattcagat tactgctggg    180
gttattgctg tgcctggaga taagccccga cctgacggtg gtagtggtgg tgggaatact    240
gttaacaccg gacctgcagg acagctcctg gtgatgaata aggtcagct tggatactgg    300 gaaactcgtt ctacgggcgc gggtaacaat gagcataata cgagtgtatt tgttgctgta    360
ggtccttctg aggcagaaaa aactgcttct gcagagaagg cgttaaagga aaaacagcag    420
gcagaagcag cagcaaaaga ctttgcggct aaaactgctg ccgcatcagc cacggcggaa    480
aaagaacgcc agcaggcaat tgctgctgca actgcagcgg gtcagcatca gtcagtttct    540
gatgcccgta tagcctgaa taacgcgacg tcagatgtgt ctcgtctgaa atcagctgca    600
gacagtgcac tgcaggaggc aaaggcaaaa cggaaggctg ctattgatgc tgtacctgtt    660
gcaacccagg cggaaaataa atatcaggag ctgcagcaga gattaaagg cctgaagctg    720 aaaaatggtg agtatggtac ggataaatgg gaataattg gctctaataa ggagcatgat    780
cactggggat acaggtttta tccatccgga attaccaaag ctcaggttga tgcggcgcag    840
atcgatgctg tgaataagcg aaatcaggct accagtcttg ccagtcaggc aacagcagca    900
gaacaggaca gcctgaaagc tacagctgcc tataatgcgg cagaaacgcg ccgtcaggct    960
gctcaggcgg cgttaaattc tgctgaacag gctgctgctg ctgaacgtaa gcggcaggaa   1020
gctgaggcgg ctgcagcagc tgctgctgag aaaaaacgtc aggcagacgc agcagcaaaa   1080
gctgcagagg aagcgcgtgc ggcagcgaa aaagccaggc tgatgcagga gcgtcaggca   1140
gcagcagata agctgaaatc cacagatatt cagtctgttc gcgggatccc gtctacggct   1200
```

-continued

```
gcgcctgcag cgtcacccat ttcctgggcc gttgcatcac ttggtggtat atcgctggat      1260
agtgttactg cagggaaagc atggacgcag attgctgagg tgatggctaa actacgaggt      1320
attgccggtg cgagtcttgt tggtcccgtg gtggcaactg ctgtagggct gttttggtca      1380
cgtgatgttg gtattggcag tgatgtggtg cccggacgtg acatcagcgg gctgatgccg      1440
ggtgatgcac tgtcattacc tgatctggcc actttgatta aagctgctga cagtaaaacg      1500
ggtgtcagta tgccggttcg aggccggatt atcgtgcgtg aaggcgatta tctgagtct      1560 cagttcgttc gaacacctgt tgccggtagt gttccggttg ttcgggctgc tctggataaa      1620
gctactggtt actggggata tacgttgccg gcgatacagg gtgtgcccgg acagacaata      1680
ctggtgagtc cgtcagatgc gccgggcgtt aatggtcctc tgggacttgc tgggccggtt      1740
cctttgcctg aaactattat acataccggt gggcaaacta cggttcctca gggggggact      1800
gtgacagttt cgccggcaga agacgatatt gatttcaatg atttgattct ggtatttccg      1860
ccggagtccg gtcttaaacc gttgtatgtg atgtaccgta gccctcgtaa catgccgggg      1920
acagccagtg gtaaaggtca gaacgttgga ataactggga tggggggac cagtaccggg      1980 gatggtgctc ctgttccttc ccagattgca gataaattac gtgggaaggc tttcggtagt      2040
tttgattctt tctgtcgggc tttctggaaa gcggttgctg ctgatccgga cctcagtaag      2100
cagttttatc ctgatgatat agagcgaatg aaattagggc gagctccaac agttcgattc      2160
cgagattctg taggtaaaag ggttaaggtt gaactacacc ataaagttga aatttctaaa      2220
ggtggtgatg tctataacgt agataacctg aatgcattaa cacctaaacg tcatattgaa      2280
attcataagg ggaactga                                                    2298
```

<210> SEQ ID NO 4
<211> LENGTH: 765
<212> TYPE: PRT
<213> ORGANISM: Artificial Sequence
<220> FEATURE:
<223> OTHER INFORMATION: Amino acid sequence encoded by SEQ ID NO: 3

<400> SEQUENCE: 4

```
Met Gly Gly Gly Phe Asn Tyr Asn Gly Glu Gly Ala Thr Gly Thr Gly
1               5                   10                  15

Leu Asp Arg Asp Pro Tyr Val Arg Asp Ser Asn Gly Asn Ala Ile Gly
            20                  25                  30

Val Lys Ser Arg Tyr His Ala Glu Ser Tyr Gly Thr Ser Ser Pro Ala
        35                  40                  45

Leu Gly Pro Asn Gly Ala Ile Gln Ile Thr Ala Gly Val Ile Ala Val
    50                  55                  60

Pro Gly Asp Lys Pro Arg Pro Asp Gly Gly Ser Gly Gly Gly Asn Thr
65                  70                  75                  80

Val Asn Thr Gly Pro Ala Gly Gln Leu Leu Val Met Asn Lys Gly Gln
                85                  90                  95

Leu Gly Tyr Trp Glu Thr Arg Ser Thr Gly Ala Gly Asn Asn Glu His
            100                 105                 110

Asn Thr Ser Val Phe Val Ala Val Gly Pro Ser Glu Ala Glu Lys Thr
        115                 120                 125

Ala Ser Ala Glu Lys Ala Leu Lys Glu Lys Gln Ala Glu Ala Ala
    130                 135                 140

Ala Lys Asp Phe Ala Ala Lys Thr Ala Ala Ser Ala Thr Ala Glu
145                 150                 155                 160

Lys Glu Arg Gln Gln Ala Ile Ala Ala Ala Thr Ala Ala Gly Gln His
```

```
                165                 170                 175
Gln Ser Val Ser Asp Ala Arg Asn Ser Leu Asn Asn Ala Thr Ser Asp
            180                 185                 190

Val Ser Arg Leu Lys Ser Ala Ala Asp Ser Ala Leu Gln Glu Ala Lys
        195                 200                 205

Ala Lys Arg Lys Ala Ala Ile Asp Ala Val Pro Val Ala Thr Gln Ala
    210                 215                 220

Glu Asn Lys Tyr Gln Glu Leu Gln Gln Lys Ile Lys Gly Leu Lys Leu
225                 230                 235                 240

Lys Asn Gly Glu Tyr Gly Thr Asp Lys Trp Glu Ile Ile Gly Ser Asn
                245                 250                 255

Lys Glu His Asp His Trp Gly Tyr Arg Phe Tyr Pro Ser Gly Ile Thr
            260                 265                 270

Lys Ala Gln Val Asp Ala Ala Gln Ile Asp Ala Val Asn Lys Arg Asn
        275                 280                 285

Gln Ala Thr Ser Leu Ala Ser Gln Ala Thr Ala Glu Gln Asp Ser
    290                 295                 300

Leu Lys Ala Thr Ala Ala Tyr Asn Ala Ala Glu Thr Arg Arg Gln Ala
305                 310                 315                 320

Ala Gln Ala Ala Leu Asn Ser Ala Glu Gln Ala Ala Ala Ala Glu Arg
                325                 330                 335

Lys Arg Gln Glu Ala Glu Ala Ala Ala Ala Ala Ala Ala Glu Lys Lys
            340                 345                 350

Arg Gln Ala Asp Ala Ala Ala Lys Ala Ala Glu Glu Ala Arg Ala Ala
        355                 360                 365

Ala Glu Lys Ala Arg Leu Met Gln Glu Arg Gln Ala Ala Ala Asp Lys
    370                 375                 380

Leu Lys Ser Thr Asp Ile Gln Ser Val Arg Gly Ile Pro Ser Thr Ala
385                 390                 395                 400

Ala Pro Ala Ala Ser Pro Ile Ser Trp Ala Val Ala Ser Leu Gly Gly
                405                 410                 415

Ile Ser Leu Asp Ser Val Thr Ala Gly Lys Ala Trp Thr Gln Ile Ala
            420                 425                 430

Glu Val Met Ala Lys Leu Arg Gly Ile Ala Gly Ala Ser Leu Val Gly
        435                 440                 445

Pro Val Val Ala Thr Ala Val Gly Leu Phe Trp Ser Arg Asp Val Gly
    450                 455                 460

Ile Gly Ser Asp Val Val Pro Gly Arg Asp Ile Ser Gly Leu Met Pro
465                 470                 475                 480

Gly Asp Ala Leu Ser Leu Pro Asp Leu Ala Thr Leu Ile Lys Ala Ala
                485                 490                 495

Asp Ser Lys Thr Gly Val Ser Met Pro Val Arg Gly Arg Ile Ile Val
            500                 505                 510

Arg Glu Gly Asp Tyr Leu Glu Ser Gln Phe Val Arg Thr Pro Val Ala
        515                 520                 525

Gly Ser Val Pro Val Arg Ala Ala Leu Asp Lys Ala Thr Gly Tyr
    530                 535                 540

Trp Gly Tyr Thr Leu Pro Ala Ile Gln Gly Val Pro Gly Gln Thr Ile
545                 550                 555                 560

Leu Val Ser Pro Ser Asp Ala Pro Gly Val Asn Gly Pro Leu Gly Leu
                565                 570                 575

Ala Gly Pro Val Pro Leu Pro Glu Thr Ile Ile His Thr Gly Gly Gln
            580                 585                 590
```

Thr Thr Val Pro Gln Gly Gly Thr Val Thr Val Ser Pro Ala Glu Asp
        595                 600                 605

Asp Ile Asp Phe Asn Asp Leu Ile Leu Val Phe Pro Pro Glu Ser Gly
    610                 615                 620

Leu Lys Pro Leu Tyr Val Met Tyr Arg Ser Pro Arg Asn Met Pro Gly
625                 630                 635                 640

Thr Ala Ser Gly Lys Gly Gln Asn Val Gly Asn Asn Trp Met Gly Gly
                645                 650                 655

Thr Ser Thr Gly Asp Gly Ala Pro Val Pro Ser Gln Ile Ala Asp Lys
            660                 665                 670

Leu Arg Gly Lys Ala Phe Gly Ser Phe Asp Ser Phe Cys Arg Ala Phe
        675                 680                 685

Trp Lys Ala Val Ala Ala Asp Pro Asp Leu Ser Lys Gln Phe Tyr Pro
    690                 695                 700

Asp Asp Ile Glu Arg Met Lys Leu Gly Arg Ala Pro Thr Val Arg Phe
705                 710                 715                 720

Arg Asp Ser Val Gly Lys Arg Val Lys Val Glu Leu His His Lys Val
                725                 730                 735

Glu Ile Ser Lys Gly Gly Asp Val Tyr Asn Val Asp Asn Leu Asn Ala
            740                 745                 750

Leu Thr Pro Lys Arg His Ile Glu Ile His Lys Gly Asn
        755                 760                 765

<210> SEQ ID NO 5
<211> LENGTH: 1855
<212> TYPE: DNA
<213> ORGANISM: Artificial Sequence
<220> FEATURE:
<223> OTHER INFORMATION: NCBI accession: AY578793.1

<400> SEQUENCE: 5
atggcagata tcaaccggt tcctcttacc cccgcaccac ctggaatggt atcacttggc     60
gtcaatgaaa acggcgaaga ggagatgact gtcattggtg gagatggcag cggcacaggg    120
ttttctggga tgaagcacc tattattcct ggaagtggta gcctccaggc cgacttaggt    180
aaaaagtctc taacccgact acaggctgaa agttcagcag caattcatgc gactgcaaaa    240
tggactacag agaatcttgc aaaaacgcag gctgcgcagg ctgaaagggc caaggctgcc    300
atgctttctc agcaggcagc aaaagcaaaa caggccaaac tcacgctaca tctgaaagat    360
gtagtggatc gcgcgcttca gaacaacaaa acgcggccta ctgttattga tcttgctcat    420
cagaataacc aacaaatggc cgcaatggcc gagtttatag gccgtcaaaa ggcaattgaa    480
gaagctcgta aaaaggctga agggaagcc aaaaggggctg aagaagctta tcaggctgct    540
ttgagagcgc aggaagaaga acagcgcaag caggcagaaa ttgaacggaa attgcaggag    600
gcaaggaagc aagaggcagc ggcaaaagca aaagctgaag ctgacagaat tgcggctgag    660
aaagctgaag cagaggcaag agctaaagcg gaagctgagc gacggaaagc agaggaggct    720
cgaaaggcgc ttttttgcaaa ggctgggatt aaggacactc ctgtttatac actggagaag    780
acaaaagcag ccactacgtt gttttttaaca ccgggtgtta ggttactgaa tcgtgctcca    840
gcgatgatac agttatccgc tttggctgca gaaattaatg gcgtcttaac tactgctgct    900
agtgcagtaa tgacggctac tgctgaattc tcaggttgga ttgcctcagc gttatggcga    960
ggtgtagctg tgttgcaac agctagtact gttggtccca tggttgccgc agcatcgacg   1020
ctattctttt cacctcgcgc aggtggcgga agcgacagta aggttcctgg tagggatatc   1080

-continued

```
gagatgttgg ctgcgcaagc caggttgttc acggcgggta agctgagtat cgaacatgaa   1140
gagcgtcaac ctcccggtac gtggcttcat ctcttcggaa actgatgggc gccagtctct   1200
gatgcttgta aaaccggtt ctgatggagt accttccact gttcctgtat tggatgctgt    1260
acgtgacagt actactggcc ttgataaaat aacggtaccg gcgatgtctg gtgcgccgtc   1320
gcggaccatc ctcgtgaatc cggttccaat tggacctgct gctccgtggc ataccggcaa   1380
tagcgggcca gtgccagtaa cacctgttca caccggtaca gaggtgaagc aggctgacag   1440
tatcgtcacg acaactttgc cgattgcaga cattccgcca ctacaggact tcatctactg   1500
gcagccggat gcttctggga caggtgttga acctatttat gtaatgacta gtcaacccag   1560
gaaaggagta aagactacg gacatgatta tcatccggct ccaaaaactg aagaaattaa    1620
ggggttgggg gagttgattg agtctcggaa aaaaactcca aaacaagggg gaggtggacg   1680
acgagatcga tgggtgggag ataaaggacg aaaaatctat gagtgggatt cgcagcatgg   1740
agaacttgaa ggttacagag ctagcgacgg ctctcatctt ggagcatttg atccaaacac   1800
cggcaagcaa cttaaaggtc cggaccctaa acgtaacatc aaaaaatatc tttga        1855
```

<210> SEQ ID NO 6
<211> LENGTH: 619
<212> TYPE: PRT
<213> ORGANISM: Artificial Sequence
<220> FEATURE:
<223> OTHER INFORMATION: Amino acid sequence encoded by SEQ ID NO: 5

<400> SEQUENCE: 6

```
Met Ala Asp Asn Gln Pro Val Pro Leu Thr Pro Ala Pro Pro Gly Met
1               5                   10                  15

Val Ser Leu Gly Val Asn Glu Asn Gly Glu Glu Glu Met Thr Val Ile
            20                  25                  30

Gly Gly Asp Gly Ser Gly Thr Gly Phe Ser Gly Asn Glu Ala Pro Ile
        35                  40                  45

Ile Pro Gly Ser Gly Ser Leu Gln Ala Asp Leu Gly Lys Lys Ser Leu
    50                  55                  60

Thr Arg Leu Gln Ala Glu Ser Ser Ala Ala Ile His Ala Thr Ala Lys
65                  70                  75                  80

Trp Thr Thr Glu Asn Leu Ala Lys Thr Gln Ala Ala Gln Ala Glu Arg
                85                  90                  95

Ala Lys Ala Ala Met Leu Ser Gln Gln Ala Lys Ala Lys Gln Ala
            100                 105                 110

Lys Leu Thr Leu His Leu Lys Asp Val Val Asp Arg Ala Leu Gln Asn
        115                 120                 125

Asn Lys Thr Arg Pro Thr Val Ile Asp Leu Ala His Gln Asn Asn Gln
    130                 135                 140

Gln Met Ala Ala Met Ala Glu Phe Ile Gly Arg Gln Lys Ala Ile Glu
145                 150                 155                 160

Glu Ala Arg Lys Lys Ala Glu Arg Glu Ala Lys Arg Ala Glu Glu Ala
                165                 170                 175

Tyr Gln Ala Ala Leu Arg Ala Gln Glu Glu Gln Arg Lys Gln Ala
            180                 185                 190

Glu Ile Glu Arg Lys Leu Gln Glu Ala Arg Lys Gln Glu Ala Ala Ala
        195                 200                 205

Lys Ala Lys Ala Glu Ala Asp Arg Ile Ala Ala Glu Lys Ala Glu Ala
    210                 215                 220
```

Glu Ala Arg Ala Lys Ala Glu Ala Glu Arg Arg Lys Ala Glu Ala
225                 230                 235                 240

Arg Lys Ala Leu Phe Ala Lys Ala Gly Ile Lys Asp Thr Pro Val Tyr
            245                 250                 255

Thr Leu Glu Lys Thr Lys Ala Thr Thr Leu Phe Leu Thr Pro Gly
        260                 265                 270

Val Arg Leu Leu Asn Arg Ala Pro Ala Met Ile Gln Leu Ser Ala Leu
        275                 280                 285

Ala Ala Glu Ile Asn Gly Val Leu Thr Thr Ala Ala Ser Ala Val Met
    290                 295                 300

Thr Ala Thr Ala Glu Phe Ser Gly Trp Ile Ala Ser Ala Leu Trp Arg
305                 310                 315                 320

Gly Val Ala Gly Val Ala Thr Ala Ser Thr Val Gly Pro Met Val Ala
            325                 330                 335

Ala Ala Ser Thr Leu Phe Phe Ser Pro Arg Ala Gly Gly Ser Asp
        340                 345                 350

Ser Lys Val Pro Gly Arg Asp Ile Glu Met Leu Ala Ala Gln Ala Arg
        355                 360                 365

Leu Phe Thr Ala Gly Lys Leu Ser Ile Glu Pro Gly Met Lys Ser Val
    370                 375                 380

Asn Leu Pro Val Arg Gly Phe Ile Ser Ser Glu Thr Asp Gly Arg Gln
385                 390                 395                 400

Ser Leu Met Leu Val Lys Thr Gly Ser Asp Gly Val Pro Ser Thr Val
            405                 410                 415

Pro Val Leu Asp Ala Val Arg Asp Ser Thr Thr Gly Leu Asp Lys Ile
        420                 425                 430

Thr Val Pro Ala Met Ser Gly Ala Pro Ser Arg Thr Ile Leu Val Asn
    435                 440                 445

Pro Val Pro Ile Gly Pro Ala Ala Pro Trp His Thr Gly Asn Ser Gly
    450                 455                 460

Pro Val Pro Val Thr Pro Val His Thr Gly Thr Glu Val Lys Gln Ala
465                 470                 475                 480

Asp Ser Ile Val Thr Thr Thr Leu Pro Ile Ala Asp Ile Pro Pro Leu
            485                 490                 495

Gln Asp Phe Ile Tyr Trp Gln Pro Asp Ala Ser Gly Thr Gly Val Glu
        500                 505                 510

Pro Ile Tyr Val Met Thr Ser Gln Pro Arg Lys Gly Val Lys Asp Tyr
    515                 520                 525

Gly His Asp Tyr His Pro Ala Pro Lys Thr Glu Glu Ile Lys Gly Leu
    530                 535                 540

Gly Glu Leu Ile Glu Ser Arg Lys Lys Thr Pro Lys Gln Gly Gly Gly
545                 550                 555                 560

Gly Arg Arg Asp Arg Trp Val Gly Asp Lys Gly Lys Ile Tyr Glu
            565                 570                 575

Trp Asp Ser Gln His Gly Glu Leu Glu Gly Tyr Arg Ala Ser Asp Gly
        580                 585                 590

Ser His Leu Gly Ala Phe Asp Pro Asn Thr Gly Lys Gln Leu Lys Gly
    595                 600                 605

Pro Asp Pro Lys Arg Asn Ile Lys Lys Tyr Leu
    610                 615

<210> SEQ ID NO 7
<211> LENGTH: 2151
<212> TYPE: DNA

<213> ORGANISM: Artificial Sequence
<220> FEATURE:
<223> OTHER INFORMATION: NCBI accession: AY578792

<400> SEQUENCE: 7

```
atgagtgata tcacatataa tcctgaggac tataacaatg gtataccacc tgagccgggt      60
ctggtgtgga agccgggagg ctcattcccc aatggcagtt acgttcccgg ctcatggggc     120
tggccaacgc gcggatacga tgttcctccg ctgccgggtg ataccgaaat gctgacggtc     180
accccaaaag gaacgccggc tgataccggg cctaaaagac ctgatatcaa agagtggtat     240
gttccgggtg aaaaacccat cgacccgtca acaggtaatg gatgggtgcc tgatgtggac     300
ggctacgccg aatcgctgcc tgccggtata ccggctgtgg tacaggctgc aatcagtaag     360
gtgaaaggtg cgccactgaa aggcggcatg tccgccgtgg atatctggaa actgaaaccc     420
gcaacggagt acccggggag atttaacagc accgacccgg cattcagctg gtttccggtt     480
cgggcgctga ctgacactga tatatctgcg atgcccgttg ccctgagac tgttccggtg     540
catacccgta tccttgataa tgttcatgat ggtgtacagt ttgtttctgc ggtgtttgcg     600
ggtagcatgc agtacaatct gccggtggtg aaagcgcagg ccactgccgg cagtgattat     660
tacactatcg gacgtctgcc gggcatcatg agtgctttca cattctcttt ctacacaaaa     720
ggaacaccac aggactcccg tttcttccgg gatacagtga agccggggg agatttacgc     780
gaagcaggct tcactgtggg ggccaatacc agcgatttta tcatctggtt ccgcaggggg     840
agcggactgg agccgctgta tttttccatg accatgaata tgccggctgg gccgctgcag     900
cgtcgccagg aagccgaaaa caaggccaga gcagaagctg acaggctccg ggcagaggcg     960
gaggcaaaaa ttcgcgctga agcagaggcc cgggcgaaag cagaagcaga acgcaaagcc    1020
ctgttcgcta aggccggtat tcaggataca ccggtttaca cgccggagat ggtgaaggcg    1080
gcaaatgcgg cgctgtctgc cggaggctca atggcgctca gccgggcccc ggggatgata    1140
cagcactctg ctgcaggcgt ggggacgcta cccttcaaca gtagtctggc gggatgggaa    1200
gccggcgcgc tctggcgcgg tgtcgacgtg cttgccagga tcgcgccggt cgcgtccgcc    1260
gtggccacgg ttgccacagt gctcaccctt gtcagggctg cactggatat ccctgcagcc    1320
ggcgagggca gtgacagggt tcccggacgc aacattgaca tgcttgccgc ccaggccagc    1380
ctgtacacgg ccatgaagac gaacattcag ccggggatga agaccgttga cctgccagtc    1440
agggggatata tctcgtatga cggcaacggc cggcagtcgg tcaacttggt caggacgggg    1500
acgggcgggg tttcggccac ggtgccggtg ctgagtgccg tgcgtgacaa aaccaccggc    1560
ctggataaaa tcacggtacc ggccgtggcg ggcgccccgt cgcggaccat cctgattaac    1620
cctgtaccgg tcggtcctgc gacaccatcg cataccggca gcagtacgcc ggttccggtg    1680
acgccggtgc acactggtac cgatgttaag caggcggaca gcatcgtcac cacaacgttg    1740
ccggcggcag atattcctgc gctgcaggac ttcatctact ggcagccgga tgcaaccggg    1800
acgggcgtgg aacccatcta tgtcatgctg agtgatccgt ggattcgggg gaaatatacc    1860
cgcaggcagc tccagaagaa gtacaagcat gctatcgatt ttggtatcac agatacgaag    1920
ataaatggtg aaacacttac taagttccgg gatgcaattg aagcacatct ttcagataag    1980
gataccttg aaaaaggaac atatcggcgt gataagggat cgaaggttta tttcaatcct    2040
aaaacaatga atgctgttat tattcaggct aatggtgact ttctgtctgg atggaaaatt    2100
aatcctgcgg cagataatgg tagaatttat ttagaaacgg gtgatttatg a             2151
```

```
<210> SEQ ID NO 8
<211> LENGTH: 716
<212> TYPE: PRT
<213> ORGANISM: Artificial Sequence
<220> FEATURE:
<223> OTHER INFORMATION: Amino acid sequence encoded by SEQ ID NO: 7

<400> SEQUENCE: 8

Met Ser Asp Ile Thr Tyr Asn Pro Glu Asp Tyr Asn Gly Ile Pro
1               5                   10                  15

Pro Glu Pro Gly Leu Val Trp Lys Pro Gly Ser Phe Pro Asn Gly
                20                  25                  30

Ser Tyr Val Pro Gly Ser Trp Gly Trp Pro Thr Arg Gly Tyr Asp Val
            35                  40                  45

Pro Pro Leu Pro Gly Asp Thr Glu Met Leu Thr Val Thr Pro Lys Gly
50                  55                      60

Thr Pro Ala Asp Thr Trp Pro Lys Arg Pro Asp Ile Lys Glu Trp Tyr
65                  70                  75                  80

Val Pro Gly Glu Lys Pro Phe Asp Pro Ser Thr Gly Asn Gly Trp Val
                85                  90                  95

Pro Asp Val Asp Gly Tyr Ala Glu Ser Leu Pro Ala Gly Ile Pro Ala
                100                 105                 110

Val Val Gln Ala Ala Ile Ser Lys Val Lys Gly Ala Pro Leu Lys Gly
            115                 120                 125

Gly Met Ser Ala Val Asp Ile Trp Lys Leu Lys Pro Ala Thr Glu Tyr
    130                 135                 140

Pro Gly Arg Phe Asn Ser Thr Asp Pro Ala Phe Ser Trp Phe Pro Val
145                 150                 155                 160

Arg Ala Leu Thr Asp Thr Asp Ile Ser Ala Met Pro Val Ala Pro Glu
                165                 170                 175

Thr Val Pro Val His Thr Arg Ile Leu Asp Asn Val His Asp Gly Val
            180                 185                 190

Gln Phe Val Ser Ala Val Phe Ala Gly Ser Met Gln Tyr Asn Leu Pro
        195                 200                 205

Val Val Lys Ala Gln Ala Thr Ala Gly Ser Asp Tyr Tyr Thr Ile Gly
    210                 215                 220

Arg Leu Pro Gly Ile Met Ser Ala Phe Thr Phe Ser Phe Tyr Thr Lys
225                 230                 235                 240

Gly Thr Pro Gln Asp Ser Arg Phe Phe Arg Asp Thr Val Lys Ala Gly
                245                 250                 255

Gly Asp Leu Arg Glu Ala Gly Phe Thr Val Gly Ala Asn Thr Ser Asp
            260                 265                 270

Phe Ile Ile Trp Phe Pro Gln Gly Ser Gly Leu Glu Pro Leu Tyr Phe
        275                 280                 285

Ser Met Thr Met Asn Met Pro Ala Gly Pro Leu Gln Arg Arg Gln Glu
    290                 295                 300

Ala Glu Asn Lys Ala Arg Ala Glu Ala Asp Arg Leu Arg Ala Glu Ala
305                 310                 315                 320

Glu Ala Lys Ile Arg Ala Glu Ala Glu Ala Arg Ala Lys Ala Glu Ala
                325                 330                 335

Glu Arg Lys Ala Leu Phe Ala Lys Ala Gly Ile Gln Asp Thr Pro Val
            340                 345                 350

Tyr Thr Pro Glu Met Val Lys Ala Ala Asn Ala Leu Ser Ala Gly
        355                 360                 365

Gly Ser Met Ala Leu Ser Arg Ala Pro Gly Met Ile Gln His Ser Ala
```

```
                370                 375                 380
Ala Gly Val Gly Thr Leu Pro Phe Asn Ser Ser Leu Ala Gly Trp Glu
385                 390                 395                 400

Ala Gly Ala Leu Trp Arg Gly Val Asp Val Leu Ala Arg Ile Ala Pro
                405                 410                 415

Val Ala Ser Ala Val Ala Thr Val Ala Thr Val Leu Thr Leu Val Arg
                420                 425                 430

Ala Ala Leu Asp Ile Pro Ala Ala Gly Glu Gly Ser Asp Arg Val Pro
                435                 440                 445

Gly Arg Asn Ile Asp Met Leu Ala Ala Gln Ala Ser Leu Tyr Thr Ala
                450                 455                 460

Met Lys Thr Asn Ile Gln Pro Gly Met Lys Thr Val Asp Leu Pro Val
465                 470                 475                 480

Arg Gly Tyr Ile Ser Tyr Asp Gly Asn Gly Arg Gln Ser Val Asn Leu
                485                 490                 495

Val Arg Thr Gly Thr Gly Gly Val Ser Ala Thr Val Pro Val Leu Ser
                500                 505                 510

Ala Val Arg Asp Lys Thr Thr Gly Leu Asp Lys Ile Thr Val Pro Ala
                515                 520                 525

Val Ala Gly Ala Pro Ser Arg Thr Ile Leu Ile Asn Pro Val Pro Val
                530                 535                 540

Gly Pro Ala Thr Pro Ser His Thr Gly Ser Ser Thr Pro Val Pro Val
545                 550                 555                 560

Thr Pro Val His Thr Gly Thr Asp Val Lys Gln Ala Asp Ser Ile Val
                565                 570                 575

Thr Thr Thr Leu Pro Ala Ala Asp Ile Pro Ala Leu Gln Asp Phe Ile
                580                 585                 590

Tyr Trp Gln Pro Asp Ala Thr Gly Thr Gly Val Glu Pro Ile Tyr Val
                595                 600                 605

Met Leu Ser Asp Pro Leu Asp Ser Gly Lys Tyr Thr Arg Arg Gln Leu
                610                 615                 620

Gln Lys Lys Tyr Lys His Ala Ile Asp Phe Gly Ile Thr Asp Thr Lys
625                 630                 635                 640

Ile Asn Gly Glu Thr Leu Thr Lys Phe Arg Asp Ala Ile Glu Ala His
                645                 650                 655

Leu Ser Asp Lys Asp Thr Phe Glu Lys Gly Thr Tyr Arg Arg Asp Lys
                660                 665                 670

Gly Ser Lys Val Tyr Phe Asn Pro Lys Thr Met Asn Ala Val Ile Ile
                675                 680                 685

Gln Ala Asn Gly Asp Phe Leu Ser Gly Trp Lys Ile Asn Pro Ala Ala
                690                 695                 700

Asp Asn Gly Arg Ile Tyr Leu Glu Thr Gly Asp Leu
705                 710                 715

<210> SEQ ID NO 9
<211> LENGTH: 1386
<212> TYPE: DNA
<213> ORGANISM: Artificial Sequence
<220> FEATURE:
<223> OTHER INFORMATION: DNA sequence of Klebicin CCL along with
      immunity gene. AF190857.1:166-1854 Klebsiella pneumoniae cloacin
      operon, complete sequence, 1956 bases

<400> SEQUENCE: 9
atgagtggtg gagacggtcg aggtccgggt aattcaggtc tgggacataa tggtggtcag      60
```

```
gccagtggga atgtgaacgg tacgtctggt aaaggcggcc cttcatcagg tgggggtacg    120
gatccaaaca gcgggccggg ctggggtacg acgcatacgc taacggaga tattcataac    180 tacaatccgg gggagtttgg tcacggaggg aataaacccg gtggcaatgg cggtaacagc    240
ggcaatcatc ccggtagttc tggtggcaga cagtcttcgg ccacagcgat ggccttcggt    300
ctgcctgctc tggctactcc gggctccggg gggctggctt tagccgtttc cggcgatgcg    360
ttgtcggcag ccgttgctag tgtgctggct gccctgaaag gccgtttaa gaaaagagac     420 tatgataaag cgaaagccga gctggatgcc gaagataaaa atattgcgac cttaaacagc    480
cgcattgcat cgacagagaa ggcgctcccc ggtgcaaggg ctgctgttca ggaagccgat    540
aaaaaggtga agaggcaga ggcgaataag gatgattttg tgacttataa ccctcctcat     600
gaatatggct ccgggtggca ggatcaggtt cgctatcttg ataaggatat tcagaatcag    660
aatgcgaaat taaaagcggc tcaggcatct ttaaacgcaa tgaatgaatc cttatccaga    720
gataaggctt gcacttcccg ggcgatggag agccggaaac aaaaggagaa aaaagcgaag    780
gatgcagaaa ataagttaaa tgaggaaaag aaaaaacctc gcaagggagc taaagactac    840
ggccatgatt atcatccagc cccgaaaact gaagacataa agggactggg tgacctcaaa    900
aaaggtacac taaaacacc aatgcaggga ggtggaggta ggcgtaaacg ctggattggt     960
gataaaggcc gtaagattta tgaatgggac tcccagcacg gtgagcttga agggtatcgt   1020
gccagtgatg gcgaacacct cggggcattt gatcctaaaa cgggtaagca aattaaaggt   1080
ccggatccga aagggcgaaa cattaaaaaa tatctttaag aggtaagtat gggacttaaa   1140
ttaaatttaa cctggtttga taagaaaact gaagagttta aggggaaga gtattctaaa    1200 gactttggtg atgatggttc tgtcattgaa agtcttggga tgcctttaaa ggataatatt   1260
aacaatggtt gttttgatgt gaaaaatgag tgggtttcat tattgcaacc ctactttaaa   1320
cataaaatca atctttctga tagttcatat tttgtttcat ttgattatcg ggatggtaac   1380
tggtaa                                                             1386
```

<210> SEQ ID NO 10
<211> LENGTH: 562
<212> TYPE: PRT
<213> ORGANISM: Artificial Sequence
<220> FEATURE:
<223> OTHER INFORMATION: Amino acid sequence of klebicin CCL

<400> SEQUENCE: 10

```
Met Ser Gly Gly Asp Gly Arg Gly Pro Gly Asn Ser Gly Leu Gly His
1               5                   10                  15

Asn Gly Gly Gln Ala Ser Gly Asn Val Asn Gly Thr Ser Gly Lys Gly
                20                  25                  30

Gly Pro Ser Ser Gly Gly Thr Asp Pro Asn Ser Gly Pro Gly Trp
            35                  40                  45

Gly Thr Thr His Thr Pro Asn Gly Asp Ile His Asn Tyr Asn Pro Gly
        50                  55                  60

Glu Phe Gly His Gly Gly Asn Lys Pro Gly Gly Asn Gly Gly Asn Ser
65                  70                  75                  80

Gly Asn His Pro Gly Ser Ser Gly Gly Arg Gln Ser Ser Ala Thr Ala
                85                  90                  95

Met Ala Phe Gly Leu Pro Ala Leu Ala Thr Pro Gly Ser Gly Gly Leu
            100                 105                 110

Ala Leu Ala Val Ser Gly Asp Ala Leu Ser Ala Ala Val Ala Ser Val
        115                 120                 125
```

```
Leu Ala Ala Leu Lys Gly Pro Phe Lys Phe Gly Leu Trp Gly Ile Ala
    130                 135                 140
Ile Tyr Gly Val Leu Pro Ser Glu Ile Ala Lys Asp Asp Pro Lys Met
145                 150                 155                 160
Met Ser Lys Ile Met Thr Ser Leu Pro Ala Asp Ala Val Thr Glu Thr
                165                 170                 175
Pro Ala Ser Thr Leu Pro Leu Asp Gln Ala Thr Val Arg Val Arg Gln
            180                 185                 190
Arg Val Val Asp Val Val Lys Asp Glu Arg Gln His Ile Ala Val Val
        195                 200                 205
Ala Gly Arg Pro Met Ser Val Pro Val Val Asp Ala Lys Pro Thr Lys
    210                 215                 220
Arg Pro Gly Val Phe Ser Val Ser Ile Pro Gly Leu Pro Ser Leu Gln
225                 230                 235                 240
Val Ser Val Pro Lys Gly Val Pro Thr Ala Lys Ala Pro Pro Lys Gly
                245                 250                 255
Ile Val Ala Glu Lys Gly Asp Ser Arg Pro Ala Gly Phe Thr Ala Gly
            260                 265                 270
Gly Asn Ser Arg Glu Ala Val Ile Arg Phe Pro Lys Glu Thr Gly Gln
        275                 280                 285
Lys Pro Val Tyr Val Ser Val Thr Asp Val Leu Thr Pro Ala Gln Val
    290                 295                 300
Lys Gln Arg Gln Glu Glu Glu Lys Arg Arg Gln Gln Ala Trp Asp Ala
305                 310                 315                 320
Ala His Pro Glu Glu Gly Leu Lys Arg Asp Tyr Asp Lys Ala Lys Ala
                325                 330                 335
Glu Leu Asp Ala Glu Asp Lys Asn Ile Ala Thr Leu Asn Ser Arg Ile
            340                 345                 350
Ala Ser Thr Glu Lys Ala Leu Pro Gly Ala Arg Ala Ala Val Gln Glu
        355                 360                 365
Ala Asp Lys Lys Val Lys Glu Ala Glu Ala Asn Lys Asp Asp Phe Val
    370                 375                 380
Thr Tyr Asn Pro Pro His Glu Tyr Gly Ser Gly Trp Gln Asp Gln Val
385                 390                 395                 400
Arg Tyr Leu Asp Lys Asp Ile Gln Asn Gln Asn Ala Lys Leu Lys Ala
                405                 410                 415
Ala Gln Ala Ser Leu Asn Ala Met Asn Glu Ser Leu Ser Arg Asp Lys
            420                 425                 430
Ala Cys Thr Ser Arg Ala Met Glu Ser Arg Lys Gln Lys Glu Lys Lys
        435                 440                 445
Ala Lys Asp Ala Glu Asn Lys Leu Asn Glu Glu Lys Lys Lys Pro Arg
    450                 455                 460
Lys Gly Ala Lys Asp Tyr Gly His Asp Tyr His Pro Ala Pro Lys Thr
465                 470                 475                 480
Glu Asp Ile Lys Gly Leu Gly Asp Leu Lys Lys Gly Thr Pro Lys Thr
                485                 490                 495
Pro Met Gln Gly Gly Gly Gly Arg Arg Lys Arg Trp Ile Gly Asp Lys
            500                 505                 510
Gly Arg Lys Ile Tyr Glu Trp Asp Ser Gln His Gly Glu Leu Glu Gly
        515                 520                 525
Tyr Arg Ala Ser Asp Gly Glu His Leu Gly Ala Phe Asp Pro Lys Thr
    530                 535                 540
```

| | | | | | | | | | | | | | | |
|---|---|---|---|---|---|---|---|---|---|---|---|---|---|---|
| Gly | Lys | Gln | Ile | Lys | Gly | Pro | Asp | Pro | Lys | Gly | Arg | Asn | Ile | Lys | Lys |
| 545 | | | | 550 | | | | | 555 | | | | | 560 |

Tyr Leu

<210> SEQ ID NO 11
<211> LENGTH: 2107
<212> TYPE: DNA
<213> ORGANISM: Artificial Sequence
<220> FEATURE:
<223> OTHER INFORMATION: Klebicin CCL TDRD + Kleb B KD + Imm: 2107 bases

<400> SEQUENCE: 11

```
atgagtggtg agacggtcg aggtccgggt aattcaggtc tgggacataa tggtggtcag     60
gccagtggga atgtgaacgg tacgtctggt aaaggcggcc cttcatcagg tggggtacg    120
gatccaaaca gcgggccggg ctggggtacg acgcatacgc taacggaga tattcataac    180
tacaatccgg gggagtttgg tcacggaggg aataaacccg gtggcaatgg cggtaacagc    240
ggcaatcatc ccggtagttc tggtggcaga cagtcttcgg ccacagcgat ggccttcggt    300
ctgcctgctc tggctactcc gggctccggg gggctggctt tagccgtttc cggcgatgcg    360
ttgtcggcag ccgttgctag tgtgctggct gccctgaaag gccgtttaa gtttggtctg    420
tgggggattg cgatctacgg tgtgctgcct tctgagattg caaaagatga tccgaaaatg    480
atgtcaaaaa ttatgacgtc attaccggcc gatgcggtga cggagactcc ggcaagtact    540
ttaccactgg accaggcgac ggttcgtgtc agacaacggg ttgtggatgt ggtgaaggat    600
gagcggcagc atattgcggt tgtcgcaggt cggccaatga gtgtccctgt ggtggatgcg    660
aaaccgacaa acgtccgggg gtattcagt gtgtcgattc cgggtctccc gtctctgcag    720
gtgagcgtac cgaaaggtgt tccgacagcg aaagccccgc caaaaggcat tgttgctgaa    780
aaaggtgatt cacgtccggc tggttttaca gccggtggta actcccgtga ggccgttatt    840
cgtttcccga agagaccgg acagaagccg gtttatgtgt cggtgacaga tgttcttacc    900
ccggcacagg taaacagcg tcaggaggaa gaaaagcgtc gccagcaggc atgggacgcc    960
gctcatccgg aagaggggct gaaaagagac tatgataaag cgaaagccga gctggatgcc   1020
gaagataaaa atattgcgac cttaaacagc cgcattgcat cgacagagaa ggcgctcccc   1080
ggtgcaaggg ctgctgttca ggaagccgat aaaaaggtga agaggcaga ggcgaataag   1140
gatgattttg tgacttataa ccctcctcat gaatatggct ccgggtggca ggatcaggtt   1200
cgctatcttg ataaggatat tcagaatcag aatgcgaaat taaaagcggc tcaggcatct   1260
ttaaacgcaa tgaatgaatc cttatccaga gataaggctt gcacttcccg ggcgatggag   1320
agccggaaac aaaaggagaa aaaagcgaag gatgcagaaa ataagttaaa tgaggaaaag   1380
aaaaaacctc gcaagggagc taaagactac ggccatgatg gtcttaaacc gttgtatgtg   1440
atgtaccgta gccctcgtaa catgccgggg acagccagtg gtaaaggtca gaacgttgga   1500
aataactgga tggggggggac cagtaccggg gatggtgctc ctgttccttc ccagattgca   1560
gataaattac gtgggaaggc tttcggtagt tttgattctt tctgtcgggc tttctggaaa   1620
gcggttgctg ctgatccgga cctcagtaag cagtttttatc ctgatgatat agagcgaatg   1680
aaattagggc gagctccaac agttcgattc cgagattctg taggtaaaag ggttaaggtt   1740
gaactacacc ataaagttga aatttctaaa ggtggtgatg tctataacgt agataacctg   1800
aatgcattaa cacctaaacg tcatattgaa attcataagg ggaactgaaa tggctaataa   1860
aactttggct gactatacag agcaggaatt tattgagttt atcgaaaaaa ttaaaaaggc   1920
```

```
agactttgct actgagtctg agcatgatga ggctatttat gagttcagcc agttgactga    1980
gcatccagat ggttgggatc ttatttatca tcctcaagca ggagccgata actctcctgc    2040
tggtgttgta aaacagtaa aagagtggcg agcagctaac ggtaagccag gttttaaaaa     2100
atcgtga                                                              2107
```

<210> SEQ ID NO 12
<211> LENGTH: 615
<212> TYPE: PRT
<213> ORGANISM: Artificial Sequence
<220> FEATURE:
<223> OTHER INFORMATION: Kleb CCL TD RBD (1-1419); Klebicib B KD
      (1420-1849); Klebicibn B Immunity protein (1850-end)

<400> SEQUENCE: 12

```
Met Ser Gly Gly Asp Gly Arg Gly Pro Gly Asn Ser Gly Leu Gly His
1               5                   10                  15

Asn Gly Gly Gln Ala Ser Gly Asn Val Asn Gly Thr Ser Gly Lys Gly
            20                  25                  30

Gly Pro Ser Ser Gly Gly Thr Asp Pro Asn Ser Gly Pro Gly Trp
        35                  40                  45

Gly Thr Thr His Thr Pro Asn Gly Asp Ile His Asn Tyr Asn Pro Gly
50                  55                  60

Glu Phe Gly His Gly Gly Asn Lys Pro Gly Gly Asn Gly Gly Asn Ser
65                  70                  75                  80

Gly Asn His Pro Gly Ser Ser Gly Gly Arg Gln Ser Ser Ala Thr Ala
                85                  90                  95

Met Ala Phe Gly Leu Pro Ala Leu Ala Thr Pro Gly Ser Gly Gly Leu
            100                 105                 110

Ala Leu Ala Val Ser Gly Asp Ala Leu Ser Ala Ala Val Ala Ser Val
        115                 120                 125

Leu Ala Ala Leu Lys Gly Pro Phe Lys Phe Gly Leu Trp Gly Ile Ala
    130                 135                 140

Ile Tyr Gly Val Leu Pro Ser Glu Ile Ala Lys Asp Asp Pro Lys Met
145                 150                 155                 160

Met Ser Lys Ile Met Thr Ser Leu Pro Ala Asp Ala Val Thr Glu Thr
                165                 170                 175

Pro Ala Ser Thr Leu Pro Leu Asp Gln Ala Thr Val Arg Val Arg Gln
            180                 185                 190

Arg Val Val Asp Val Val Lys Asp Glu Arg Gln His Ile Ala Val Val
        195                 200                 205

Ala Gly Arg Pro Met Ser Val Pro Val Val Asp Ala Lys Pro Thr Lys
    210                 215                 220

Arg Pro Gly Val Phe Ser Val Ser Ile Pro Gly Leu Pro Ser Leu Gln
225                 230                 235                 240

Val Ser Val Pro Lys Gly Val Pro Thr Ala Lys Ala Pro Pro Lys Gly
                245                 250                 255

Ile Val Ala Glu Lys Gly Asp Ser Arg Pro Ala Gly Phe Thr Ala Gly
            260                 265                 270

Gly Asn Ser Arg Glu Ala Val Ile Arg Phe Pro Lys Glu Thr Gly Gln
        275                 280                 285

Lys Pro Val Tyr Val Ser Val Thr Asp Val Leu Thr Pro Ala Gln Val
    290                 295                 300

Lys Gln Arg Gln Glu Glu Glu Lys Arg Arg Gln Gln Ala Trp Asp Ala
305                 310                 315                 320
```

-continued

```
Ala His Pro Glu Glu Gly Leu Lys Arg Asp Tyr Asp Lys Ala Lys Ala
                325                 330                 335

Glu Leu Asp Ala Glu Asp Lys Asn Ile Ala Thr Leu Asn Ser Arg Ile
            340                 345                 350

Ala Ser Thr Glu Lys Ala Leu Pro Gly Ala Arg Ala Ala Val Gln Glu
        355                 360                 365

Ala Asp Lys Lys Val Lys Glu Ala Glu Ala Asn Lys Asp Asp Phe Val
    370                 375                 380

Thr Tyr Asn Pro Pro His Glu Tyr Gly Ser Gly Trp Gln Asp Gln Val
385                 390                 395                 400

Arg Tyr Leu Asp Lys Asp Ile Gln Asn Gln Asn Ala Lys Leu Lys Ala
                405                 410                 415

Ala Gln Ala Ser Leu Asn Ala Met Asn Glu Ser Leu Ser Arg Asp Lys
            420                 425                 430

Ala Cys Thr Ser Arg Ala Met Glu Ser Arg Lys Gln Lys Glu Lys Lys
        435                 440                 445

Ala Lys Asp Ala Glu Asn Lys Leu Asn Glu Glu Lys Lys Lys Pro Arg
    450                 455                 460

Lys Gly Ala Lys Asp Tyr Gly His Asp Gly Leu Lys Pro Leu Tyr Val
465                 470                 475                 480

Met Tyr Arg Ser Pro Arg Asn Met Pro Gly Thr Ala Ser Gly Lys Gly
                485                 490                 495

Gln Asn Val Gly Asn Asn Trp Met Gly Gly Thr Ser Thr Gly Asp Gly
            500                 505                 510

Ala Pro Val Pro Ser Gln Ile Ala Asp Lys Leu Arg Gly Lys Ala Phe
        515                 520                 525

Gly Ser Phe Asp Ser Phe Cys Arg Ala Phe Trp Lys Ala Val Ala Ala
    530                 535                 540

Asp Pro Asp Leu Ser Lys Gln Phe Tyr Pro Asp Asp Ile Glu Arg Met
545                 550                 555                 560

Lys Leu Gly Arg Ala Pro Thr Val Arg Phe Arg Asp Ser Val Gly Lys
                565                 570                 575

Arg Val Lys Val Glu Leu His His Lys Val Glu Ile Ser Lys Gly Gly
            580                 585                 590

Asp Val Tyr Asn Val Asp Asn Leu Asn Ala Leu Thr Pro Lys Arg His
        595                 600                 605

Ile Glu Ile His Lys Gly Asn
    610                 615

<210> SEQ ID NO 13
<211> LENGTH: 1590
<212> TYPE: DNA
<213> ORGANISM: Artificial Sequence
<220> FEATURE:
<223> OTHER INFORMATION: P623: S5 TD-RD-Linker-GP36 CD-his: 1590 bases

<400> SEQUENCE: 13
atgtccaatg acaacgaagt acctggttcc atggttattg tcgcacaagg tccagacgat        60
caatacgcat acgaggttcc ccctatcgat agcgcggccg ttgccgggaa tatgtttggc       120
gacttaattc aaagagaaat atatctacag aaaaacattt attatccagt ccgatctatt       180
tttgaacaag gaacaaaaga aaagaaggag atcaacaaga agtatctga tcaagtcgat        240 ggcttgctaa agcagatcac tcaaggaaaa agggaggcca aaggcaaga gcgagtcgat        300 gtcatgtcgg cagtcctgca aagatggaa tctgatcttg aaggatacaa aaagaccttt        360
```

```
accaaaggcc cattcattga ctacgaaaag cagtcaagcc tctccatcta tgaggcctgg    420
gtcaagatct gggagaagaa ctcttgggaa gaaagaaaga agtaccctttt tcagcagctt    480 gttagagatg aactggagcg ggcggttgcc tactacaaac aagattcact ctctgaagcg    540
gtaaaagtgc taagacagga gctcaacaag caaaaagcgc taaggaaaa agaggacctc    600 tctcaactgg agcgggacta cagaacccga aaggcgaatc tcgagatgaa agtacaatcc    660
gagcttgatc aagcgggaag tgctttgcct ccattggtca gtccaacgcc agagcaatgg    720
cttgaacgtg ccacaagact ggttacgcaa gcaattgctg ataaaaagca gctgcagacc    780
acaaacaata ctcttatcaa gaattcccca accctctag aaaagcagaa agccatctac     840
aatggtgagc tacttgtgga tgagatagcc agtctacagg cccgcttagt taagctgaac    900
ggaggaggag gatcaggtgt ggccctggac cgcacgcggg ttgatcccca ggcagtcggc    960
aacgaggtgc tcaagcgcaa cgcggataag ctgaatgcga tgcggggcgc cgagtacggt   1020
gccaacgtca aggtcagcgg cacggacatt cgcatgaacg ggggtaacag tgccggcatg   1080
ctgaagcagg acgtgttcaa ctggcggaag gaactggctc agttcgaggc ttaccgaggg   1140
gaggcgtata aggatgccga tggttatagt gtgggcctgg ggcattacct gggcagtggc   1200
aatgctgggg caggtactac agtcacgcct gagcaagccg cgcagtggtt cgccgaggac   1260
accgaccgcg cactcgacca gggtgtgagg ttggccgacg agctgggcgt tacgaacaat   1320
gcctctatcc tgggattggc cggtatggcc ttccagatgg gcgaaggacg tgcccggcag   1380
ttccgtaaca ccttccaggc gatcaaggat cgcaacaagg aagccttcga ggctggtgtg   1440
cgaaacagca gtggtacac gcagacgccc aaccggccg aggcattcat caagcgcatg    1500 gcgcccact tcgataacc gagtcaaatc ggtgtcgatt ggtacagcgc cgcaacagcg    1560
gagctcgagc accaccacca ccaccactaa                                    1590
```

<210> SEQ ID NO 14
<211> LENGTH: 529
<212> TYPE: PRT
<213> ORGANISM: Artificial Sequence
<220> FEATURE:
<223> OTHER INFORMATION: Protein; Theoretical pI/Mw: 6.56 / 59443.77

<400> SEQUENCE: 14

```
Met Ser Asn Asp Asn Glu Val Pro Gly Ser Met Val Ile Val Ala Gln
1               5                   10                  15

Gly Pro Asp Asp Gln Tyr Ala Tyr Glu Val Pro Pro Ile Asp Ser Ala
            20                  25                  30

Ala Val Ala Gly Asn Met Phe Gly Asp Leu Ile Gln Arg Glu Ile Tyr
        35                  40                  45

Leu Gln Lys Asn Ile Tyr Tyr Pro Val Arg Ser Ile Phe Glu Gln Gly
    50                  55                  60

Thr Lys Glu Lys Lys Glu Ile Asn Lys Val Ser Asp Gln Val Asp
65                  70                  75                  80

Gly Leu Leu Lys Gln Ile Thr Gln Gly Lys Arg Glu Ala Thr Arg Gln
                85                  90                  95

Glu Arg Val Asp Val Met Ser Ala Val Leu His Lys Met Glu Ser Asp
            100                 105                 110

Leu Glu Gly Tyr Lys Lys Thr Phe Thr Lys Gly Pro Phe Ile Asp Tyr
        115                 120                 125

Glu Lys Gln Ser Ser Leu Ser Ile Tyr Glu Ala Trp Val Lys Ile Trp
    130                 135                 140
```

```
Glu Lys Asn Ser Trp Glu Arg Lys Lys Tyr Pro Phe Gln Gln Leu
145                 150                 155                 160

Val Arg Asp Glu Leu Glu Arg Ala Val Ala Tyr Tyr Lys Gln Asp Ser
            165                 170                 175

Leu Ser Glu Ala Val Lys Val Leu Arg Gln Glu Leu Asn Lys Gln Lys
            180                 185                 190

Ala Leu Lys Glu Lys Glu Asp Leu Ser Gln Leu Glu Arg Asp Tyr Arg
            195                 200                 205

Thr Arg Lys Ala Asn Leu Glu Met Lys Val Gln Ser Glu Leu Asp Gln
210                 215                 220

Ala Gly Ser Ala Leu Pro Pro Leu Val Ser Pro Thr Pro Glu Gln Trp
225                 230                 235                 240

Leu Glu Arg Ala Thr Arg Leu Val Thr Gln Ala Ile Ala Asp Lys Lys
            245                 250                 255

Gln Leu Gln Thr Thr Asn Asn Thr Leu Ile Lys Asn Ser Pro Thr Pro
            260                 265                 270

Leu Glu Lys Gln Lys Ala Ile Tyr Asn Gly Glu Leu Leu Val Asp Glu
            275                 280                 285

Ile Ala Ser Leu Gln Ala Arg Leu Val Lys Leu Asn Gly Gly Gly Gly
290                 295                 300

Ser Gly Val Ala Leu Asp Arg Thr Arg Val Asp Pro Gln Ala Val Gly
305                 310                 315                 320

Asn Glu Val Leu Lys Arg Asn Ala Asp Lys Leu Asn Ala Met Arg Gly
            325                 330                 335

Ala Glu Tyr Gly Ala Asn Val Lys Val Ser Gly Thr Asp Ile Arg Met
            340                 345                 350

Asn Gly Gly Asn Ser Ala Gly Met Leu Lys Gln Asp Val Phe Asn Trp
            355                 360                 365

Arg Lys Glu Leu Ala Gln Phe Glu Ala Tyr Arg Gly Glu Ala Tyr Lys
            370                 375                 380

Asp Ala Asp Gly Tyr Ser Val Gly Leu Gly His Tyr Leu Gly Ser Gly
385                 390                 395                 400

Asn Ala Gly Ala Gly Thr Thr Val Thr Pro Glu Gln Ala Ala Gln Trp
            405                 410                 415

Phe Ala Glu Asp Thr Asp Arg Ala Leu Asp Gln Gly Val Arg Leu Ala
            420                 425                 430

Asp Glu Leu Gly Val Thr Asn Asn Ala Ser Ile Leu Gly Leu Ala Gly
            435                 440                 445

Met Ala Phe Gln Met Gly Glu Gly Arg Ala Arg Gln Phe Arg Asn Thr
450                 455                 460

Phe Gln Ala Ile Lys Asp Arg Asn Lys Glu Ala Phe Glu Ala Gly Val
465                 470                 475                 480

Arg Asn Ser Lys Trp Tyr Thr Gln Thr Pro Asn Arg Ala Glu Ala Phe
            485                 490                 495

Ile Lys Arg Met Ala Pro His Phe Asp Thr Pro Ser Gln Ile Gly Val
            500                 505                 510

Asp Trp Tyr Ser Ala Ala Thr Ala Glu Leu Glu His His His His His
            515                 520                 525

His

<210> SEQ ID NO 15
<211> LENGTH: 1566
<212> TYPE: DNA
<213> ORGANISM: Artificial Sequence
```

<220> FEATURE:
<223> OTHER INFORMATION: P624: S5 TD-RD-Link-GP36 CD without his tag: 1572 bases

<400> SEQUENCE: 15

```
atgtccaatg acaacgaagt acctggttcc atggttattg tcgcacaagg tccagacgat      60
caatacgcat acgaggttcc ccctatcgat agcgcggccg ttgccgggaa tatgtttggc     120
gacttaattc aaagagaaat atatctacag aaaaacattt attatccagt ccgatctatt     180
tttgaacaag gaacaaaaga aagaaggag atcaacaaga aagtatctga tcaagtcgat      240
ggcttgctaa agcagatcac tcaaggaaaa agggaggcca caaggcaaga gcgagtcgat     300
gtcatgtcgg cagtcctgca caagatggaa tctgatcttg aaggatacaa aaagaccttt     360
accaaaggcc cattcattga ctacgaaaag cagtcaagcc tctccatcta tgaggcctgg     420
gtcaagatct gggagaagaa ctcttgggaa gaaagaaaga agtacccttt tcagcagctt     480
gttagagatg aactggagcg ggcggttgcc tactacaaac aagattcact ctctgaagcg     540
gtaaaagtgc taagacagga gctcaacaag caaaaagcgc taaggaaaaa agaggacctc     600
tctcaactgg agcgggacta cagaacccga aaggcgaatc tcgagatgaa agtacaatcc     660
gagcttgatc aagcgggaag tgctttgcct ccattggtca gtccaacgcc agagcaatgg     720
cttgaacgtg ccacaagact ggttacgcaa gcaattgctg ataaaaagca gctgcagacc     780
acaaacaata ctcttatcaa gaattcccca acccctctag aaaagcagaa agccatctac     840
aatggtgagc tacttgtgga tgagatagcc agtctacagg cccgcttagt taagctgaac     900
ggaggaggag gatcaggtgt ggccctggac cgcacgcggg ttgatcccca ggcagtcggc     960
aacgaggtgc tcaagcgcaa cgcggataag ctgaatgcga tgcggggcgc cgagtacggt    1020
gccaacgtca aggtcagcgg cacggacatt cgcatgaacg ggggtaacag tgccggcatg    1080
ctgaagcagg acgtgttcaa ctggcggaag gaactggctc agttcgaggc ttaccgaggg    1140
gaggcgtata aggatgccga tggttatagt gtgggcctgg gcattaccct gggcagtggc    1200
aatgctgggg caggtactac agtcacgcct gagcaagccg cgcagtggtt cgccgaggac    1260
accgaccgcg cactcgacca gggtgtgagg ttggccgacg agctgggcgt tacgaacaat    1320
gcctctatcc tgggattggc cggtatggcc ttccagatgg gcgaaggacg tgcccggcag    1380
ttccgtaaca ccttccaggc gatcaaggat cgcaacaagg aagccttcga ggctggtgtg    1440
cgaaacagca gtggtacac gcagacgccc aaccgggccg aggcattcat caagcgcatg    1500
gcgcccccact tcgataccc gagtcaaatc ggtgtcgatt ggtacagcgc cgcaacagcg    1560
gagtaa                                                                1566
```

<210> SEQ ID NO 16
<211> LENGTH: 521
<212> TYPE: PRT
<213> ORGANISM: Artificial Sequence
<220> FEATURE:
<223> OTHER INFORMATION: Protein; Theoretical pI/Mw: 6.19 / 58620.92

<400> SEQUENCE: 16

Met Ser Asn Asp Asn Glu Val Pro Gly Ser Met Val Ile Val Ala Gln
1               5                   10                  15

Gly Pro Asp Asp Gln Tyr Ala Tyr Glu Val Pro Pro Ile Asp Ser Ala
            20                  25                  30

Ala Val Ala Gly Asn Met Phe Gly Asp Leu Ile Gln Arg Glu Ile Tyr
        35                  40                  45

```
Leu Gln Lys Asn Ile Tyr Tyr Pro Val Arg Ser Ile Phe Glu Gln Gly
    50              55                  60

Thr Lys Glu Lys Lys Glu Ile Asn Lys Lys Val Ser Asp Gln Val Asp
 65              70              75                  80

Gly Leu Leu Lys Gln Ile Thr Gln Gly Lys Arg Glu Ala Thr Arg Gln
                85              90              95

Glu Arg Val Asp Val Met Ser Ala Val Leu His Lys Met Glu Ser Asp
            100             105             110

Leu Glu Gly Tyr Lys Lys Thr Phe Thr Lys Gly Pro Phe Ile Asp Tyr
        115             120             125

Glu Lys Gln Ser Ser Leu Ser Ile Tyr Glu Ala Trp Val Lys Ile Trp
    130             135             140

Glu Lys Asn Ser Trp Glu Glu Arg Lys Lys Tyr Pro Phe Gln Gln Leu
145             150             155                 160

Val Arg Asp Glu Leu Glu Arg Ala Val Ala Tyr Tyr Lys Gln Asp Ser
                165             170             175

Leu Ser Glu Ala Val Lys Val Leu Arg Gln Glu Leu Asn Lys Gln Lys
            180             185             190

Ala Leu Lys Glu Lys Glu Asp Leu Ser Gln Leu Glu Arg Asp Tyr Arg
        195             200             205

Thr Arg Lys Ala Asn Leu Glu Met Lys Val Gln Ser Glu Leu Asp Gln
    210             215             220

Ala Gly Ser Ala Leu Pro Pro Leu Val Ser Pro Thr Pro Glu Gln Trp
225             230             235                 240

Leu Glu Arg Ala Thr Arg Leu Val Thr Gln Ala Ile Ala Asp Lys Lys
                245             250             255

Gln Leu Gln Thr Thr Asn Asn Thr Leu Ile Lys Asn Ser Pro Thr Pro
            260             265             270

Leu Glu Lys Gln Lys Ala Ile Tyr Asn Gly Glu Leu Leu Val Asp Glu
        275             280             285

Ile Ala Ser Leu Gln Ala Arg Leu Val Lys Leu Asn Gly Gly Gly Gly
    290             295             300

Ser Gly Val Ala Leu Asp Arg Thr Arg Val Asp Pro Gln Ala Val Gly
305             310             315                 320

Asn Glu Val Leu Lys Arg Asn Ala Asp Lys Leu Asn Ala Met Arg Gly
                325             330             335

Ala Glu Tyr Gly Ala Asn Val Lys Val Ser Gly Thr Asp Ile Arg Met
            340             345             350

Asn Gly Gly Asn Ser Ala Gly Met Leu Lys Gln Asp Val Phe Asn Trp
        355             360             365

Arg Lys Glu Leu Ala Gln Phe Glu Ala Tyr Arg Gly Glu Ala Tyr Lys
    370             375             380

Asp Ala Asp Gly Tyr Ser Val Gly Leu Gly His Tyr Leu Gly Ser Gly
385             390             395                 400

Asn Ala Gly Ala Gly Thr Thr Val Thr Pro Glu Gln Ala Ala Gln Trp
                405             410             415

Phe Ala Glu Asp Thr Asp Arg Ala Leu Asp Gln Gly Val Arg Leu Ala
            420             425             430

Asp Glu Leu Gly Val Thr Asn Asn Ala Ser Ile Leu Gly Leu Ala Gly
        435             440             445

Met Ala Phe Gln Met Gly Glu Gly Arg Ala Arg Gln Phe Arg Asn Thr
    450             455             460

Phe Gln Ala Ile Lys Asp Arg Asn Lys Glu Ala Phe Glu Ala Gly Val
```

```
                465                 470                 475                 480
Arg Asn Ser Lys Trp Tyr Thr Gln Thr Pro Asn Arg Ala Glu Ala Phe
                    485                 490                 495
Ile Lys Arg Met Ala Pro His Phe Asp Thr Pro Ser Gln Ile Gly Val
                500                 505                 510
Asp Trp Tyr Ser Ala Ala Thr Ala Glu
            515                 520

<210> SEQ ID NO 17
<211> LENGTH: 1365
<212> TYPE: DNA
<213> ORGANISM: Artificial Sequence
<220> FEATURE:
<223> OTHER INFORMATION: P625: S5 TD-RD-Link-Phi29CD: 1365 bases

<400> SEQUENCE: 17
atgtccaatg acaacgaagt acctggttcc atggttattg tcgcacaagg tccagacgat      60
caatacgcat acgaggttcc ccctatcgat agcgcggccg ttgccgggaa tatgtttggc     120
gacttaattc aaagagaaat atatctacag aaaaacattt attatccagt ccgatctatt     180
tttgaacaag gaacaaaaga aaagaaggag atcaacaaga agtatctga tcaagtcgat      240
ggcttgctaa agcagatcac tcaaggaaaa agggaggcca caaggcaaga gcgagtcgat     300
gtcatgtcgg cagtcctgca caagatgaa tctgatcttg aaggatacaa aaagaccttt      360
accaaaggcc cattcattga ctacgaaaag cagtcaagcc tctccatcta tgaggcctgg     420
gtcaagatct gggagaagaa ctcttgggaa gaaagaaaga gtaccctttt cagcagctt     480
gttagagatg aactggagcg gcggttgcc tactacaaac aagattcact ctctgaagcg      540
gtaaaagtgc taagacagga gctcaacaag caaaaagcgc taaggaaaaa agaggacctc     600
tctcaactgg agcgggacta cagaacccga aaggcgaatc tcgagatgaa agtacaatcc     660
gagcttgatc aagcgggaag tgctttgcct ccattggtca gtccaacgcc agagcaatgg     720
cttgaacgtg ccacaagact ggttacgcaa gcaattgctg ataaaaagca gctgcagacc     780
acaaacaata ctcttatcaa gaattcccca accctctag aaaagcagaa agccatctac       840
aatggtgagc tacttgtgga tgagatagcc agtctacagg cccgcttagt taagctgaac     900
ggaggaggag gatcacaaat ttcacaagcg ggtatcaact taattaagag ctttgagggt     960
ttacaactga agcatataa agctgttccg actgagaagc attacaccat ggttacggt     1020
cattacggtt ccgatgtttc acctaggcag ttatcactg ctaaacaggc tgaagacatg     1080
ttgcgtgatg atgtgcaggc ttttgtggat ggtgtaaata agcattaaa agtatctgtc     1140
acccaaaatc aatttgatgc acttgtctca ttcgcttaca cgttgggtt aggggctttc     1200
aggtcttctt ctctactgga atacttgaat gaaggaagaa cagctctagc ggcggctgaa     1260
ttccctaaat ggaataagtc aggcggtaaa gtttatcaag ggttgattaa ccgtagagca     1320
caggagcaag ccttgtttaa tagtggaaca cctaaaaatg tttaa                     1365

<210> SEQ ID NO 18
<211> LENGTH: 454
<212> TYPE: PRT
<213> ORGANISM: Artificial Sequence
<220> FEATURE:
<223> OTHER INFORMATION: Protein; Theoretical pI/Mw: 8.71 / 51160.99

<400> SEQUENCE: 18

Met Ser Asn Asp Asn Glu Val Pro Gly Ser Met Val Ile Val Ala Gln
1               5                   10                  15
```

Gly Pro Asp Asp Gln Tyr Ala Tyr Glu Val Pro Pro Ile Asp Ser Ala
            20                  25                  30

Ala Val Ala Gly Asn Met Phe Gly Asp Leu Ile Gln Arg Glu Ile Tyr
            35                  40                  45

Leu Gln Lys Asn Ile Tyr Tyr Pro Val Arg Ser Ile Phe Glu Gln Gly
        50                  55                  60

Thr Lys Glu Lys Lys Glu Ile Asn Lys Val Ser Asp Gln Val Asp
65                  70                  75                  80

Gly Leu Leu Lys Gln Ile Thr Gln Gly Lys Arg Glu Ala Thr Arg Gln
                85                  90                  95

Glu Arg Val Asp Val Met Ser Ala Val Leu His Lys Met Glu Ser Asp
                100                 105                 110

Leu Glu Gly Tyr Lys Lys Thr Phe Thr Lys Gly Pro Phe Ile Asp Tyr
            115                 120                 125

Glu Lys Gln Ser Ser Leu Ser Ile Tyr Glu Ala Trp Val Lys Ile Trp
130                 135                 140

Glu Lys Asn Ser Trp Glu Arg Lys Lys Tyr Pro Phe Gln Gln Leu
145                 150                 155                 160

Val Arg Asp Glu Leu Glu Arg Ala Val Ala Tyr Tyr Lys Gln Asp Ser
                165                 170                 175

Leu Ser Glu Ala Val Lys Val Leu Arg Gln Glu Leu Asn Lys Gln Lys
            180                 185                 190

Ala Leu Lys Glu Lys Glu Asp Leu Ser Gln Leu Glu Arg Asp Tyr Arg
            195                 200                 205

Thr Arg Lys Ala Asn Leu Glu Met Lys Val Gln Ser Glu Leu Asp Gln
210                 215                 220

Ala Gly Ser Ala Leu Pro Pro Leu Val Ser Pro Thr Pro Glu Gln Trp
225                 230                 235                 240

Leu Glu Arg Ala Thr Arg Leu Val Thr Gln Ala Ile Ala Asp Lys Lys
            245                 250                 255

Gln Leu Gln Thr Thr Asn Asn Thr Leu Ile Lys Asn Ser Pro Thr Pro
            260                 265                 270

Leu Glu Lys Gln Lys Ala Ile Tyr Asn Gly Glu Leu Leu Val Asp Glu
            275                 280                 285

Ile Ala Ser Leu Gln Ala Arg Leu Val Lys Leu Asn Gly Gly Gly
290                 295                 300

Ser Gln Ile Ser Gln Ala Gly Ile Asn Leu Ile Lys Ser Phe Glu Gly
305                 310                 315                 320

Leu Gln Leu Lys Ala Tyr Lys Ala Val Pro Thr Glu Lys His Tyr Thr
            325                 330                 335

Ile Gly Tyr Gly His Tyr Gly Ser Asp Val Ser Pro Arg Gln Val Ile
            340                 345                 350

Thr Ala Lys Gln Ala Glu Asp Met Leu Arg Asp Val Gln Ala Phe
            355                 360                 365

Val Asp Gly Val Asn Lys Ala Leu Lys Val Ser Val Thr Gln Asn Gln
            370                 375                 380

Phe Asp Ala Leu Val Ser Phe Ala Tyr Asn Val Gly Leu Gly Ala Phe
385                 390                 395                 400

Arg Ser Ser Ser Leu Leu Glu Tyr Leu Asn Glu Gly Arg Thr Ala Leu
                405                 410                 415

Ala Ala Ala Glu Phe Pro Lys Trp Asn Lys Ser Gly Gly Lys Val Tyr
            420                 425                 430

```
Gln Gly Leu Ile Asn Arg Arg Ala Gln Glu Gln Ala Leu Phe Asn Ser
        435                 440                 445

Gly Thr Pro Lys Asn Val
    450
```

<210> SEQ ID NO 19
<211> LENGTH: 1404
<212> TYPE: DNA
<213> ORGANISM: Artificial Sequence
<220> FEATURE:
<223> OTHER INFORMATION: P626: S5 TD-RD-Link-BP7e: 1422 bases

<400> SEQUENCE: 19

```
atgtccaatg acaacgaagt acctggttcc atggttattg tcgcacaagg tccagacgat      60
caatacgcat acgaggttcc ccctatcgat agcgcggccg ttgccgggaa tatgtttggc     120
gacttaattc aaagagaaat atatctacag aaaaacattt attatccagt ccgatctatt     180
tttgaacaag gaacaaaaga aagaaggag atcaacaaga agtatctga tcaagtcgat       240
ggcttgctaa agcagatcac tcaaggaaaa agggaggcca caaggcaaga gcgagtcgat     300
gtcatgtcgg cagtcctgca caagatggaa tctgatcttg aaggatacaa aaagaccttt    360
accaaaggcc cattcattga ctacgaaaag cagtcaagcc tctccatcta tgaggcctgg    420
gtcaagatct gggagaagaa ctcttgggaa gaaagaaga agtacccttt tcagcagctt     480
gttagagatg aactggagcg ggcggttgcc tactacaaac aagattcact ctctgaagcg    540
gtaaaagtgc taagacagga gctcaacaag caaaaagcgc taaggaaaa agaggacctc     600
tctcaactgg agcgggacta cagaacccga aaggcgaatc tcgagatgaa agtacaatcc    660
gagcttgatc aagcgggaag tgctttgcct ccattggtca gtccaacgcc agagcaatgg    720
cttgaacgtg ccacaagact ggttacgcaa gcaattgctg ataaaaagca gctgcagacc    780
acaaacaata ctcttatcaa gaattcccca accctctag aaagcagaa agccatctac       840
aatggtgagc tacttgtgga tgagatagcc agtctacagg cccgcttagt taagctgaac    900
ggaggaggag gatcaggtga cattttgat atgctgcgcc aagacgaagg cctggacctg      960
aacctgtata agacacggga aggctactgg acgattggta ttggtcagct ggtcaccaaa   1020
aacccgagta agatgtggc acgtgctgaa ctggacaaac tgatgggtcg tgtgtgcaat    1080
ggccgcatta cgatggcgga agccgaacaa ctgtttaacc gtagcgttga aaatgcacgt   1140
cgcgctatcc tgcgcaaccc gaaactgaaa ccggtgtatg atgttctgga cgaagtgcgt   1200
cgctgtgcgc tgatcaacat ggttttcag atgggcgaag cgggtgtcgc cggcttcacc    1260
aatagcctgc gtatgctgca gcaaaaacgc tggaacgatg cggccgtcaa tctggcacag  1320
tctcgctggt acaaacaaac gccgaatcgt gcgaaacgcg ttattgctac cttcaaaacg  1380
ggcacctggg cggcgtatcg ttga                                         1404
```

<210> SEQ ID NO 20
<211> LENGTH: 467
<212> TYPE: PRT
<213> ORGANISM: Artificial Sequence
<220> FEATURE:
<223> OTHER INFORMATION: Protein; Theoretical pI/Mw: 9.05 / 53373.88

<400> SEQUENCE: 20

```
Met Ser Asn Asp Asn Glu Val Pro Gly Ser Met Val Ile Val Ala Gln
1               5                   10                  15

Gly Pro Asp Asp Gln Tyr Ala Tyr Glu Val Pro Pro Ile Asp Ser Ala
            20                  25                  30
```

```
Ala Val Ala Gly Asn Met Phe Gly Asp Leu Ile Gln Arg Glu Ile Tyr
             35                  40                  45

Leu Gln Lys Asn Ile Tyr Tyr Pro Val Arg Ser Ile Phe Glu Gln Gly
     50                  55                  60

Thr Lys Glu Lys Glu Ile Asn Lys Lys Val Ser Asp Gln Val Asp
 65              70                  75                  80

Gly Leu Leu Lys Gln Ile Thr Gln Gly Lys Arg Glu Ala Thr Arg Gln
                 85                  90                  95

Glu Arg Val Asp Val Met Ser Ala Val Leu His Lys Met Glu Ser Asp
             100                 105                 110

Leu Glu Gly Tyr Lys Lys Thr Phe Thr Lys Gly Pro Phe Ile Asp Tyr
             115                 120                 125

Glu Lys Gln Ser Ser Leu Ser Ile Tyr Glu Ala Trp Val Lys Ile Trp
         130                 135                 140

Glu Lys Asn Ser Trp Glu Glu Arg Lys Lys Tyr Pro Phe Gln Gln Leu
145                 150                 155                 160

Val Arg Asp Glu Leu Glu Arg Ala Val Ala Tyr Tyr Lys Gln Asp Ser
                 165                 170                 175

Leu Ser Glu Ala Val Lys Val Leu Arg Gln Glu Leu Asn Lys Gln Lys
             180                 185                 190

Ala Leu Lys Glu Lys Glu Asp Leu Ser Gln Leu Glu Arg Asp Tyr Arg
         195                 200                 205

Thr Arg Lys Ala Asn Leu Glu Met Lys Val Gln Ser Glu Leu Asp Gln
     210                 215                 220

Ala Gly Ser Ala Leu Pro Pro Leu Val Ser Pro Thr Pro Glu Gln Trp
225                 230                 235                 240

Leu Glu Arg Ala Thr Arg Leu Val Thr Gln Ala Ile Ala Asp Lys Lys
                 245                 250                 255

Gln Leu Gln Thr Thr Asn Asn Thr Leu Ile Lys Asn Ser Pro Thr Pro
             260                 265                 270

Leu Glu Lys Gln Lys Ala Ile Tyr Asn Gly Glu Leu Leu Val Asp Glu
         275                 280                 285

Ile Ala Ser Leu Gln Ala Arg Leu Val Lys Leu Asn Gly Gly Gly Gly
     290                 295                 300

Ser Gly Asp Ile Phe Asp Met Leu Arg Gln Asp Glu Gly Leu Asp Leu
305                 310                 315                 320

Asn Leu Tyr Lys Asp Thr Glu Gly Tyr Trp Thr Ile Gly Ile Gly Gln
                 325                 330                 335

Leu Val Thr Lys Asn Pro Ser Lys Asp Val Ala Arg Ala Glu Leu Asp
             340                 345                 350

Lys Leu Met Gly Arg Val Cys Asn Gly Arg Ile Thr Met Ala Glu Ala
         355                 360                 365

Glu Gln Leu Phe Asn Arg Ser Val Glu Asn Ala Arg Arg Ala Ile Leu
     370                 375                 380

Arg Asn Pro Lys Leu Lys Pro Val Tyr Asp Val Leu Asp Glu Val Arg
385                 390                 395                 400

Arg Cys Ala Leu Ile Asn Met Val Phe Gln Met Gly Glu Ala Gly Val
                 405                 410                 415

Ala Gly Phe Thr Asn Ser Leu Arg Met Leu Gln Gln Lys Arg Trp Asn
             420                 425                 430

Asp Ala Ala Val Asn Leu Ala Gln Ser Arg Trp Tyr Lys Gln Thr Pro
         435                 440                 445
```

```
Asn Arg Ala Lys Arg Val Ile Ala Thr Phe Lys Thr Gly Thr Trp Ala
    450                 455                 460

Ala Tyr Arg
465
```

<210> SEQ ID NO 21
<211> LENGTH: 1515
<212> TYPE: DNA
<213> ORGANISM: Artificial Sequence
<220> FEATURE:
<223> OTHER INFORMATION: P638: S5 Pyocin with 6X-His tag: 1497 bases

<400> SEQUENCE: 21

```
atgtccaatg acaacgaagt acctggttcc atggttattg tcgcacaagg tccagacgat      60
caatacgcat acgaggttcc ccctatcgat agcgcggccg ttgccgggaa tatgtttggc     120
gacttaattc aaagagaaat atatctacag aaaaacattt attatccagt ccgatctatt     180
tttgaacaag gaacaaaaga aagaaggag atcaacaaga agtatctga tcaagtcgat       240
ggcttgctaa agcagatcac tcaaggaaaa agggaggcca caaggcaaga gcgagtcgat     300
gtcatgtcgg cagtcctgca caagatggaa tctgatcttg aaggatacaa aaagaccttt     360
accaaaggcc cattcattga ctacgaaaag cagtcaagcc tctccatcta tgaggcctgg     420
gtcaagatct gggagaagaa ctcttgggaa gaaagaaaga agtacccttt tcagcagctt     480
gttagagatg aactggagcg gcggttgcc tactacaaac aagattcact ctctgaagcg     540
gtaaaagtgc taagacagga gctcaacaag caaaaagcgc taaggaaaa agaggacctc     600
tctcaactgg agcgggacta cagaacccga aggcgaatc tcgagatgaa agtacaatcc     660
gagcttgatc aagcgggaag tgctttgcct ccattggtca gtccaacgcc agagcaatgg    720
cttgaacgtg ccacaagact ggttacgcaa gcaattgctg ataaaaagca gctgcagacc    780
acaaacaata ctcttatcaa gaattcccca accctctag aaaagcagaa agccatctac     840
aatggtgagc tacttgtgga tgagatagcc agtctacagg cccgcttagt taagctgaac    900
gccgaaacga cacgacgcag gacagaagca gaacgcaagg cggccgagga caagcgttg    960
caagatgcta ttaaatttac tgccgacttt tataaggaag taactgagaa atttggcgca   1020
cgaacatcgg agatggcgcg ccaactggcc gaaggcgcca ggggaaaaa tatcaggagt   1080
tcggcggaag caatcaagtc gtttgaaaag cacaaggatg cgttaaataa aaaacttagc   1140
cttaaagata ggcaagccat tgccaaagcc tttgattctc tagacaagca gatgatggcg   1200
aagagccttg agaaatttag caaaggcttt ggagttgtag gcaaagctat tgacgccgcc   1260
agcctgtacc aagagttcaa gatatctacg gaaaccgggg actggaaacc attctttgta   1320
aaaattgaaa cactagctgc tggtgcggcc gccagttggc ttgtgggtat tgcatttgcc   1380
acggcaacag ccactcctat aggcattctg gggttcgcac tggtaatggc agttaccggg   1440
gcgatgattg acgaagacct tctagaaaaa gcaaacaatc ttgtaatatc cattcaccac   1500
caccaccacc actaa                                                    1515
```

<210> SEQ ID NO 22
<211> LENGTH: 504
<212> TYPE: PRT
<213> ORGANISM: Artificial Sequence
<220> FEATURE:
<223> OTHER INFORMATION: Theoretical pI/Mw: 8.50 / 56075.04

<400> SEQUENCE: 22

Met Ser Asn Asp Asn Glu Val Pro Gly Ser Met Val Ile Val Ala Gln

-continued

```
1               5                   10                  15
Gly Pro Asp Asp Gln Tyr Ala Tyr Glu Val Pro Pro Ile Asp Ser Ala
                20                  25                  30
Ala Val Ala Gly Asn Met Phe Gly Asp Leu Ile Gln Arg Glu Ile Tyr
                35                  40                  45
Leu Gln Lys Asn Ile Tyr Tyr Pro Val Arg Ser Ile Phe Glu Gln Gly
    50                  55                  60
Thr Lys Glu Lys Lys Glu Ile Asn Lys Lys Val Ser Asp Gln Val Asp
65                  70                  75                  80
Gly Leu Leu Lys Gln Ile Thr Gln Gly Lys Arg Glu Ala Thr Arg Gln
                85                  90                  95
Glu Arg Val Asp Val Met Ser Ala Val Leu His Lys Met Glu Ser Asp
                100                 105                 110
Leu Glu Gly Tyr Lys Lys Thr Phe Thr Lys Gly Pro Phe Ile Asp Tyr
                115                 120                 125
Glu Lys Gln Ser Ser Leu Ser Ile Tyr Glu Ala Trp Val Lys Ile Trp
130                 135                 140
Glu Lys Asn Ser Trp Glu Glu Arg Lys Lys Tyr Pro Phe Gln Gln Leu
145                 150                 155                 160
Val Arg Asp Glu Leu Glu Arg Ala Val Ala Tyr Tyr Lys Gln Asp Ser
                165                 170                 175
Leu Ser Glu Ala Val Lys Val Leu Arg Gln Glu Leu Asn Lys Gln Lys
                180                 185                 190
Ala Leu Lys Glu Lys Glu Asp Leu Ser Gln Leu Glu Arg Asp Tyr Arg
                195                 200                 205
Thr Arg Lys Ala Asn Leu Glu Met Lys Val Gln Ser Glu Leu Asp Gln
                210                 215                 220
Ala Gly Ser Ala Leu Pro Pro Leu Val Ser Pro Thr Pro Glu Gln Trp
225                 230                 235                 240
Leu Glu Arg Ala Thr Arg Leu Val Thr Gln Ala Ile Ala Asp Lys Lys
                245                 250                 255
Gln Leu Gln Thr Thr Asn Asn Thr Leu Ile Lys Asn Ser Pro Thr Pro
                260                 265                 270
Leu Glu Lys Gln Lys Ala Ile Tyr Asn Gly Glu Leu Leu Val Asp Glu
                275                 280                 285
Ile Ala Ser Leu Gln Ala Arg Leu Val Lys Leu Asn Ala Glu Thr Thr
                290                 295                 300
Arg Arg Arg Thr Glu Ala Glu Arg Lys Ala Ala Glu Glu Gln Ala Leu
305                 310                 315                 320
Gln Asp Ala Ile Lys Phe Thr Ala Asp Phe Tyr Lys Glu Val Thr Glu
                325                 330                 335
Lys Phe Gly Ala Arg Thr Ser Glu Met Ala Arg Gln Leu Ala Glu Gly
                340                 345                 350
Ala Arg Gly Lys Asn Ile Arg Ser Ser Ala Glu Ala Ile Lys Ser Phe
                355                 360                 365
Glu Lys His Lys Asp Ala Leu Asn Lys Lys Leu Ser Leu Lys Asp Arg
                370                 375                 380
Gln Ala Ile Ala Lys Ala Phe Asp Ser Leu Asp Lys Gln Met Met Ala
385                 390                 395                 400
Lys Ser Leu Glu Lys Phe Ser Lys Gly Phe Gly Val Val Gly Lys Ala
                405                 410                 415
Ile Asp Ala Ala Ser Leu Tyr Gln Glu Phe Lys Ile Ser Thr Glu Thr
                420                 425                 430
```

```
Gly Asp Trp Lys Pro Phe Phe Val Lys Ile Glu Thr Leu Ala Ala Gly
        435                 440                 445

Ala Ala Ala Ser Trp Leu Val Gly Ile Ala Phe Ala Thr Ala Thr Ala
    450                 455                 460

Thr Pro Ile Gly Ile Leu Gly Phe Ala Leu Val Met Ala Val Thr Gly
465                 470                 475                 480

Ala Met Ile Asp Glu Asp Leu Leu Glu Lys Ala Asn Asn Leu Val Ile
                485                 490                 495

Ser Ile His His His His His His
        500

<210> SEQ ID NO 23
<211> LENGTH: 1497
<212> TYPE: DNA
<213> ORGANISM: Artificial Sequence
<220> FEATURE:
<223> OTHER INFORMATION: P652: S5 Pyocin without His tag: 1497 bases

<400> SEQUENCE: 23
atgtccaatg acaacgaagt acctggttcc atggttattg tcgcacaagg tccagacgat     60
caatacgcat acgaggttcc ccctatcgat agcgcggccg ttgccgggaa tatgtttggc    120
gacttaattc aaagagaaat atatctacag aaaaacattt attatccagt ccgatctatt    180
tttgaacaag gaacaaaaga aagaaggag atcaacaaga agtatctga tcaagtcgat    240
ggcttgctaa agcagatcac tcaaggaaaa agggaggcca aaggcaaga gcgagtcgat    300
gtcatgtcgg cagtcctgca caagatgaa tctgatcttg aaggatacaa aaagaccttt    360
accaaaggcc cattcattga ctacgaaaag cagtcaagcc tctccatcta tgaggcctgg    420
gtcaagatct gggagaagaa ctcttgggaa gaaagaaaga agtacccttt tcagcagctt    480
gttagagatg aactggagcg ggcggttgcc tactacaaac aagattcact ctctgaagcg    540
gtaaaagtgc taagacagga gctcaacaag caaaaagcgc taaaggaaaa agaggacctc    600
tctcaactgg agcgggacta cagaacccga aaggcgaatc tcgagatgaa agtacaatcc    660
gagcttgatc aagcgggaag tgctttgcct ccattggtca gtccaacgcc agagcaatgg    720
cttgaacgtg ccacaagact ggttacgcaa gcaattgctg ataaaaagca gctgcagacc    780
acaaacaata ctcttatcaa gaattcccca ccccctctag aaaagcagaa agccatctac    840
aatggtgagc tacttgtgga tgagatagcc agtctacagg cccgcttagt taagctgaac    900
gccgaaacga cacgacgcag acagaagca gaacgcaagg cggccgagga caagcgttg    960
caagatgcta ttaaatttac tgccgacttt tataaggaag taactgagaa atttggcgca   1020
cgaacatcgg agatggcgcg ccaactggcc gaaggcgcca gggggaaaaa tatcaggagt   1080
tcggcggaag caatcaagtc gtttgaaaag cacaaggatg cgttaaataa aaaacttagc   1140
cttaaagata ggcaagccat tgccaaagcc tttgattctc tagacaagca gatgatggcg   1200
aagagccttg agaaatttag caaaggcttt ggagttgtag caaagctat tgacgccgcc   1260
agcctgtacc aagagttcaa gatatctacg gaaaccgggg actggaaacc attctttgta   1320
aaaattgaaa cactagctgc tggtgcggcc gccagttggc ttgtgggtat tgcatttgcc   1380
acggcaacag ccactcctat aggcattctg gggttcgcac tggtaatggc agttaccggg   1440
gcgatgattg acgaagacct tctagaaaaa gcaaacaatc ttgtaatatc catttaa     1497

<210> SEQ ID NO 24
<211> LENGTH: 498
```

<212> TYPE: PRT
<213> ORGANISM: Artificial Sequence
<220> FEATURE:
<223> OTHER INFORMATION: Theoretical pI/Mw: 8.50 / 56075.04

<400> SEQUENCE: 24

| | | | | | | | | | | | | | | | |
|---|---|---|---|---|---|---|---|---|---|---|---|---|---|---|---|
| Met | Ser | Asn | Asp | Asn | Glu | Val | Pro | Gly | Ser | Met | Val | Ile | Val | Ala | Gln |
| 1 | | | | 5 | | | | | 10 | | | | | 15 | |
| Gly | Pro | Asp | Asp | Gln | Tyr | Ala | Tyr | Glu | Val | Pro | Pro | Ile | Asp | Ser | Ala |
| | | | 20 | | | | | 25 | | | | | 30 | | |
| Ala | Val | Ala | Gly | Asn | Met | Phe | Gly | Asp | Leu | Ile | Gln | Arg | Glu | Ile | Tyr |
| | | 35 | | | | | 40 | | | | | 45 | | | |
| Leu | Gln | Lys | Asn | Ile | Tyr | Tyr | Pro | Val | Arg | Ser | Ile | Phe | Glu | Gln | Gly |
| | 50 | | | | | 55 | | | | | 60 | | | | |
| Thr | Lys | Glu | Lys | Lys | Glu | Ile | Asn | Lys | Val | Ser | Asp | Gln | Val | Asp | |
| 65 | | | | | 70 | | | | | 75 | | | | | 80 |
| Gly | Leu | Leu | Lys | Gln | Ile | Thr | Gln | Gly | Lys | Arg | Glu | Ala | Thr | Arg | Gln |
| | | | | 85 | | | | | 90 | | | | | 95 | |
| Glu | Arg | Val | Asp | Val | Met | Ser | Ala | Val | Leu | His | Lys | Met | Glu | Ser | Asp |
| | | | 100 | | | | | 105 | | | | | 110 | | |
| Leu | Glu | Gly | Tyr | Lys | Lys | Thr | Phe | Thr | Lys | Gly | Pro | Phe | Ile | Asp | Tyr |
| | | | 115 | | | | | 120 | | | | | 125 | | |
| Glu | Lys | Gln | Ser | Ser | Leu | Ser | Ile | Tyr | Glu | Ala | Trp | Val | Lys | Ile | Trp |
| | 130 | | | | | 135 | | | | | 140 | | | | |
| Glu | Lys | Asn | Ser | Trp | Glu | Glu | Arg | Lys | Lys | Tyr | Pro | Phe | Gln | Gln | Leu |
| 145 | | | | | 150 | | | | | 155 | | | | | 160 |
| Val | Arg | Asp | Glu | Leu | Glu | Arg | Ala | Val | Ala | Tyr | Tyr | Lys | Gln | Asp | Ser |
| | | | | 165 | | | | | 170 | | | | | 175 | |
| Leu | Ser | Glu | Ala | Val | Lys | Val | Leu | Arg | Gln | Glu | Leu | Asn | Lys | Gln | Lys |
| | | | 180 | | | | | 185 | | | | | 190 | | |
| Ala | Leu | Lys | Glu | Lys | Glu | Asp | Leu | Ser | Gln | Leu | Glu | Arg | Asp | Tyr | Arg |
| | | 195 | | | | | 200 | | | | | 205 | | | |
| Thr | Arg | Lys | Ala | Asn | Leu | Glu | Met | Lys | Val | Gln | Ser | Glu | Leu | Asp | Gln |
| | 210 | | | | | 215 | | | | | 220 | | | | |
| Ala | Gly | Ser | Ala | Leu | Pro | Pro | Leu | Val | Ser | Pro | Thr | Pro | Glu | Gln | Trp |
| 225 | | | | | 230 | | | | | 235 | | | | | 240 |
| Leu | Glu | Arg | Ala | Thr | Arg | Leu | Val | Thr | Gln | Ala | Ile | Ala | Asp | Lys | Lys |
| | | | | 245 | | | | | 250 | | | | | 255 | |
| Gln | Leu | Gln | Thr | Thr | Asn | Asn | Thr | Leu | Ile | Lys | Asn | Ser | Pro | Thr | Pro |
| | | | 260 | | | | | 265 | | | | | 270 | | |
| Leu | Glu | Lys | Gln | Lys | Ala | Ile | Tyr | Asn | Gly | Glu | Leu | Leu | Val | Asp | Glu |
| | | 275 | | | | | 280 | | | | | 285 | | | |
| Ile | Ala | Ser | Leu | Gln | Ala | Arg | Leu | Val | Lys | Leu | Asn | Ala | Glu | Thr | Thr |
| | 290 | | | | | 295 | | | | | 300 | | | | |
| Arg | Arg | Arg | Thr | Glu | Ala | Glu | Arg | Lys | Ala | Ala | Glu | Glu | Gln | Ala | Leu |
| 305 | | | | | 310 | | | | | 315 | | | | | 320 |
| Gln | Asp | Ala | Ile | Lys | Phe | Thr | Ala | Asp | Phe | Tyr | Lys | Glu | Val | Thr | Glu |
| | | | | 325 | | | | | 330 | | | | | 335 | |
| Lys | Phe | Gly | Ala | Arg | Thr | Ser | Glu | Met | Ala | Arg | Gln | Leu | Ala | Glu | Gly |
| | | | 340 | | | | | 345 | | | | | 350 | | |
| Ala | Arg | Gly | Lys | Asn | Ile | Arg | Ser | Ser | Ala | Glu | Ala | Ile | Lys | Ser | Phe |
| | | 355 | | | | | 360 | | | | | 365 | | | |
| Glu | Lys | His | Lys | Asp | Ala | Leu | Asn | Lys | Lys | Leu | Ser | Leu | Lys | Asp | Arg |
| | 370 | | | | | 375 | | | | | 380 | | | | |

-continued

```
Gln Ala Ile Ala Lys Ala Phe Asp Ser Leu Asp Lys Gln Met Met Ala
385                 390                 395                 400

Lys Ser Leu Glu Lys Phe Ser Lys Gly Phe Gly Val Val Gly Lys Ala
            405                 410                 415

Ile Asp Ala Ala Ser Leu Tyr Gln Glu Phe Lys Ile Ser Thr Glu Thr
        420                 425                 430

Gly Asp Trp Lys Pro Phe Phe Val Lys Ile Glu Thr Leu Ala Ala Gly
    435                 440                 445

Ala Ala Ala Ser Trp Leu Val Gly Ile Ala Phe Ala Thr Ala Thr Ala
        450                 455                 460

Thr Pro Ile Gly Ile Leu Gly Phe Ala Leu Val Met Ala Val Thr Gly
465                 470                 475                 480

Ala Met Ile Asp Glu Asp Leu Leu Glu Lys Ala Asn Asn Leu Val Ile
                485                 490                 495

Ser Ile
```

<210> SEQ ID NO 25
<211> LENGTH: 990
<212> TYPE: DNA
<213> ORGANISM: Artificial Sequence
<220> FEATURE:
<223> OTHER INFORMATION: Fyu A BD- T4 lysozyme fusion

<400> SEQUENCE: 25

```
atgagcgaca cgatggttgt gaatggcagc ggcggcgttc cggcgttcct gtttagcggc      60
agcaccctga gcagctatcg tccgaatttc gaggcgaaca gcatcaccat tgcgctgccg     120
cactatgtgg acctgccggg ccgtagcaac ttcaagctga tgtatatcat gggttttccg     180
attgacaccg agatggaaaa ggatagcgag tacagcaaca aaatccgtca agaaagcaag     240
attagcaaaa ccgagggcac cgtgagctac gaacagaaaa tcaccgttga gaccggccaa     300
gaaaaggatg gtgtgaaagt ttatcgtgtg atggttctgg agggcaccat cgcggagagc     360
attgaacacc tggacaagaa agagaacgaa gacatcctga caacaaccg taaccgtatt     420
gtgctggcgg acaacaccgt tatcaacttc gataacatta gccagctgaa ggaatttctg     480
cgtcgtagcg tgaacatcgt tattttcgag atgctgcgta tcgacgaacg tctgcgtctg     540
aagatttata aagataccga gggctactat accatcggta ttggccacct gctgaccaaa     600
agcccgagcc tgaacgcggc gaagagcgaa ctggacaaag cgatcggccg taactgcaac     660
ggtgtgatta ccaaggatga gcggaaaaa ctgtttaacc aggacgtgga tgcggcggtt     720
cgtggtatcc tgcgtaacgc gaagctgaaa ccggtgtacg acagcctgga tgcggttcgt     780
cgttgcgcgc tgattaacat ggtgttccaa atgggcgaga ccggcgttgc gggttttacc     840
aacagcctgc gtatgctgca gcaaaagcgt tgggacgaag cggcggttaa cctggcgaaa     900
agcatctggt ataaccagac cccgaaccgt gcgaaacgtg tgattaccac cttccgtacc     960
ggcacctggg atgcgtataa aaacctgtaa                                       990
```

<210> SEQ ID NO 26
<211> LENGTH: 329
<212> TYPE: PRT
<213> ORGANISM: Artificial Sequence
<220> FEATURE:
<223> OTHER INFORMATION: Amino acid sequence encoded by SEQ ID NO: 25

<400> SEQUENCE: 26

```
Met Ser Asp Thr Met Val Val Asn Gly Ser Gly Gly Val Pro Ala Phe
1               5                   10                  15
```

```
Leu Phe Ser Gly Ser Thr Leu Ser Ser Tyr Arg Pro Asn Phe Glu Ala
             20                  25                  30

Asn Ser Ile Thr Ile Ala Leu Pro His Tyr Val Asp Leu Pro Gly Arg
         35                  40                  45

Ser Asn Phe Lys Leu Met Tyr Ile Met Gly Phe Pro Ile Asp Thr Glu
 50                  55                  60

Met Glu Lys Asp Ser Glu Tyr Ser Asn Lys Ile Arg Gln Glu Ser Lys
 65                  70                  75                  80

Ile Ser Lys Thr Glu Gly Thr Val Ser Tyr Glu Gln Lys Ile Thr Val
             85                  90                  95

Glu Thr Gly Gln Glu Lys Asp Gly Val Lys Val Tyr Arg Val Met Val
            100                 105                 110

Leu Glu Gly Thr Ile Ala Glu Ser Ile Glu His Leu Asp Lys Lys Glu
            115                 120                 125

Asn Glu Asp Ile Leu Asn Asn Arg Asn Arg Ile Val Leu Ala Asp
            130                 135                 140

Asn Thr Val Ile Asn Phe Asp Asn Ile Ser Gln Leu Lys Glu Phe Leu
145                 150                 155                 160

Arg Arg Ser Val Asn Ile Val Ile Phe Glu Met Leu Arg Ile Asp Glu
                165                 170                 175

Arg Leu Arg Leu Lys Ile Tyr Lys Asp Thr Glu Gly Tyr Tyr Thr Ile
            180                 185                 190

Gly Ile Gly His Leu Leu Thr Lys Ser Pro Ser Leu Asn Ala Ala Lys
            195                 200                 205

Ser Glu Leu Asp Lys Ala Ile Gly Arg Asn Cys Asn Gly Val Ile Thr
210                 215                 220

Lys Asp Glu Ala Glu Lys Leu Phe Asn Gln Asp Val Asp Ala Ala Val
225                 230                 235                 240

Arg Gly Ile Leu Arg Asn Ala Lys Leu Lys Pro Val Tyr Asp Ser Leu
                245                 250                 255

Asp Ala Val Arg Arg Cys Ala Leu Ile Asn Met Val Phe Gln Met Gly
            260                 265                 270

Glu Thr Gly Val Ala Gly Phe Thr Asn Ser Leu Arg Met Leu Gln Gln
            275                 280                 285

Lys Arg Trp Asp Glu Ala Val Asn Leu Ala Lys Ser Ile Trp Tyr
290                 295                 300

Asn Gln Thr Pro Asn Arg Ala Lys Arg Val Ile Thr Thr Phe Arg Thr
305                 310                 315                 320

Gly Thr Trp Asp Ala Tyr Lys Asn Leu
            325

<210> SEQ ID NO 27
<211> LENGTH: 1152
<212> TYPE: DNA
<213> ORGANISM: Artificial Sequence
<220> FEATURE:
<223> OTHER INFORMATION: Fyu A BD -GP36 fusion

<400> SEQUENCE: 27 atgagc

```
attagcaaaa ccgagggcac cgtgagctac gaacagaaaa tcaccgttga gaccggccaa      300
gaaaaggatg gtgtgaaagt ttatcgtgtg atggttctgg agggcaccat cgcggagagc      360
attgaacacc tggacaagaa agagaacgaa gacatcctga caacaaccg taaccgtatt       420 gtgctggcgg acaacaccgt tatcaacttc gataacatta gccagctgaa ggaatttctg      480
cgtcgtagcg tgaacatcgt tggtgtggcc ctggaccgca cgcgggttga tccccaggca      540
gtcggcaacg aggtgctcaa gcgcaacgcg gataagctga atgcgatgcg gggcgccgag      600
tacggtgcca acgtcaaggt cagcggcacg gacattcgca tgaacggggg taacagtgcc      660
ggcatgctga agcaggacgt gttcaactgg cggaaggaac tggctcagtt cgaggcttac      720
cgaggggagg cgtataagga tgccgatggt tatagtgtgg gcctggggca ttacctgggc      780
agtggcaatg ctggggcagg tactacagtc acgcctgagc aagccgcgca gtggttcgcc      840
gaggacaccg accgcgcact cgaccagggt gtgaggttgg ccgacgagct gggcgttacg      900
aacaatgcct ctatcctggg attggccggt atggccttcc agatgggcga aggacgtgcc      960
cggcagttcc gtaacacctt ccaggcgatc aaggatcgca caaggaagc cttcgaggct     1020 ggtgtgcgaa acagcaagtg gtacacgcag acgcccaacc gggccgaggc attcatcaag     1080
cgcatggcgc cccacttcga taccgagtc caaatcggtg tcgattggta cagcgccgca     1140
acagcggagt ga                                                         1152
```

<210> SEQ ID NO 28
<211> LENGTH: 383
<212> TYPE: PRT
<213> ORGANISM: Artificial Sequence
<220> FEATURE:
<223> OTHER INFORMATION: Amino acid sequence encoded by SEQ ID NO: 27

<400> SEQUENCE: 28

Met Ser Asp Thr Met Val Val Asn Gly Ser Gly Val Pro Ala Phe
1               5                   10                  15

Leu Phe Ser Gly Ser Thr Leu Ser Ser Tyr Arg Pro Asn Phe Glu Ala
            20                  25                  30

Asn Ser Ile Thr Ile Ala Leu Pro His Tyr Val Asp Leu Pro Gly Arg
        35                  40                  45

Ser Asn Phe Lys Leu Met Tyr Ile Met Gly Phe Pro Ile Asp Thr Glu
    50                  55                  60

Met Glu Lys Asp Ser Glu Tyr Ser Asn Lys Ile Arg Gln Glu Ser Lys
65                  70                  75                  80

Ile Ser Lys Thr Glu Gly Thr Val Ser Tyr Glu Gln Lys Ile Thr Val
                85                  90                  95

Glu Thr Gly Gln Glu Lys Asp Gly Val Lys Val Tyr Arg Val Met Val
            100                 105                 110

Leu Glu Gly Thr Ile Ala Glu Ser Ile Glu His Leu Asp Lys Lys Glu
        115                 120                 125

Asn Glu Asp Ile Leu Asn Asn Arg Asn Arg Ile Val Leu Ala Asp
    130                 135                 140

Asn Thr Val Ile Asn Phe Asp Asn Ile Ser Gln Leu Lys Glu Phe Leu
145                 150                 155                 160

Arg Arg Ser Val Asn Ile Val Gly Val Ala Leu Asp Arg Thr Arg Val
                165                 170                 175

Asp Pro Gln Ala Val Gly Asn Glu Val Leu Lys Arg Asn Ala Asp Lys
            180                 185                 190

Leu Asn Ala Met Arg Gly Ala Glu Tyr Gly Ala Asn Val Lys Val Ser

```
              195                 200                 205
Gly Thr Asp Ile Arg Met Asn Gly Gly Asn Ser Ala Gly Met Leu Lys
    210                 215                 220

Gln Asp Val Phe Asn Trp Arg Lys Glu Leu Ala Gln Phe Glu Ala Tyr
225                 230                 235                 240

Arg Gly Glu Ala Tyr Lys Asp Ala Asp Gly Tyr Ser Val Gly Leu Gly
                245                 250                 255

His Tyr Leu Gly Ser Gly Asn Ala Gly Ala Gly Thr Thr Val Thr Pro
            260                 265                 270

Glu Gln Ala Ala Gln Trp Phe Ala Glu Asp Thr Asp Arg Ala Leu Asp
        275                 280                 285

Gln Gly Val Arg Leu Ala Asp Glu Leu Gly Val Thr Asn Asn Ala Ser
    290                 295                 300

Ile Leu Gly Leu Ala Gly Met Ala Phe Gln Met Gly Glu Gly Arg Ala
305                 310                 315                 320

Arg Gln Phe Arg Asn Thr Phe Gln Ala Ile Lys Asp Arg Asn Lys Glu
                325                 330                 335

Ala Phe Glu Ala Gly Val Arg Asn Ser Lys Trp Tyr Thr Gln Thr Pro
            340                 345                 350

Asn Arg Ala Glu Ala Phe Ile Lys Arg Met Ala Pro His Phe Asp Thr
        355                 360                 365

Pro Ser Gln Ile Gly Val Asp Trp Tyr Ser Ala Thr Ala Glu
    370                 375                 380

<210> SEQ ID NO 29
<211> LENGTH: 1955
<212> TYPE: DNA
<213> ORGANISM: Artificial Sequence
<220> FEATURE:
<223> OTHER INFORMATION: pelB-FyuA receptor: 2028 bases

<400> SEQUENCE: 29
atgaaatacc tgctgccgac cgctgctgct ggtctgctgc tcctcgctgc ccagccggcg      60
atggccatgg ccagacttc acagcaagac gaaagcacgc tggtggttac cgccagtaaa     120
caatcttccc gctcggcatc agccaacaac gtctcgtcta ctgttgtcag cgcgccggaa     180
ttaagcgacg ccggcgtcac cgccagcgac aaactcccca gagtcttgcc cgggctcaat     240
attgaaaata gcgcaacat gcttttttcg acgatctcgc tacgcggcgt ctcttcagcg     300
caggacttct ataccccgc cgtcaccctg tatgtcgatg gcgtccctca gctttccacc     360
aacaccatcc aggcgcttac cgatgtgcaa agcgtggagt gctgcgagg cccacaggga     420 acgttatatg gcaaaagcgc tcagggcggg atcatcaaca tcgtcaccca gcagccggac     480
agcacgccgc gcggctatat tgaaggcggc gtcagtagcc gcgacagtta tcgaagtaag     540
ttcaacctga gcggccccat tcaggatggc ctgctgtacg gcagcgtcac cctgttacgc     600
caggttgatg acgcgacat gattaacccc gcgacgggaa gcgatgactt aggcggcacc     660
cgcgccagca tagggaatgt gaaactgcgt ctggcgccgg acgatcagcc ctgggaaatg     720
ggctttgccg cctcacgcga atgtaccccgc gccacccagg acgcctatgt gggatggaat     780
gatattaagg ccgtaagct gtcgatcagc atggttcac cagacccgta catgcggcgc     840
tgcactgaca gccagaccct gagtgggaaa tacaccaccg atgactgggt tttcaacctg     900
atcagcgcct ggcagcagca gcattattcg cgcaccttcc cttccggttc gttaatcgtc     960
aatatgcctc agcgctggaa tcaggatgtg caggagctgc gcgccgcaac cctgggcgat    1020
```

```
gcgcgtaccg ttgatatggt gtttgggctg taccggcaga acacccgcga aagtttaaat    1080
tcagcctacg acatgccgac aatgccttat ttaagcagta ccggctatac caccgctgaa    1140
acgctggccg catacagtga cctgacctgg catttaaccg atcgttttga tatcggcggc    1200
ggcgtgcgct tctcgcatga taaatccagt acacaatatc acggcagcat gctcggcaac    1260
ccgtttggcg accagggtaa gagcaatgac gatcaggtgc tcgggcagct atccgcaggc    1320
tatatgctga ccgatgactg gagagtgtat acccgtgtag cccagggata taaaccttcc    1380
gggtacaaca tcgtgcctac tgcgggtctt gatgccaaac cgttcgtcgc cgagaaatcc    1440
atcaactatg aacttggcac ccgctacgaa accgctgacg tcacgctgca agccgcgacg    1500
ttttataccc acaccaaaga catgcagctt tactctggcc cggtcgggat gcagacatta    1560
agcaatgcgg gtaaagccga cgccaccggc gttgagcttg aagcgaagtg gcggtttgcg    1620
ccaggctggt catgggatat caatggcaac gtgatccgtt ccgaattcac caatgacagt    1680
gagttgtatc acggtaaccg ggtgccgttc gtaccacgtt atggcgcggg aagcagcgtg    1740
aacggtgtga ttgatacgcg ctatggcgca ctgatgcccc gactggcggt taatctggtc    1800
gggccgcatt atttcgatgg cgacaaccag ttgcggcaag gcacctatgc cacccctggac   1860 agcagcctgg gctggcaggc aacggcagca gcgccgtcgc gcaggtcaat atgggtcgca    1920
ccgtcggtat caatacgcga attgatttct tctga                               1955
```

<210> SEQ ID NO 30
<211> LENGTH: 675
<212> TYPE: PRT
<213> ORGANISM: Artificial Sequence
<220> FEATURE:
<223> OTHER INFORMATION: Theoretical pI/Mw: 5.35 / 73772.10

<400> SEQUENCE: 30

```
Met Lys Tyr Leu Leu Pro Thr Ala Ala Ala Gly Leu Leu Leu Leu Ala
1               5                   10                  15

Ala Gln Pro Ala Met Ala Met Gly Gln Thr Ser Gln Gln Asp Glu Ser
            20                  25                  30

Thr Leu Val Val Thr Ala Ser Lys Gln Ser Ser Arg Ser Ala Ser Ala
        35                  40                  45

Asn Asn Val Ser Ser Thr Val Val Ser Ala Pro Glu Leu Ser Asp Ala
    50                  55                  60

Gly Val Thr Ala Ser Asp Lys Leu Pro Arg Val Leu Pro Gly Leu Asn
65                  70                  75                  80

Ile Glu Asn Ser Gly Asn Met Leu Phe Ser Thr Ile Ser Leu Arg Gly
                85                  90                  95

Val Ser Ser Ala Gln Asp Phe Tyr Asn Pro Ala Val Thr Leu Tyr Val
            100                 105                 110

Asp Gly Val Pro Gln Leu Ser Thr Asn Thr Ile Gln Ala Leu Thr Asp
        115                 120                 125

Val Gln Ser Val Glu Leu Leu Arg Gly Pro Gln Gly Thr Leu Tyr Gly
    130                 135                 140

Lys Ser Ala Gln Gly Gly Ile Ile Asn Ile Val Thr Gln Gln Pro Asp
145                 150                 155                 160

Ser Thr Pro Arg Gly Tyr Ile Glu Gly Gly Val Ser Ser Arg Asp Ser
                165                 170                 175

Tyr Arg Ser Lys Phe Asn Leu Ser Gly Pro Ile Gln Asp Gly Leu Leu
            180                 185                 190

Tyr Gly Ser Val Thr Leu Leu Arg Gln Val Asp Asp Gly Asp Met Ile
```

```
              195                 200                 205
Asn Pro Ala Thr Gly Ser Asp Asp Leu Gly Gly Thr Arg Ala Ser Ile
210                 215                 220

Gly Asn Val Lys Leu Arg Leu Ala Pro Asp Asp Gln Pro Trp Glu Met
225                 230                 235                 240

Gly Phe Ala Ala Ser Arg Glu Cys Thr Arg Ala Thr Gln Asp Ala Tyr
                245                 250                 255

Val Gly Trp Asn Asp Ile Lys Gly Arg Lys Leu Ser Ile Ser Asp Gly
                260                 265                 270

Ser Pro Asp Pro Tyr Met Arg Arg Cys Thr Asp Ser Gln Thr Leu Ser
            275                 280                 285

Gly Lys Tyr Thr Thr Asp Asp Trp Val Phe Asn Leu Ile Ser Ala Trp
            290                 295                 300

Gln Gln Gln His Tyr Ser Arg Thr Phe Pro Ser Gly Ser Leu Ile Val
305                 310                 315                 320

Asn Met Pro Gln Arg Trp Asn Gln Asp Val Gln Glu Leu Arg Ala Ala
                325                 330                 335

Thr Leu Gly Asp Ala Arg Thr Val Asp Met Val Phe Gly Leu Tyr Arg
                340                 345                 350

Gln Asn Thr Arg Glu Lys Leu Asn Ser Ala Tyr Asp Met Pro Thr Met
            355                 360                 365

Pro Tyr Leu Ser Ser Thr Gly Tyr Thr Thr Ala Glu Thr Leu Ala Ala
370                 375                 380

Tyr Ser Asp Leu Thr Trp His Leu Thr Asp Arg Phe Asp Ile Gly Gly
385                 390                 395                 400

Gly Val Arg Phe Ser His Asp Lys Ser Ser Thr Gln Tyr His Gly Ser
                405                 410                 415

Met Leu Gly Asn Pro Phe Gly Asp Gln Gly Lys Ser Asn Asp Asp Gln
                420                 425                 430

Val Leu Gly Gln Leu Ser Ala Gly Tyr Met Leu Thr Asp Asp Trp Arg
            435                 440                 445

Val Tyr Thr Arg Val Ala Gln Gly Tyr Lys Pro Ser Gly Tyr Asn Ile
450                 455                 460

Val Pro Thr Ala Gly Leu Asp Ala Lys Pro Phe Val Ala Glu Lys Ser
465                 470                 475                 480

Ile Asn Tyr Glu Leu Gly Thr Arg Tyr Glu Thr Ala Asp Val Thr Leu
                485                 490                 495

Gln Ala Ala Thr Phe Tyr Thr His Thr Lys Asp Met Gln Leu Tyr Ser
                500                 505                 510

Gly Pro Val Gly Met Gln Thr Leu Ser Asn Ala Gly Lys Ala Asp Ala
            515                 520                 525

Thr Gly Val Glu Leu Glu Ala Lys Trp Arg Phe Ala Pro Gly Trp Ser
            530                 535                 540

Trp Asp Ile Asn Gly Asn Val Ile Arg Ser Glu Phe Thr Asn Asp Ser
545                 550                 555                 560

Glu Leu Tyr His Gly Asn Arg Val Pro Phe Val Pro Arg Tyr Gly Ala
                565                 570                 575

Gly Ser Ser Val Asn Gly Val Ile Asp Thr Arg Tyr Gly Ala Leu Met
                580                 585                 590

Pro Arg Leu Ala Val Asn Leu Val Gly Pro His Tyr Phe Asp Gly Asp
            595                 600                 605

Asn Gln Leu Arg Gln Gly Thr Tyr Ala Thr Leu Asp Ser Ser Leu Gly
            610                 615                 620
```

Trp Gln Ala Thr Glu Arg Met Asn Ile Ser Val Tyr Val Asp Asn Leu
625                 630                 635                 640

Phe Asp Arg Arg Tyr Arg Thr Tyr Gly Tyr Met Asn Gly Ser Ser Ala
            645                 650                 655

Val Ala Gln Val Asn Met Gly Thr Val Gly Ile Asn Thr Arg Ile
            660                 665                 670

Asp Phe Phe
        675

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Trp Val Arg Val Arg Arg Trp Val Arg Arg Val Val Arg
1               5                   10                  15

Val Val Arg Arg Trp Val Arg Arg
            20

<210> SEQ ID NO 32
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

His Ala Glu His Lys Val Lys Ile Gly Val Glu Gln Lys Tyr Gly Gln
1               5                   10                  15

Phe Pro Gln Gly Thr Glu Val Thr Tyr Thr Cys Ser Gly Asn Tyr Phe
            20                  25                  30

Leu Met

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Lys Lys Thr Arg Lys Arg Leu Lys Lys Ile Gly Lys Val Leu Lys
1               5                   10                  15

Trp Ile

<210> SEQ ID NO 35
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Trp Lys Leu Phe Lys Lys Ile Gly Ile Gly Ala Val Leu Lys Val
1               5                   10                  15

Leu Thr Thr Gly Leu Pro Ala Leu Ile Ser
            20                  25

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Arg Arg Arg Ser Val Gln Trp Cys Ala
1               5                   10

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Leu Arg Trp Pro Trp Trp Pro Trp Arg Arg Lys
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Cys Trp Tyr Val Cys Tyr Arg Asn Gly Val Arg Val Cys Tyr

Arg Arg Cys Asn
        20

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Asp Ser Ser Ile Arg Val Gln Gly Arg Trp Lys Val Arg Ala Ser
1               5                   10                  15

Phe Phe Lys Leu Gln Gly Ser Phe Asp Val Ser Val Lys Gly
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Pro Arg Arg Arg Arg Ser Ser Ser Arg Pro Val Arg Arg Arg Arg Arg
1               5                   10                  15

Pro Arg Val Ser Arg Arg Arg Arg Arg Gly Gly Arg Arg Arg Arg
            20                  25                  30

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Asn Asn Arg Pro Val Tyr Ile Pro Gln Pro Arg Pro Pro His Pro
1               5                   10                  15

Arg Leu

<210> SEQ ID NO 43
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 44
<211> LENGTH: 18
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 44

Arg Gly Leu Arg Arg Leu Gly Arg Lys Ile Ala His Gly Val Lys Lys
1               5                   10                  15

Tyr Gly
```

THERAPEUTIC BACTERIOCINS

SEQUENCE LISTING

The instant application contains a Sequence Listing which has been submitted electronically in ASCII format and is hereby incorporated by reference in its entirety. Said ASCII copy, created on Feb. 10, 2022, is named 105995-1198187-002410US_SL.txt and is 111,558 bytes in size.

FIELD OF INVENTION

The present invention provides methods and compositions to reduce growth of microbial colonies, including infections, and includes antimicrobial compositions, which may be therapeutic, methods for treatment of infections, and methods for identifying additional such compositions.

BACKGROUND OF THE INVENTION

Bacteria are ubiquitous, ecologically diverse, and find unusual niches for survival. They are present throughout the environment, e.g., soil, dust, water, and on virtually all surfaces. Many are normal and beneficial strains, which provide a synergistic relationship with hosts. Others are harmful, or cause problems along with benefits.

Pathogenic bacteria can cause infectious diseases in humans, other animals, and plants. Some bacteria can only infect or cause problems for a particular host, while others have a broader host specificity, and can cause trouble in a number of hosts. Diseases caused by bacteria are almost as diverse as the bacteria themselves, e.g., food poisoning, tooth decay, anthrax, general infectious diseases, and even certain forms of cancer.

Certain bacteria are normally innocuous, but become pathogenic at the appropriate opportunity, or become problematic upon introduction to an abnormal site or situation. Persons lacking effective immune systems are most vulnerable, and certain bacteria use weakened hosts to proliferate and disperse throughout the population.

Statistically, infectious diseases are a major medical problem. See, e.g., Watstein and Jovanovic (2003) *Statistical Handbook on Infectious Diseases* Greenwood. In the U.S., some 40-70K deaths result from bloodstream nosocomial (hospital derived) infections each year.

Antibiotics have revolutionized clinical medicine over the last half century. Since the original discovery of antibiotic phenomenon, the mechanism of action and development of this class of remarkable therapeutic entities has made enormous progress. See, e.g., Therrien and Levesque (2000) *FEMS Microbiol Rev.* 24:251-62; Durgess (1999) *Chest* 115(3 Suppl):19S-23S; Medeiros (1997) *Clin. Infect. Dis.* 24(Suppl 1):519-45; Jones (1996) *Am. J. Med.* 100(6A):3S-12S; Ford and Hait (1993) *Cytotechnology* 12(1-3):171-212; and Liu (1992) *Compr Ther.* 18:35-42. Antibiotics had about $32B worldwide sales in 2002.

Yet the widespread appearance of antibiotic-resistant bacteria has emphasized the vulnerability of current antimicrobial treatments to bacterial adaptation. See, e.g., Walsh (1992) *Antibiotics: Actions, Origins, Resistance Amer. Soc. Microbiol.*, (1992); Cunha (1992) *Antibiotic Essentials* (Physicians Press); Amyes (2003) *Magic Bullets, Lost Horizons: The Rise and Fall of Antibiotics* (Taylor & Francis); Axelsen (2001) *Essentials of Antimicrobial Pharmacology: A Guide to Fundamentals for Practice* (Humana Press); and Mainous and Pomeroy (eds. 2001) *Management of Antimicrobials in Infectious Diseases: Impact of Antibiotic Resistance* (Humana Press). Recently, the discovery of a highly worrying multiple resistance plasmid NDM-1 has been reported (Kumarasamy et al. (2010) *Lancet Infectious Diseases* 10: 597-602; and Walsh et al. (2011) *Lancet Infectious Diseases*, Early Online Publication, 7 Apr. 2011, doi: 10.1016/S1473-3099(11)70059-7).

Thus, improved methods for decreasing target bacterial growth or survival or limiting bacterial pathogenicity find great utility, especially for antibiotic resistant bacteria, which are most commonly Gram-negative. Antimicrobial effects are applicable to environmental, local, topical, and particularly in vivo colonization. The present invention addresses these and other significant issues.

BRIEF SUMMARY OF THE INVENTION

The present invention is based, in part, upon the recognition that bacteriocins, which may be naturally found proteins, possess particular features and functions which can be used to target certain host bacteria under appropriate situations. Of particular interest are those that target host bacteria in the group of Gram-negative bacteria.

In certain embodiments of the invention, bacteriocins of natural sequence, e.g., bacteriocins or parts thereof, are identified which possess combinations of desired properties to be used to kill or label the target hosts. In other embodiments, certain chimeric bacteriocin constructs are prepared, in which heterologous domains are combined to provide the desired function and/or specificity. In these embodiments, components are substituted in the polypeptide which similarly can achieve or improve on these desired properties, e.g., replacing or substituting components found on bacteriocins.

Gram-negative bacteria are characterized by a thin peptidoglycan cell wall surrounded by an outer membrane, which is lacking in Gram-positive bacteria. The outer membrane of the Gram-negative bacteria serve as a permeability barrier which prevents externally applied peptides from accessing the periplasmic space and intracellular compartments of the cell.

The present invention provides means to use bacteriocins (which comprise naturally-occurring sequences) or chimeric bacteriocin constructs which selectively recognize and traverse the membrane barriers of target strains (referred to here as receptor-mediated translocation), to deliver appropriate cargo domains into desired cell compartments. Once there, the cargo domains can affect their intended activities, which may be detectable labeling or killing of cells. For example, a muralytic enzyme can digest the thin peptidoglycan layer of a Gram-negative cell, when typically the outer membrane prevents access of the muralytic activity from the outside medium. Linking an enzymatically active muralytic segment (fragment) to a translocation bacteriocin segment that provides for transfer of the muralytic segment across the outer membrane allows the enzymatic activity to contact the peptidoglycan layer, leading to degradation of the peptidoglycan layer. The failure of the peptidoglycan layer causes the cell to rupture due to the enormous osmotic pressure across the inner cell membrane. Alternatively, if the receptor-mediated translocation bacteriocin segment can translocate the cargo domain into the cell, many different mechanisms may be used to interfere with cell function. Nucleases, toxins, toxic conjugates, metabolic blocks, and other disruptive segments translocated into the cell cytoplasm can severely affect cell viability and health. Detectable labels may be introduced, e.g., to allow for detection of the cells to evaluate distribution within an organism.

In certain embodiments, the present invention provides a substantially isolated bacteriocin polypeptide (ie, a bacteriocin or chimeric bacteriocin construct) capable of killing target Gram-negative bacteria comprising: (a) a receptor-mediated translocation segment, optionally comprising at least 70% matching to a Translocation Segment (TS) of a bacteriocin and/or at least 70% matching to a Receptor Binding Segment (RBS) of a bacteriocin; and (b) a killing segment capable of killing said target bacteria when operably linked to said receptor-mediated translocation segment; wherein said bacteriocin polypeptide: (i) is capable of killing said target bacteria when contacted with said chimeric bacteriocin construct; and (ii) comprises sequence different from a natural S-type pyocin. In certain embodiments, the bacteriocin polypeptide is used in combination with another antimicrobial, antibiotic, or other therapeutic intervention. In other preferred embodiments, the bacteriocin polypeptide is one wherein the: 70% matching of one segment is at least 80%; TS and RBS both originate from a single bacteriocin; target is a mixed bacteria culture; target comprises bacteria of different species; target comprises bacteria of different genera; killing segment is derived from a bacteriocin; killing segment is derived from a homologous bacteriocin; killing segment derived from a heterologous bacteriocin; or different sequence comprises a purification tag. In particular preferred embodiments, the bacteriocin polypeptide is one as described wherein: the target bacteria include a susceptible *Klebsiella* target; the TS and/or RBS is from a klebicin; the killing segment is from a klebicin; all of the TS, RBS, and killing segment are from klebicins; all of the TS, RBS, and killing segment are from a single klebicin; or each of the TS, RBS, and killing segment are from different klebicins. The invention also provides an isolated nucleic acid encoding a described recombinant klebicin. In other particular embodiments, the bacteriocin polypeptide will be one, wherein: the target bacteria contain a susceptible *Pseudomonas* target; the TS and/or RBS is from an S-type pyocin; the killing segment is from an S-type pyocin; all of the TS, RBS, and killing segment are from S-type pyocins; all of the TS, RBS, and killing segment are from a single S-type pyocin; or each of the TS, RBS, and killing segment are from different S-type pyocins. Also provided are an isolated nucleic acid encoding a pyocin polypeptide, as described, e.g., in a high expression plasmid or vector. A further particular embodiment provides a described bacteriocin polypeptide wherein: the target bacteria contain a susceptible *Escherichia* target; the TS and/or RBS is from a *coli* pesticin; the killing segment is from a *coli* pesticin; all of the TS, RBS, and killing segment are from *coli* pesticins; all of the TS, RBS, and killing segment are from a single *coli* pesticin; or each of the TS, RBS, and killing segment are from different *coli* pesticins. An isolated nucleic acid encoding a described recombinant pesticin polypeptide is provided.

In yet another embodiment, the invention provides a method of introducing bacteriocin sensitivity to a target bacterium, comprising a step of transferring a mobilizable element which introduces a bacteriocin receptor to said target which is expressed in the outer membrane of said target, thereby introducing the bacteriocin receptor to said target. Additionally, a method further comprising a step of contacting said receptor expressing target with a bacteriocin, as described, resulting in killing of the target bacterium.

An alternative embodiment encompasses a substantially isolated bacateriocin polypeptide capable of delivering a polypeptide segment across the outer membrane of a target Gram-negative bacteria comprising: (a) a Receptor Mediated Translocation Segment, typically comprising a segment at least 70% matching to a Translocation Segment (TS) of a bacteriocin; and/or a segment comprising at least 70% matching to a Receptor Binding Segment (RBS) of a bacteriocin; and (b) a cargo polypeptide segment for delivery to the target bacteria when operably linked to the Receptor Mediated Translocation Segment; wherein the isolated polypeptide is capable of delivering said cargo polypeptide across the outer membrane of the target bacteria when contacted with the polypeptide. Preferred embodiments include those isolated polypeptides wherein the: 70% matching of one segment is at least 80%; TS and RBS both originate from a single bacteriocin; target is a mixed bacteria culture; target comprises bacteria of different species; target comprises bacteria of different genera; cargo polypeptide is derived from a bacteriocin; cargo polypeptide is derived from a homologous bacteriocin; cargo polypeptide is derived from a heterologous bacteriocin; cargo polypeptide modulates viability or growth of target bacteria; or isolated polypeptide comprises a purification tag.

BRIEF DESCRIPTION OF THE SEVERAL VIEWS OF DRAWINGS

DETAILED DESCRIPTION OF THE INVENTION

I. Introduction

Figure 1:
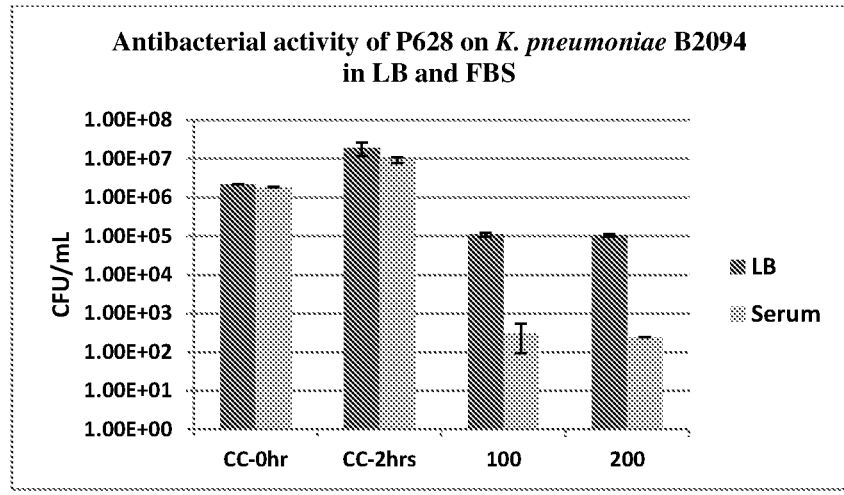
FIG. 1 shows antibacterial activity of P628 on *K. pneumoniae* B2094 in LB and PBS.

The present invention links a receptor-mediated translocation function (e.g., derived from a bacteriocin) to another functional cargo domain, e.g., a killing domain, as in a bacteriocin to achieve an entity which can attack the Gram-negative bacteria targets. The chimeric (and related) "bacteriocin" constructs described herein combine an bacteriocin-derived receptor-mediated translocation function linked to a labeling or killing function, which may be a peptidoglycan degrading enzyme activity. The bacteriocin-derived receptor-mediated translocation function is achieved with a protein segment which recognizes an outer membrane receptor on the bacteria, typically a protein, which assists in mediating the translocation. Generally, the receptor recognition function provides selectivity and specificity in target cell into which the translocation is effected. Thus, the translocation may be characterized as a "receptor-mediated" process. In many embodiments, the translocation involves two "functional" steps and domains within the bacteriocin, a binding step (involving receptor binding segment or RBS) and a translocation step (involving a translocation segment or TS), though the two steps may not necessarily be separable physically or temporally. The binding step often involves some specificity of binding of the bacteriocin to its cognate receptor, which then may take some conformational shape which allows the bacteriocin and the cargo domain to be transported or flipped across the lipid bilayer membrane.

In certain embodiments, the receptor-mediated translocation is only across the outer membrane, and the cargo domain is accessible to the periplasmic space of the bacterial host. The peptidoglycan (murein) sacculus is an essential structural component of the cell wall of most bacteria. Made of glycan strands cross-linked by short peptides, the sacculus forms a closed, bag-shaped structure surrounding the bacteria cytoplasmic membrane. The sacculus must withstand up to 25 atmospheres of osmotic pressure. The sacculus is flexible, allowing reversible expansion under pressure, which allows diffusion of even large protein molecules. See, e.g., Silhavy et al. (2010) *CSH Persp. Biol.*, 2:a000414; Vollmer et al. (2008) *FEMS Microbio. Revs* 32:149-167; Bos et al. (2007) *Ann. Rev. Microbiol.* 61:191-214; and Costerton et al. (1974) Bact. Revs. 38:87-110.

Many antibiotics act on the peptidoglycan layer of a target bacteria species. This structure is thus a critical component in the survival of a bacterial target. Attack of the peptidoglycan is a rational strategy for killing target bacterial hosts. Although the peptidoglycan layer is typically about 1-3 layers thick, the outer membrane of a Gram-negative bacterium serves as a permeability barrier that prevents externally applied enzymes from reaching their substrate.

The receptor-mediated translocation domain or segment allows the protein, e.g., with muralytic activity, to be transferred across the bacterial outer membrane. For example, the receptor-mediated translocation segment itself may mediate a membrane transfer event, thereby moving the muralytic activity from outside of the bacterial outer membrane to the inside, and allowing contact between the enzyme and its peptidoglycan substrate. The receptor-mediated translocation segment may take advantage of an endogenous translocation system in the outer membrane by presenting earmark motifs which signal the system to import the molecule into the periplasmic space. In some embodiments, the receptor-mediated translocation segment directs the construct polypeptide to the receptor expressing outer leaflet of the outer membrane, and the muralytic polypeptide flips from the outer leaflet of the outer membrane to the inner leaflet, thereby delivering the muralytic segment to the peptidoglycan substrate.

II. Gram-Negative Bacteria

A. Outer Membrane

The cell envelope of gram-negative bacteria consists of two membranes, the inner membrane (IM) and the outer membrane (OM), which are separated by the periplasm containing the peptidoglycan layer. The two membranes have an entirely different structure and composition. Whereas the IM is a phospholipid bilayer, the OM is an asymmetrical bilayer, consisting of phospholipids and lipopolysaccharides (LPS) in the inner and outer leaflet, respectively. Additionally, these membranes differ with respect to the structure of the integral membrane proteins. Whereas integral IM proteins typically span the membrane in the form of hydrophobic α-helices, integral OM proteins (OMPs) generally consist of antiparallel amphipathic β-strands that fold into cylindrical β-barrels with a hydrophilic interior and hydrophobic residues pointing outward to face the membrane lipids (Koebnik et al. (2000) "Structure and function of bacterial outer membrane proteins: barrels in a nutshell" Mol. Microbiol. 37:239-53). Both membranes also contain lipoproteins, which are anchored to the membranes via an N-terminal N-acyl-diacylglycerylcysteine, with the protein moiety usually facing the periplasm in the case of *Escherichia coli* (Pettersson et al. (1997) "Response of *Neisseria meningitidis* to iron limitation" Antonie van Leeuwenhoek 71:129-36). The LPS molecule can be divided into three parts: lipid A, core polysaccharides, and O-antigen repeats. Lipid A represents the hydrophobic component of LPS which locates in the outer leaflet of the outer membrane, while core polysaccharides and O-antigen repeats are displayed on the surface of the bacterial cells (Raetz et al. (2007) "Lipid A modification systems in Gram-negative bacteria" Annu Rev Biochem 76:295-329). The detailed structure of LPS varies from one bacterium to another, and this variation could affect the virulence of the bacterium. See, e.g., Galanos et al. (1985) "Synthetic and natural *Escherichia coli* free lipid A express identical endotoxic activities" Eur J Biochem 148:1-5; and Wilkinson (1996) "Bacterial lipopolysaccharides-themes and variations" Prog Lipid Res 35:283-343.

B. Peptidoglycan Layer

Peptidoglycan (murein) is an essential and specific component of the bacterial cell wall found on the outside of the cytoplasmic membrane of almost all bacteria (Rogers et al., (1980); Park, (1996); Nanninga, (1998); Mengin-Lecreulx & Lemaitre, (2005)). Its main function is to preserve cell integrity by withstanding the internal osmotic pressure. Any inhibition of its biosynthesis or its specific degradation during cell growth will result in cell lysis. Peptidoglycan also contributes to the maintenance of a defined cell shape and serves as a scaffold for anchoring other cell envelope components such as proteins (Dramsi et al., 2008) and teichoic acids (Neuhaus & Baddiley, (2003)). The peptidoglycan structure of both Gram-positive and Gram-negative bacteria comprises repeating disaccharide backbones of N-acetylglucosamine (NAG) and β-(1-4)-Nacetylmuramic acid (NAM) that are cross-linked by peptide stem chains attached to the NAM residues. In gram-negative bacteria, the stem peptide attached to the carboxyl group of each muramic acid usually consists of L-Ala-_-D-Glu-(L)-meso-diaminopimelic acid (Dap)-D-Ala, although the stem peptide often lacks D-Ala or, more rarely, terminates in D-Ala-D-Ala. About one-half of the stem peptides are involved in cross-links between neighboring glycan strands (Rogers et al., (1980)).

Muralytic domains are known in the art. Among these are the class of lysozyme proteins. See, e.g., Salazar and Asenjo (2007) *Biotechnol. Lett.* 29:985-94. Breakdown of the peptidoglycan structure occurs naturally in at least four contexts. One is biosynthesis of the structure itself; as the bacterial cell grows and divides, it must necessarily must break down the structure. See, e.g., Vollmer (2008) *FEMS Microbiol Rev.* 32:287-306; Scheurwater et al. (2008) *Int. J. Biochem. Cell Biol.* 40:586-91; Keep et al. (2006) *Trends Microbiol.* 14:271-276; and Baba and Schneewind (1998) *EMBO J.* 17:4639-4646. There are additional situations when the cell itself must rearrange or modify structure which was synthesized earlier. Second, eukaryotic hosts degrade the structure upon clearing of an infection, e.g., using mutanolysin or lysozymes. See, e.g., Callewaert and Michiels (2010) *J. Biosci.* 35:127-60; Harder et al. (2007) *Endocr. Metab. Immune Disord Drug Targets* 7:75-82; and Lichtman et al. (1992) *J. Clin. Invest.* 90:1313-1322. A third area is in phage replication, where the phage typically employs an endolysin to release the replicated phages and lyse the bacterial host cell. See, e.g., Srividhya and Krishnaswamy (2007) *J. Biosci.* 32:979-90; and Loessner (2005) *Curr. Opin. Microbiol.* 8:480-487. This is a lysis of the peptidoglycan layer of cells from within. The fourth context is where phage infection requires that the peptidoglycan barrier be traversed, as described in Padmanabhan et al. WO2007/130655. This is degradation of the peptidoglycan layer from the exterior of the cell.

Each of these mechanisms involves some means to disassemble the peptidoglycan structure. Thus, muralytic activities are found in genomes of eukaryotic hosts for bacteria, in bacteria genomes themselves, and in phage (and related prophages) which target bacteria as hosts. Muralytic domains can be found by homology to any of these sources, and informatics can be used to identify candidate genes with their respective canonical motifs. While the muralytic activity is one class of killing domains encompassed by the invention, many of the examples are described using this example and the invention is not to be limited to these embodiments, but many other killing or toxic segments may be substituted.

Peptidoglycan "degrading activities" can be converted into highly effective bactericidal activities for use against Gram-negative bacterial pathogens under therapeutic conditions, and can include muraminidase, glucosaminidase, amidase, or endopeptidase activities. Exemplary muralytic domains can be identified, incorporated into chimeric constructs to be delivered to the peptidoglycan substrate, produced, purified, and confirmed to have bactericidal activity against bacterial hosts with an outer membrane. Recombinant constructs comprising such activities have significant advantageous properties as antimicrobial compositions and formulations.

An example of the linked polypeptides of the invention uses a muralytic fragment, e.g., comprising a lysozyme domain from *Pseudomonas* phage P134, which is closely related to phage phiKMV. The ORF36 in phage P134 that corresponds to that in phiKMV lyses Gram-negative bacterial cells whose outer membrane has been removed. Contacting the construct to a variety of different Gram-negative bacteria after the outer membrane was removed resulted in the cells being broken down. These results demonstrate that the peptidoglycans from different Gram-negative bacteria species are susceptible to the muralytic activity.

Sequence homology searches identify various other similar domains which can be used as alternative sources for peptidoglycan degrading activities. The small size of the polypeptides exhibiting these activities affords efficient large scale production. Accessibility to relevant cell wall target components, e.g., peptidoglycans, at the bacterial target is provided, as are pharmacological distribution upon in vivo administration.

Relevant muralytic activities can be found within the lysozyme-like superfamily, lytic transglycosylase (LT), goose egg white lysozyme (GEWL); the Superfamily C100442 containing Lysozyme like domain, which contains several members including the Soluble Lytic Transglycosylases (SLT), Goose Egg-White Lysozymes (GEWL), Hen Egg-White Lysozymes (HEWL), Chitinases, Bacteriophage lambda lysozymes, Endolysins, Autolysins, Chitosanases. All these members are involved in the hydrolysis of beta-1,4-linked polysaccharides. The Cysteine Histidine dependent Amidohydrolase/Peptidase (CHAP) domain is found in phage endolysins and bacterial autolysins. Most proteins containing a CHAP domain function as peptidoglycan hydrolases and are commonly associated with amidases. See Bateman and Rawlings (2003) *Trends Biochem. Sci.* 5:234-237; and Pritchard et al. (2004) *Microbiology* 150:2079-2087. See also the Carbohydrate-Active enZYmes Database found at cazy.org. The CAZY database describes the families of structurally related catalytic and carbohydrate-binding modules (or functional domains) of enzymes that degrade, modify, or create glycosidic bonds. Another source for endopeptidases is the database from the website found at merops.sanger.ac.uk/cgi-bin/clan_index?type=P.

Analogous strategies can be used to identify and use other killing domains from muralytic domains, based, e.g., on the killing functions described below. Certain functional killing domains may be identified, and analogous or homologous alternative substitutions may be constructed.

C. Cell Membrane

Lipases and other functional activities which degrade the lipid bilayer of the prokaryote host can kill the cell. Additional toxic or toxin segments which will kill the target Gram-negative cells might be substituted, as could smaller molecule toxins conjugated to a cargo peptide for translocation into the cell. Preferably activities which act only on prokaryotes and would have no effect on a eukaryote will be highly selective in effect, only acting on the target but having little or no effect on a host organism being infected by a Gram-negative bacteria.

I. Bacteriocin Polypeptides

A. Bacteriocins

Bacteriocins are a diverse family of protein antibiotics produced by bacteria, which are naturally used to kill members of the same or closely related species. Bacteriocins produced by *E. coli*, called the colicins, were the first ones to be identified and are well studied and many of them are characterized. Almost all of the colicins characterized so far exhibit a three domain architecture with an N-terminal translocation domain, a receptor binding domain and a C-terminal killing domain. The killing domains are usually either nucleases or membrane damaging pore formers. The bacteriocin producing bacteria is protected from its own action by immunity protein that is produced by the bacteriocin expressing strain and functions by stochiometrically binding to the killing domain and inhibiting its activity.

Examples of bacteriocins polypeptides useful in the invention, along with their domain boundaries, are presented in Table 1.

TABLE 1

Domain boundaries of Bacteriocins and Chimeric Bacteriocin Constructs

| SEQ ID NO: | Bacteriocin Polypeptide | Domain |
| --- | --- | --- |
| 2 | Klebicin CCL | Translocation domain: 1-320<br>Receptor binding domain: 322-457<br>Killing domain: 475-559 |
| 4 | Klebicin B | Translocation domain: 1-490<br>Receptor binding domain: 492-631<br>Killing domain: 632-765 |
| 6 | Klebicin C | Translocation domain: 1-239<br>Receptor binding domain: 376-517<br>Killing domain: 533-616 |
| 8 | Klebicin D | Translocation domain: 1-315<br>Receptor binding domain: 467-609<br>Killing domain: 626-710 |
| 12 | Klebicn CCL TD RD- Klebicin B KD | Klebicin CCL:<br>Translocation domain: 1-320<br>Receptor binding domain: 321-473<br>Klebicin B killing domain: 474-615 |
| 14 | P623 S5 TD-RD-Linker-GP36 CD-his | S5 translocation domain: 1-150<br>S5 receptor binding domain: 151-300<br>Linker: 301-306<br>GP36 CD: 307-521<br>XhoI site: 522-523<br>6X his: 524-529 |
| 16 | P624 S5 TD-RD-Linker-GP36 CD | S5 translocation domain: 1-150<br>S5 receptor binding domain: 151-300<br>Linker: 301-306<br>GP36 CD: 307-521 |
| 18 | P625 S5 TD-RD-Linker-Phi29CD | S5 translocation domain: 1-150<br>S5 receptor binding domain: 151-300<br>Linker: 301-306<br>Phi29 CD: 307-454 |
| 20 | P626 S5 TD-RD-Linker-BP7e | S5 translocation domain: 1-150<br>S5 receptor binding domain: 151-300<br>Linker: 301-306<br>BP7e: 307-467 |
| 22 | P638 S5 Pyocin with 6X-His tag | S5 translocation domain: 1-150<br>S5 receptor binding domain: 151-300<br>S5 killing domain: 301-498<br>6X his: 499-504 |
| 24 | P652 S5 Pyocin without His tag | S5 translocation domain: 1-150<br>S5 receptor binding domain: 151-300<br>S5 killing domain: 301-498 |
| 26 | Fyu A BD- T4 lysozyme fusion | Translocation domain- 1-25<br>Receptor binding domain- 1-67<br>T4 lysozyme domain: 168-329 |
| 28 | Fyu A BD - GP36 fusion | Translocation domain- 1-25<br>Receptor binding domain- 1-167<br>T4 lysozyme domain: 168-383 |
| 30 | PelB-FyuA receptor | Pel B: 1 to 22<br>FyuA receptor: 23 to 675 |

Klebicins:

Bacteriocins produced by *Klebsiella* are called klebicins. Klebicins have similar domain architecture as that of the colicins isolated from *E. coli*. Four different types of klebicins were reported and whose DNA sequence was described—Klebicin B, Klebicin C, Klebicin CCL and Klebicin D (Riley et al. (2001) and Chavan et al. (2005))

S-Type Pyocins:

Soluble or S-type pyocins are protease- and heat-sensitive, chromosome-encoded bacteriocins from *P. aeruginosa* that are able to kill cells from the same species. These antibacterials are secreted a binary protein complexes consisting of large protein that harbors the killing function and a smaller immunity protein that remains tightly bound to the cytotoxic domain of the former. Several types of S-type pyocins have been described and characterized: pyocins 51, S2, AP41, S3, S4 and S5. Pyocin Sa turned out to be identical to pyocin S2. To kill a target cell, a S-type pyocin would first bind to a specific receptor located on the outer membrane of the bacterial cells and it would then be further translocated to exert its inhibitory function.

Pesticin:

Pesticin from *Yersinia pestis* is a toxin that kills *Y. pestis*, *Yersinia enterocolitica*, and certain *Escherichia coli* strains (Hu and Brubaker (1974)), which is encoded by a 9.5 kb plasmid, pYP (Kol'tsova et al. (1973); Ferber and Brubaker, (1981)). Pesticin exhibits N-acetylglucosaminidase activity (Ferber and Brubaker (1979)). Pesticin can utilize the FyuA receptor that is responsible for the transport of the yersiniae iron chelator, yersiniabactin (Heesemann et al. (1993); Rakin et al. (1994); Fetherston et al. (1995)). The expression of pesticin is thought to be controlled by the SOS system (Hu et al. (1972)), and its transport through the outer membrane and interaction with the cognate FyuA receptor is TonB-dependent (Ferber et al. (1981)).

B. Cargo Domain

To prepare chimeric constructs of the invention, a bacteriocin-derived receptor-mediated translocation domain is linked to a heterologous cargo domain that provides a desired function (e.g., labelling or killing). For example, a killing segment will comprise a segment, which may be less than the complete "domain" and include variations which retain function but differ from a classically defined "domain", which will kill the target cell. The domain may be a component of a protein, e.g., of a bacteriocin, which naturally operates to kill the target cell. That domain may be substituted or replaced with another domain which can kill the target cell, which may be a catalytic activity which can kill the cell, or may be some structural feature which functions to block or interfere with normal cell activity to effect killing. Yet another option is for actual toxic chemicals or structures to be conjugated or attached to carrier peptide or other chemical linkages which are operably linked to the receptor-mediated translocation domain. Examples may be toxic conjugates analogous to those used as targeted toxins in chemotherapies, which might be taken up into the target cells and released from the carrier inside the cell, with a stoichiometry which may interfere in many different copies of target enzyme or substrate. Examples of killing segments are provided in Table 2.

TABLE 2

| | Bacteriocin-derived Killing Segments | | |
|---|---|---|---|
| 1 | DNase | Cytoplasm | Pyocin S1, S2, S3, Klebicin B |
| 2 | rRNase | Cytoplasm | Pyocin S6, Colicin E3, E4, E6, Klebicin C, CCL, Cloacin DF13 |
| 3 | tRNase | Cytoplasm | Pyocin S4, Colicin E5, Colicin D, Klebicin D |
| 4 | Pore formation (Cell membrane damage) | Periplasm | Pyocin S5, Colicin 1a |
| 5 | Peptidoglycan degradation (muraminidase) | Periplasm | Colicin M, Pesticin |
| 6 | Inhibitors of periplasmic enzymes | Periplasm | Pyocin PaeM |

Large bacteriocins (>60 kDa) are protein toxins that kill bacteria closely related to the producing organism by targeting either nucleic acids (e.g., DNA, and RNA, tRNA or rRNA) in the cytoplasm or cell membrane components of susceptible bacteria. Genes coding for bacteriocins are located either on plasmids or genomes of the producing organism and could be identified for the whole genome sequence using various bioinformatic tools. Whole genome information available from a database, e.g., the NCBI Genome database, can be mined to identify putative bacteriocins and multiple sequence alignment and sequence identity searches will help in narrowing down on the possible bacteriocins. For example, more than 3000 nuclease bacteriocins were identified using a Hidden Markov Model (HMM) from 53 different bacterial species distributed across diverse ecological niches, including human, animals, plants, and the environment (Sharp et al. (2017) Diversity and distribution of nuclease bacteriocins in bacterial genomes revealed using Hidden Markov Models. PLoS Comput Biol 13(7): e1005652). In addition to nucleases and pore forming activity, bacteriocins can also be lipases; decouplers of oxidation; activatable mutagens; blockers of transcription/translation; inducers of apoptosis; interference with critical cell functions such as cdc, energy metabolism, cell wall and membrane biogenesis and maintenance, etc.

In addition to killing domains derived from bacteriocins, antimicrobial peptides derived from a number of sources can be used. Examples are provided in Table 3.

TABLE 3

| Antimicrobial peptides (AMPs) for fusion to bacteriocins | | | |
|---|---|---|---|
| Antimicrobial peptide | Amino acid Sequence | Salient features | Reference |
| WLBU2 | RRWVRRVRRWVRRV VRVVRRWVRR | de novo design of modular cationic amphipathic peptides (CAPs) reported to be active in human serum | Deslouches et al. (2005) Activity of the De Novo Engineered Antimicrobial Peptide WLBU2 against *Pseudomonas aeruginosa* in Human Serum and Whole Blood: Implications for Systemic Applications *Antimicrobial Agents and Chemother.* 49:3208-3216 |
| Cathelicidin related antimicrobial peptide (CRAMP) | GLLRKGGEKIGEKLKK IGQKIKNFFQKLVPQPE Q | Derived from mouse analogue of cathlelicidin antimicrobial peptide (CAP) | Mishra et al. (2015) Evaluation of the antibacterial and antibiofilm activities of novel CRAMP-vancomycin conjugates with diverse linkers *Org. Biomol. Chem.* 13(27):7477-86 |
| Sushi | HAEHKVKIGVEQKYG QFPQGTEVTYTCSGNY FLM | Corresponds to residues 268 to 301 of the factor C Sushi 3 domain designated S3 | Li et al. (2004) Perturbation of Lipopolysaccharide (LPS) Micelles By Sushi 3 (S3) Antimicrobial Peptide *J. Biol. Chem.* 279:50150-50156. |
| RI18 | RKKTRKRLKKIGKVLK WI | Derived from Porcine myeloid antimicrobial peptide-36 (PMAP-36) | Lyu et al. (2016) Antimicrobial activity, improved cell selectivity and mode of action of short PMAP-36-derived peptides against bacteria and *Candida* Scientific Reports, article number: 27258 |
| Cecropin-bee melittin hybrid peptide (CEME) | KWKLFKKIGIGAVLKV LTTGLPALIS | Resistant to salt up to 300 mM | Friedrich et al. (1999) Salt-Resistant Alpha-Helical Cationic Antimicrobial Peptides *Antimicrobial Agents and Chemotherapy* 43:1542-1548 |

TABLE 3-continued

Antimicrobial peptides (AMPs) for fusion to bacteriocins

| Antimicrobial peptide | Amino acid Sequence | Salient features | Reference |
| --- | --- | --- | --- |
| Synthetic peptide hLF1-11 | GRRRRSVQWCA | Corresponds to the N-terminal eleven residues of human lactoferrin | Brouwer et al. (2011) Discovery and development of a synthetic peptide derived from lactoferrin for clinical use Peptides 32:1953-1963. |
| Magainin | GIGKFLHSAKKFGKAFVGEIMNS | Isolated from Xenopus skin, have broad spectra of antimicrobial activity and low toxicities to normal eukaryotic cells | Matsuzaki et al. (1997) Interactions of an Antimicrobial Peptide, Magainin 2, With Outer and Inner Membranes of Gram-Negative Bacteria Biochim. Biophys. Acta 1327:119-130 |
| Omiganan | ILRWPWWPWRRK | Isolated from the cytoplasmic granules of bovine neutrophils | Sader et al. (2004) Omiganan Pentahydrochloride (Mbi 226), A Topical 12-Amino-Acid Cationic Peptide: Spectrum of Antimicrobial Activity and Measurements of Bactericidal Activity Antimicrob Agents Chemother. 48(8):3112 |
| Arenicin-3 | GFCWYVCYRNGVRVCYRRCN | Isolated from the lugworm Arenicola marina. Exhibit potent, rapid antimicrobial activity in vitro against a broad range of multi-resistant pathogenic Gram-negative bacteria | Andra et al. (2008) Structure and Mode of Action of the Antimicrobial Peptide Arenicin Biochem J. 410(1):113-22 |
| LBP peptide | SDSSIRVQGRWKVRASFFKLQGSFDVSVKG | Corresponds to the N terminal region of lipopolysaccharide binding protein (LBP) that has high affinity to Lipopolysaccharide (LPS) | Taylor et al. (1995) Lipopolysaccharides Neutralizing Peptides Reveal a Lipid A Binding Site of LPS Binding Protein J. Biol. Chem. 270:17934-17938 |
| Protamine | PRRRRSSSRPVRRRRRPRVSRRRRRRGGRRRR | A polycationic peptide found in the nuclei of sperm of different animal species | Aspedon et al. (1996) The Antibacterial Action of Protamine: Evidence for Disruption of Cytoplasmic Membrane Energization in Salmonella Typhimurium Microbiology 142:3389-3397 |
| Apidaecins | GNNRPVYIPQPRPPHPRL | Proline-rich AMPs expressed in insects as part of the innate immune system. They are very active against Gram-negative bacteria, especially Enterobacericeae members | Czihal et al. (2009) Mapping of Apidaecin Regions Relevant for Antimicrobial Activity and Bacterial Internalization Internatl J. Peptide Res. And Therapeutics 15(2):57-164 |
| Sheep myeloid antimicrobial peptide (SMAP29) | RGLRRLGRKIAHGVKKYGPTVLRIIRIAG | α-helical cathelicidin derived peptide deduced from sheep myeloid mRNA | Skerlavaj et al. (1999) Smap-29: A Potent Antibacterial and Antifungal Peptide from Sheep Leukocytes FEBS Letters 463:58-62 |
| Sheep myeloid antimicrobial peptide -18 (SMAP18) | RGLRRLGRKIAHGVKKYG | Synthetic α-helical cathelicidin derived peptide deduced from sheep myeloid mRNA | Jacob B et.al. (2016) The stereochemical effect of SMAP-29 and SMAP-18 on bacterial selectivity, membrane interaction and anti-inflammatory activity. Amino acids DOI 10.1007/s00726-016-2170-y |

C. Linkers, Other Components; Immunity Proteins

Many of the chimeric constructs of the invention will have linkers which attach the different components as a single polypeptide. Alternatively, the construct may comprise multiple polypeptides, often synthesized as a single polypeptide but may be cleaved and maintain structural integrity by secondary or tertiary structure.

Rates of transfer across the outer membrane can be measured by a number of methods. One method is to indirectly evaluate the results of transfer, e.g., the effects of a killing segment reaching its periplasmic substrate. The criteria of measurement can be release of measureable cell contents, substrate release, or cell lysis. Cell killing can also be a measure of peptidoglycan digestion.

A more direct method is to track the number of molecules transferred into the periplasmic space, e.g., using a detectable label. The efficiency of transfer of a particular transfer segment will often be evaluated by measuring an amount of passenger segment transferred. A detectable label can be used to differentiate between the periplasmic space conditions (more oxidizing than outside the OM) and the extracellular environment. See Rajarao et al. (2002) FEMS Microbiology Letters 215:267-272.

An efficient receptor-mediated translocation segment will effect at least a 3 fold increase in the level of killing of target host by the killing segment, or at least a 3-fold increase in the level of transfer, as compared to absence of the membrane transfer segment. In some embodiments, the receptor-mediated translocation segment will increase the level of killing or transfer by at least about 5, 7, 10, 15, 20, 30, 50, 80, 100, 150, 250 or more fold compared to the absence of the membrane transfer segment. The assay is typically carried out under conditions which approximate the concentrations which might be used according to the application. The assay will typically measure transfer over a time period ranging from minutes, e.g., about 1, 2, 5, 10, 15, or 30 minutes, to an hour or two.

II. Definitions

"Receptor Mediated Translocation Domain" (RMTD) is the domain, typically derived from a bacteriocin or related protein, which functions to provide receptor specific translocation of the bacteriocins and chimeric constructs of the invention across the Gram-negative Outer Membrane. Generally domain structure considers secondary or tertiary protein structure in setting boundaries. The identified segments have been described above. Various forms of mutagenesis or means to test variability in the necessary matching of sequence can be empirically tested. Generally, the RMTD will exhibit at least about 60% matching when optimally aligned to a natural sequence, but will preferably have greater matching, e.g., about 65%, 70%, 75%, 80%, preferably 85%, 90%, 95%, or more over the region of alignment. Segments will typically be regions exhibiting particularly higher matching rates than over the entire domain, over regions which may be generally at least about 65%, 70%, 75%, preferably 80%, 85%, 90% or more of the length. The segment matching will be a selected higher matching number over a shorter segment of alignment.

In some embodiments, the receptor-mediated translocation domain (RMTD) can comprise two distinct segments. The first is a "Receptor Binding Segment" (RBS), typically derived from a bacteriocin or related protein, which confers selectivity or specificity of interaction of the chimeric construct with a cognate receptor. This interaction is important in the initial interaction between the construct and the target, and generally provides selectivity, which then allows the temporal steps of the translocation process to take place. The RBS will likely be testable for maintaining function as the sequence of the domain is modified, e.g., with substitutions or modification, to evade claim scope. The matching to natural sequence will typically be at least about, e.g., 65% of the natural, about 70%, 75%, 80%, preferably about 85%, 90%, 95%, or more over the region of alignment. Receptor Binding Segments will be regions of particularly high matching over shorter segments. The length of alignment may be generally at least about 65%, 70%, 75%, preferably 80%, 85%, 90% or more of the length of the domain, with any combination of the matching measures. The second segment is a "translocation segment," (TS) also referred to as a TMD (transmembrane domain), translocating domain, transfer segment, and like terms, which can affect transfer of an operably linked cargo domain across the outer membrane of Gram negative bacteria. Such a domain may itself have the ability to translocate the associated segment across the membrane, or be recognized by an endogenous translocation system which will effect transport of the linked catalytic segment. The chimeric polypeptide can be transferred intact across the membrane, or be modified during translocation. The membrane transfer domain can itself further have the ability to compromise the inner membrane, thereby killing by this additional mechanism.

"Cargo Domain" will typically be a functional protein domain which will be translocated when operably linked to the RMTD. The "cargo" descriptor emphasizes that the domain, or segment, may be passive or active. In certain embodiments, the segment may have function, e.g., a killing domain or segment, which effects killing of the target cell upon translocation. The killing may be catalytic, e.g., enzymatic, as a nuclease, protease, muralytic enzyme, metabolic disruptor, structural disassembler, or any of many active functions which can effect toxicity or killing, whether directly or indirectly. The segment or domain may be passive, e.g., as a labelling segment, like GFP or carrier of various chemically attached entities. Thus, the cargo domain may be a polypeptide used as a carrier for toxic conjugates which are chemically transported to the cell compartment, and there released, which may act in a stoichiometric manner. Chemical attachment of antibiotics, antimicrobials, or the like may be delivered into the appropriate cell compartment by the translocation process and released at the appropriate site within the target cell.

"Operably linked" refers to functional linkage of elements. Thus two elements are operably linked if the function of the first segment (e.g., translocation domain) operates to translocate a cargo domain, e.g., a muralytic or other functional (killing) segment or domain.

A "killing activity" may include an enzymatic activity that kills or decreases the viability or growth rate of the target bacteria.

An "environment" of a bacterium can include an in vitro or an in vivo environment. In vitro environments can include a reaction vessel, e.g., holding isolated or purified bacteria, a surface to be sterilized (e.g., in a public health facility), equipment, surfaces in animal quarters, or public health facilities such as water, septic, or sewer facilities. Other in vitro conditions can provide mixed species populations, e.g., including a number of symbiotically or interacting species in close proximity. An in vivo environment can be a host organism infected by a target bacterium. In vivo environments include organs, such as bladder, kidney, lung, skin, heart and blood vessels, stomach, fur, intestine, liver, brain or spinal cord, sensory organs, such as eyes, ears, nose, tongue, pancreas, spleen, thyroid, etc. In vivo environments include tissues, such as gums, nervous tissue, lymph tissue, glandular tissue, and biological fluids, e.g., blood, sputum, etc. Catheter, tubing, implant, and monitoring or treatment devices which are introduced into or attached to the body may be sources of infection under normal usage. Environments also include the surface of food, e.g., fish, meat, or plant materials. Meats include, e.g., beef, pork, chicken, turkey or other poultry. Plant materials include vegetable, fruits, or juices made from fruits and/or vegetables, or may include clothing or shelter. In some embodiments, surfaces that have come in contact with a bacterially-infected food product are treated with a protein of the invention, including a VAME construct or chimera.

"Introducing" a composition to an environment includes applying or administering a compound or composition, and such that a targeted bacteria is exposed to the compound or composition. Introducing said compound or composition can be effected by live or dead bacteria which may produce or release such.

A "cell wall degrading protein" is a protein that has detectable, e.g., substantial, degrading activity on an accessible cell wall or components thereof "Muralytic" activity can be a result of the degrading activity. Cell wall degrading domains can be derived, e.g., from the tail plates of myoviridae phage or ends of tails from siphoviridae phage, and other phage virion muralytic polypeptides.

"GMP conditions" refers to good manufacturing practices, e.g., as defined by the Food and Drug Administration of the United States Government. Analogous practices and regulations exist in Europe, Japan, and most developed countries.

The term "substantially" in the above definitions of "substantially pure" generally means at least about 60%, at least about 70%, at least about 80%, or more preferably at least about 90%, and still more preferably at least about 92%, 95%, 97%, or 99% pure, whether protein, nucleic acid, or other structural or other class of molecules.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analog refers to a compound that has the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain a basic chemical structure as a naturally occurring amino acid. Amino acid mimetic refers to a chemical compound that has a structure that is different from the general chemical structure of an amino acid, but that functions in a manner similar to a naturally occurring amino acid.

"Protein", "polypeptide", or "peptide" refers to a polymer in which most or all of the monomers are amino acids and are joined together through amide bonds, alternatively referred to as a polypeptide. When the amino acids are α-amino acids, either the L-optical isomer or the D-optical isomer can be used. Additionally, unnatural amino acids, e.g., β-alanine, phenylglycine, and homoarginine, are also included. Amino acids that are not gene-encoded may also be used in the present invention. Furthermore, amino acids that have been modified to include appropriate structure or reactive groups may also be used in the invention. The amino acids used in the present invention may be the D- or L-isomer, or mixtures thereof. The L-isomers are generally preferred. In addition, other peptidomimetics are also useful in the present invention. For a general review, see, Spatola, A. F., in Weinstein et al. (eds. 1983) Chemistry and Biochemistry of Amino Acids, Peptides and Proteins, Marcel Dekker, New York, p. 267.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. In particular, fusions of sequence may be generated, e.g., incorporating an upstream secretion cassette upstream of desired sequence to generate secreted protein product.

A "fusion protein," "chimeric protein," "protein conjugate," and like terms refer to a protein comprising amino acid sequences that are in addition to, in place of, less than, and/or different from the amino acid sequences encoding the original or native full-length protein or subsequences thereof. More than one additional domain can be added to a cell wall muralytic protein as described herein, e.g., an epitope tag or purification tag, or multiple epitope tags or purification tags. Additional domains may be attached, e.g., which may add additional killing activities (on the target or associated organisms of a mixed colony or biofilm), targeting functions, or which affect physiological processes, e.g., vascular permeability or integrity of biofilm. Alternatively, domains may be associated to result in physical affinity between different polypeptides to generate multichain polymer complexes.

The term "nucleic acid" refers to a deoxyribonucleotide, ribonucleotide, or mixed polymer in single- or double-stranded form, and, unless otherwise limited, encompasses known analogues of natural nucleotides that hybridize to nucleic acids in a manner similar to naturally occurring nucleotides. Unless otherwise indicated or by context, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes typically include at least promoters and/or transcription termination signals. Typically, the recombinant expression cassette includes a nucleic acid to be transcribed (e.g., a nucleic acid encoding a desired polypeptide), and a promoter. Additional factors for effecting expression can be included. In certain embodiments, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In certain embodiments, a recombinant expression cassette encoding an amino acid sequence comprising a muralytic activity on a cell wall is expressed in a bacterial host cell.

A "heterologous sequence" or a "heterologous nucleic acid", as used herein, is one that originates from a source foreign to the particular host cell, or, if from the same source, is modified from its original form. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, or at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and, e.g., HPLC or mass spectroscopy or a similar means for purification may be utilized.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the sequence comparison algorithms or by visual inspection. In certain alignments of identity, no gaps are permitted, while in other algorithms, gaps are allowed with appropriate penalty measures.

The phrase "substantially identical," in the context of two nucleic acids or proteins, refers to two or more sequences or subsequences that have, over the appropriate segment, at least greater than about 60% nucleic acid or amino acid sequence identity, about 65%, 70%, 75%, 80%, 85%, 90%, preferably about 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over one or more region of the sequences that corresponds to at least about 13, 15, 17, 23, 27, 31, 35, 40, 50, or more amino acid residues in length, more preferably over a region of at least about 60, 70, 80, or 100 residues, and most preferably the sequences are substantially identical over at least about 150 residues, or over the entire length of the reference sequence.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these and related algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc. (1995 and Supplements) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information (ncbi.nlm.nih.gov) or similar sources.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at each position where an arginine is specified by a codon, the codon can be altered to another of the corresponding codons described without altering the encoded protein. Such nucleic acid variations are "silent variations," which are one species of "conservatively modified variations." Each polynucleotide sequence described herein which encodes a protein also describes possible silent variations, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is typically implicit in each described sequence.

Those of skill recognize that many amino acids can be substituted for one another in a protein without affecting the function of the protein, e.g., a conservative substitution can be the basis of a conservatively modified variant of a protein such as the disclosed cell wall muralytic proteins. An incomplete list of conservative amino acid substitutions follows. The following eight groups each contain amino acids that are normally conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton (1984) Proteins).

Furthermore, one of skill will recognize that individual substitutions, deletions, or additions which alter, add, or delete a single amino acid or a small percentage of amino acids (typically less than 5%, more typically less than 1%) in an encoded sequence are effectively "conservatively modified variations" where the alterations result in the substitution of an amino acid with a chemically similar amino acid. Conservative substitution tables providing functionally similar amino acids are well known in the art.

One of skill will appreciate that many conservative variations of proteins, e.g., killing segments or cell wall muralytic proteins, and nucleic acids which encode proteins yield essentially identical products. For example, due to the degeneracy of the genetic code, "silent substitutions" (e.g., substitutions of a nucleic acid sequence which do not result in an alteration in an encoded protein) are an implied feature of each nucleic acid sequence which encodes an amino acid. As described herein, sequences are preferably optimized for expression in a particular host cell used to produce the killing segment, e.g., cell wall muralytic proteins (e.g., yeast, human, and the like). Similarly, "conservative amino acid substitutions," in one or a few amino acids in an amino acid sequence are substituted with different amino acids with highly similar properties, are also readily identified as being highly similar to a particular amino acid sequence, or to a particular nucleic acid sequence which encodes an amino acid. Such conservatively substituted variations of any particular sequence are a feature of the present invention. See also, Creighton (1984) Proteins, W. H. Freeman and Company. In addition, individual substitutions, deletions or additions which alter, add or delete a single amino acid or a small percentage of amino acids in an encoded sequence generally are also "conservatively modified variations".

The practice of this invention can involve the construction of recombinant nucleic acids and the expression of genes in host cells, preferably bacterial host cells. Optimized codon usage for a specific host will often be applicable. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, Guide to Molecular Cloning Techniques, Methods in Enzymology volume 152 Academic Press, Inc., San Diego, CA (Berger); and Current Protocols in Molecular Biology, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as E. coli, and eukaryotic cells including insect (baculovirus), mammalian (CHO cells), fungal cells (e.g., yeast, Pichia, Aspergillus niger), and bacteriophage expression systems.

Examples of protocols sufficient to direct persons of skill through in vitro amplification methods, including the polymerase chain reaction (PCR), the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; PCR Protocols A Guide to Methods and Applications (Innis et al. eds) Academic Press Inc. San Diego, CA (1990) (Innis); Arnheim & Levinson (Oct. 1, 1990) C&EN 36-47; The Journal Of NIH Research (1991) 3:81-94; (Kwoh et al. (1989) Proc. Natl. Acad. Sci. USA 86: 1173; Guatelli et al. (1990) Proc. Natl. Acad. Sci. USA 87:1874; Lomell et al. (1989) J. Clin. Chem. 35:1826; Landegren et al. (1988) Science 241:1077-1080; Van Brunt (1990) Biotechnology 8:291-294; Wu and Wallace (1989) Gene 4: 560; and Barringer et al. (1990) Gene 89: 117. Improved methods of cloning in vitro amplified nucleic acids are described in Wallace et al., U.S. Pat. No. 5,426,039.

III. Commercial Applications

Various applications of the bacteriocin polypeptides described herein can be immediately recognized. The proteins can be used for antibacterial treatment of articles which may be contaminated in normal use. Locations, surfaces, equipment, or environments where target bacteria are public health hazards can be treated using the bacteriocin polypeptides described herein. Locations of interest include public health facilities where target bacteria containing materials exist. These materials may include waste products, e.g., liquid, solid, or air. Aqueous waste treatment plants may incorporate the described chimeric bacteriocin constructs to eliminate target bacteria from effluent, whether by treatment with the chimeric bacteriocin constructs or cells that express and release these polypeptides. Solid waste sites can introduce these polypeptides to minimize possibility of target host outbreaks.

Food preparation areas and equipment can be regularly treated using the described bacteriocin compositions, thereby providing means to effectively eliminate target bacteria. Medical and other public environments subject to contamination can use similar means to minimize growth and spread of target microorganisms. The present methods can be used in contexts where elimination of target bacteria is desired, including air filtration systems, e.g., for an intensive care unit.

The described bacteriocin polypeptides can be used as a protein stabilizer or a preservative, i.e., where the target bacteria are destabilizing agents. Such compositions can be used as part of the formulation for drugs, or preservative for meat or other food products. In some embodiments, these chimeric bacteriocin constructs can be used in aquatic food products, e.g., as a stabilizer or as a component of preservative formulations. Such applications are particularly useful for materials that must be kept antiseptic but cannot contain classical antibiotics.

Alternative applications include use in a veterinary or medical context. Means to determine the presence of particular bacteria, or to identify specific targets may utilize the effect of selective agents on the population or culture. Inclusion of bacteriostatic activities to cleaning agents, including washing of animals and pets, may be desired.

The bacteriocin polypeptides described herein can be used to treat bacterial infections of, e.g., humans, mammals, animals, and plants. These polypeptides can be administered to a subject prophylacticly or where the subject has a bacterial infection. In addition, the present methods can be applied to display (e.g., zoo or performing), companion (e.g., dogs, cats, other pets), racing (e.g., horses), or farm (e.g., dairy and beef cattle, sheep, goats, pigs, chicken, fish, shrimp, lobster, and the like) animals where the composition is applied to reduce the presence of bacteria. These chimeric bacteriocin constructs can be used to treat infections caused by bacteria that replicate slowly, as the killing mechanism does not depend upon host cell replication. Many current antibacterial agents, e.g., antibiotics, are most useful against replicating bacteria. For example, these bacteriocin polypeptides can be used to target bacteria that replicate with doubling times of about, e.g., 1-72 hours, 1-48 hours, 1-24 hours, 1-12 hours, 1-6 hours, 1-3 hours, or 1-2 hours.

Medically relevant Gram-negative cocci species include *Neisseria gonorrhoeae* and spirochaetes (causing a sexually transmitted disease); *Neisseria meningitides* (causing meningitis); and *Moraxella catarrhalis* (causing respiratory symptoms). Relevant Gram-negative bacilli species include *Hemophilus influenzae, Klebsiella pneumoniae, Legionella pneumophila, Burkholderia*, and *Pseudomonas aeruginosa* (respiratory problems); *Escherichia coli, Proteus mirabilis, Enterobacter cloacae*, and *Serratia marcescens* (urinary problems), and *Helicobacter pylori, Salmonella enteritidis, Salmonella typhi* (gastrointestinal problems), and spirochaetes (sexually transmitted disease). Gram-negative bacteria associated with nosocomial infections include *Acinetobacter baumannii*, which cause bacteremia, secondary meningitis, and ventilator-associated pneumonia, e.g., in intensive-care units of hospital establishments.

Other relevant that can be targeted using the presently described bacteriocin polypeptides include Gram-negative species include *Stenotrophomonas*, Bdellovibrio, acetic acid bacteria, and alpha-proteobacteria such as *Wolbachia*, the cyanobacteria, spirochaetes, green sulfur and green non-sulfur bacteria.

Gram-variable organisms, which may have an outer membrane under certain conditions (display a Gram-variable pattern with Gram staining), can also be targeted using the present bacteriocin polypeptides. Gram-variable bacteria include e.g., the genera *Actinomyces, Arthobacter, Corynebacterium, Mycobacterium*, and *Propionibacterium*, which have cell walls particularly sensitive to breakage during cell division, and display Gram-negative staining. In cultures of *Bacillus, Butyrivibrio*, and *Clostridium*, a decrease in peptidoglycan thickness during growth coincides with an increase in the number of cells that stain Gram-negative. In addition, the age of the bacterial culture can influence the results of the Gram stain.

IV. Administration

The route of administration and dosage of these bacteriocin polypeptides chimeric bacteriocin constructs described herein vary with the infecting bacteria strain(s), the site and extent of infection (e.g., local or systemic), and the subject being treated. The routes of administration include but are not limited to: oral, aerosol or other device for delivery to the lungs, nasal spray, intravenous (IV), intramuscular, intraperitoneal, intrathecal, intraocular, vaginal, rectal, topical, lumbar puncture, intrathecal, and direct application to the brain and/or meninges. Excipients which can be used as a vehicle for the delivery of the therapeutic will be apparent to those skilled in the art. For example, the muralytic polypeptide can be in lyophilized form and dissolved (resuspended) prior to administration (e.g., by IV injection). The dosage is contemplated to be in the range of about 0.03, 0.1, 0.3, 1, 3, 10, 30, 100, 300, 1000, 3000, 10000 or more chimeric bacteriocin construct molecules per bacterium in the host infection. Depending upon the size of the protein, which may itself be tandemly associated, or in multiple subunit form (dimer, trimer, tetramer, pentamer, etc.) or in combination with one or more other entities, e.g., enzymes or fragments of different specificity, the dose may be about 1 million to about 10 trillion/per kg/per day, and preferably about 1 trillion/per kg/per day, and may be from about $10^6$ killing units/kg/day to about $10^{13}$ killing units/kg/day.

Methods to evaluate killing capacity may be similar to methods used by those of skill to evaluate intact replicating phage, e.g., plaque forming units or pfu, though killing units may be better evaluated by determining the number of surviving bacteria after titration of the killing units. Quantification of killing is distinct, since non-replicating phage will not form plaques on bacterial host lawns. Thus, serial dilution methods can be used to evaluate the quantity of "killing" units in place of standard pfu. Serial dilutions of bacterial cultures exposed to the killing compositions can be used to quantify killing units. Total bacterial counts can be compared with viable colony units can establish the viable fraction of bacteria and what fraction was susceptible to the killing constructs. Other means for evaluating stasis activity may include release of intracellular contents, whether natural or loaded, or enzymatic activity on defined or prepared substrates which correspond to natural cell wall structures.

The therapeutic(s) are typically administered until successful elimination of the pathogenic bacteria is achieved. The invention contemplates single dosage forms, as well as multiple dosage forms of the compositions of the invention, as well as methods for accomplishing sustained release means for delivery of such single and multi-dosages forms. Broad spectrum formulations can be used while specific diagnosis of the infecting strain is determined.

With respect to the aerosol administration to the lungs or other mucosal surfaces, the therapeutic composition is incorporated into an aerosol formulation specifically designed for administration. Many such aerosols are known in the art, and the present invention is not limited to any particular formulation. An example of such an aerosol is the Proventil™ inhaler manufactured by Schering-Plough, the propellant of which contains trichloromonofluoromethane, dichlorodifluoromethane, and oleic acid. Other embodiments include inhalers that are designed for administration to nasal and sinus passages of a subject or patient. The concentrations of the propellant ingredients and emulsifiers are adjusted if necessary based on the specific composition being used in the treatment. The number of enzyme killing units to be administered per aerosol treatment will typically be in the range of about $10^6$ to $10^{13}$ killing units, e.g., about $10^{12}$ killing units.

Typically, the killing will decrease the host replication capacity by at least about 3 fold, e.g., 10, 30, 100, 300, etc., to many orders of magnitude. Slowing the rate of host replication without killing can also have significant therapeutic or commercial value. Genetic inactivation efficiencies may be about 4, 5, 6, 7, 8, or more log units.

V. Formulations

The invention further contemplates pharmaceutical compositions comprising at least one bacteriocin polypeptide of the invention provided in a pharmaceutically acceptable excipient. The formulations and pharmaceutical compositions of the invention thus contemplate formulations comprising an isolated bacteriocin polypeptide specific for a bacterial host; a mixture of two, three, five, ten, or twenty or more enzymes that affect the same or typical bacterial host; and a mixture of two, three, five, ten, or twenty or more enzymes that affect different bacterial hosts or different strains of the same bacterial host, e.g., a cocktail mixture of bacteriocin polypeptides that collectively inhibit the growth of multiple Gram-negative bacterial species. In this manner, the compositions of the invention can be tailored to the needs of the patient. The compounds or compositions can be sterile or near sterile.

A "therapeutically effective dose" is a dose that produces the effects, bacteriostatic (reducing bacterial growth) or bactericidal (killing bacteria), for which it is administered. The exact dose will depend on the purpose of the treatment, and will be ascertainable by one skilled in the art using known techniques. See, e.g., Ansel et al., Pharmaceutical Dosage Forms and Drug Delivery; *Lieberman* (1992) *Pharmaceutical Dosage Forms* (vols. 1-3), Dekker; Lloyd (1999) *The Art, Science and Technology of Pharmaceutical Compounding;* and *Pickar* (1999) *Dosage Calculations.* As is known in the art, adjustments for protein degradation, systemic versus localized delivery, as well as the age, body weight, general health, sex, diet, time of administration, drug interaction, and the severity of the condition may be necessary, and will be ascertainable by those skilled in the art.

Various pharmaceutically acceptable excipients are well known in the art. As used herein, "pharmaceutically acceptable excipient" includes a material which, when combined with an active ingredient of a composition, allows the ingredient to retain biological activity and without causing disruptive reactions with the subject's immune system. Such excipients include stabilizers, preservatives, salt or sugar complexes or crystals, and the like.

Exemplary pharmaceutically carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In other embodiments, the compositions will be incorporated into solid matrix, including slow release particles, glass beads, bandages, inserts on the eye, and topical forms.

Further included are formulations for liposomal delivery, and formulations comprising microencapsulated enzymes, including sugar crystals. Compositions comprising such excipients are formulated by well known conventional methods (see, e.g., *Remington's Pharmaceutical Sciences*, Chapter 43, 14th Ed., Mack Publishing Col). The proteins may be subjected to PEGylation to achieve advantages often deriving therefrom. See, e.g., Jevsevar et al. (2010) *Biotechnol. J.* 5:113-128; Brocchini et al. (2008) *Adv. Drug Delivery Revs.* 60:3-12; Jain and Jain (2008) *Crit. Rev. Ther. Drug Carrier Syst.* 25:403-47, PMID: 190626331; and Shaunak et al. (2006) *Nature Chemical Biology* 2:312-313. Alternatives exist for achieving similar stabilizing results. See, e.g., Schellenberger et al. (2009) *Nature Biotechnology* 27:1186-1192.

In general, pharmaceutical compositions can be prepared in various forms, such as granules, tablets, pills, capsules (e.g., adapted for oral delivery), suppositories, microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Formulations may incorporate stabilizing agents, wetting and emulsifying agents, salts for varying the osmotic pressure or buffers for securing an adequate pH value.

The pharmaceutical composition can comprise other components in addition to the bacteriocin polypeptide, e.g., more than one active ingredient, e.g., two or more, three or more, five or more, or ten or more different enzymes, where the different enzymes may be specific for the same, different, or accompanying bacteria. For example, the pharmaceutical composition can contain multiple (e.g., at least two or more) defined killing activities, wherein at least two of them in the composition have different bacterial host specificity or different specificity. In this manner, the therapeutic composition can be adapted for treating a mixed infection of different bacteria, or may be a composition selected to be effective against various types of infections found commonly in a particular institutional environment. A select combination may result, e.g., by selecting different groups of killing entities derived from various sources of differing specificity so as to target multiple strains present, or potentially present in the infection. As noted above, the killing activity can be administered in conjunction with other agents, such as a conventional antimicrobial agent or a reagent which provides for efficacy against biofilm or capsule forming cultures. Various materials are described, e.g., in Davies and Marques (2009) J. Bacteriology 191:393-403; Kimura and Itoh (2002) Appl. and Env. Microbiology 69:2491-2497; Kim and Geider (2000) Phytopathology 90:1263-1268; Hughes et al. (1998) J. Appl. Microbiology 85:583-590; and Bartell and Orr (1969) J. Virology 4:580-584. In some embodiments, an additive (e.g., fatty acid) or biofilm depolymerase may be added as an additional domain to the chimeric construct, as an additional component in a formulation, or administered in combination, simultaneously or sequentially, with the described bacteriocin killing activity. Combinations may improve or complement the killing activity selected.

VI. Methodology

Some aspects of practicing the present invention involve well-known methods general clinical microbiology, general methods for handling bacteriophage, and general fundamentals of biotechnology, principles and methods. References for such methods are listed below.

A. General Clinical Microbiology

General microbiology is the study of the microorganisms. See, e.g., Sonenshein et al. (ed. 2002) *Bacillus Subtilis and Its Closest Relatives: From Genes to Cells* Amer. Soc. Microbiol.; Alexander and Strete (2001) *Microbiology: A Photographic Atlas for the Laboratory* Benjamin/Cummings; Cann (2001) *Principles of Molecular Virology* (3d ed.); Garrity (ed. 2005) *Bergey's Manual of Systematic Bacteriology* (2 vol. 2d ed.) Plenum; Salyers and Whitt (2001) *Bacterial Pathogenesis: A Molecular Approach* (2d ed.) Amer. Soc. Microbiol.; Tierno (2001) *The Secret Life of Germs: Observations and Lessons from a Microbe Hunter* Pocket Star; Block (ed. 2000) *Disinfection, Sterilization, and Preservation* (5th ed.) Lippincott Williams & Wilkins Publ.; Cullimore (2000) *Practical Atlas for Bacterial Identification* Lewis Pub.; Madigan et al. (2000) *Brock Biology of Microorganisms* (9th ed.) Prentice Hall; Maier et al. (eds. 2000) *Environmental Microbiology* Academic Pr.; Tortora et al. (2000) *Microbiology: An Introduction* including Microbiology Place (TM) Website, Student Tutorial CD-ROM, and Bacteria ID CD-ROM (7th ed.), Benjamin/Cummings; Demain et al. (eds. 1999) *Manual of Industrial Microbiology and Biotechnology* (2d ed.) Amer. Soc. Microbiol.; Flint et al. (eds. 1999) *Principles of Virology: Molecular Biology, Pathogenesis, and Control* Amer. Soc. Microbiol.; Murray et al. (ed. 1999) *Manual of Clinical Microbiology* (7th ed.) Amer. Soc. Microbiol.; Burlage et al. (eds. 1998) *Techniques in Microbial Ecology* Oxford Univ. Press; Forbes et al. (1998) *Bailey & Scott's Diagnostic Microbiology* (10th ed.) Mosby; Schaechter et al. (ed. 1998) *Mechanisms of Microbial Disease* (3d ed.) Lippincott, Williams & Wilkins; Tomes (1998) *The Gospel of Germs: Men, Women, and the Microbe in American Life* Harvard Univ. Pr.; Snyder and Champness (1997) *Molecular Genetics of Bacteria* Amer. Soc. Microbiol., ISBN: 1555811027; Karlen (1996) *MAN AND MICROBES: Disease and Plagues in History and Modern Times* Touchstone Books; and Bergey (ed. 1994) *Bergey's Manual of Determinative Bacteriology* (9th ed.) Lippincott, Williams & Wilkins. More recent editions may be available.

B. General Methods for Handling Bacteriophage

General methods for handling bacteriophage are well known, see, e.g., Snustad and Dean (2002) *Genetics Experiments with Bacterial Viruses* Freeman; O'Brien and Aitken (eds. 2002) *Antibody Phage Display: Methods and Protocols* Humana; Ring and Blair (eds. 2000) *Genetically Engineered Viruses* BIOS Sci. Pub.; Adolf (ed. 1995) *Methods in Molecular Genetics: Viral Gene Techniques* vol. 6, Elsevier; Adolf (ed. 1995) *Methods in Molecular Genetics: Viral Gene Techniques* vol. 7, Elsevier; and Hoban and Rott (eds. 1988) *Molec. Biol. of Bacterial Virus Systems* (Current Topics in Microbiology and Immunology No. 136) Springer-Verlag.

C. General Fundamentals of Biotechnology, Principles and Methods

General fundamentals of biotechnology, principles and methods are described, e.g., in Alberts et al. (2002) *Molecular Biology of the Cell* (4th ed.) Garland; Lodish et al. (1999) *Molecular Cell Biology* (4th ed.) Freeman; Janeway et al. (eds. 2001) *Immunobiology* (5th ed.) Garland; Flint et al. (eds. 1999) *Principles of Virology: Molecular Biology, Pathogenesis, and Control*, Am. Soc. Microbiol.; Nelson et al. (2000) *Lehninger Principles of Biochemistry* (3d ed.) Worth; Freshney (2000) *Culture of Animal Cells: A Manual of Basic Technique* (4th ed.) Wiley-Liss; Arias and Stewart (2002) *Molecular Principles of Animal Development*, Oxford University Press; Griffiths et al. (2000) *An Introduction to Genetic Analysis* (7th ed.) Freeman; Kierszenbaum (2001) *Histology and Cell Biology*, Mosby; Weaver (2001) *Molecular Biology* (2d ed.) McGraw-Hill; Barker (1998) *At the Bench: A Laboratory Navigator* CSH Laboratory; Branden and Tooze (1999) *Introduction to Protein Structure* (2d ed.), Garland Publishing; Sambrook and Russell (2001) *Molecular Cloning: A Laboratory Manual* (3 vol., 3d ed.), CSH Lab. Press; and Scopes (1994) *Protein Purification: Principles and Practice* (3d ed.) Springer Verlag. More recent editions may be available.

D. Mutagenesis; Site Specific, Random, Shuffling

Based upon the structural and functional descriptions provide herein, homologs and functional variants can be generated. Segments with penetration functions can be found by structural homology. These may also serve as the starting points to screen for variants of the structures, e.g., mutagenizing such structures and screening for those which have desired characteristics, e.g., broader substrate specificity. Standard methods of mutagenesis may be used, see, e.g., Johnson-Boaz et al. (1994) *Mol. Microbiol.* 13:495-504; U.S. Pat. Nos. 6,506,602, 6,518,065, 6,521,453, 6,579,678.

E. Screening

Screening methods can be devised for evaluating mutants or new candidate killing segments.

Killing activity screens can use crude bacteria cultures, isolated substrate components, reactant preparations, synthetic substrates, or purified reagents to determine the affinity and number of substrate sites on target cells. Penetration assays can be incorporated to evaluate integrity of the outer membranes of target strains, lawn inhibition assays, viability tests of cultures, activity on target substrate preparations or other substrates, or release of components may be evaluated. For example, in a cell wall muralytic function assay, amidase activity may be measured by release of soluble N-acetyl hexose amines (e.g., modified Morgan-Elson reaction) or endopeptidase activity by assay for free amino groups (L-alanine for ala-gly endopeptidases, L-glycine for gly-gly endopeptidases) using a DNFB assay), all three of these assays based on Petit et al. (1966) Biochemistry 5:2764-76. Gly-gly endopeptidase activity can also be measured as the release of free amino groups from N-acetylated hexaglycine (acetyl-Gly6), see Kline et al. (1994) Anal. Biochem. 217: 329-331.

Linkers can be tested to compare the effects on membrane transfer or degradation, or to compare the activities of various orientations of the active fragments. Panels of targets (e.g., Gram-negative, Gram-positive, mycobacteria and spores) can be screened using killing segments to determine which fragments are critical or efficient on a broader or narrower spectrum of targets.

One method to test for, e.g., a cell wall degrading activity is to treat phage with mild detergents or denaturants to release proteins associated with the virion. These proteins are further tested for wall degrading or muralytic activity on bacterial cells. Another method is to determine cell wall degradation activity or lysis from without (LO) on a phage resistant host. A third method to assess wall degrading or muralytic activity associated with phage structural component is to perform Zymogram assays, e.g., where a pure phage preparation is electrophoresed on SDS-polyacrylamide gel incorporating autoclaved host cells. Proteins on the gels are allowed to renature in situ and then act upon the cell wall components giving rise to clear "muralytic" zones when the rest of the gel stains blue with methylene blue dye. See, e.g., Lepeuple et al, (1998) Appl. Environ. Microbiol. 64:4142-428. The clear zones are visualized and the protein band from each zone is eluted. The protein can be identified, e.g., by N-terminal sequencing or by Mass spectrometry. The coding sequence for the degrading protein can then be isolated.

VII. Isolation of Nucleic Acids Encoding Bacteriocins; Component Domains

The invention further provides nucleic acids that encode the killing segment or membrane transfer proteins. Such polynucleotides may encode, e.g., bacteriocins described herein, and other killing domains as described above.

Nucleic acids that encode killing segment polypeptides are relevant to the nucleic acid embodiments of the invention. These nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). Besides synthetic methodologies, a wide variety of cloning and in vitro amplification methodologies are well-known to persons of skill. Examples of these techniques and instructions sufficient to direct persons of skill through many cloning exercises are found in Berger and Kimmel, Guide to Molecular Cloning Techniques, Methods in Enzymology 152 Academic Press, Inc.; Sambrook et al. (1989) Molecular Cloning—A Laboratory Manual (2nd ed.) Vol. 1-3, Cold Spring Harbor Laboratory, Cold Spring Harbor Press; Current Protocols in Molecular Biology, Ausubel et al., eds., Current Protocols (Greene Publishing Associates, Inc. and John Wiley & Sons, Inc., 1994 Supplement); Cashion et al., U.S. Pat. No. 5,017,478; and Carr, European Patent No. 0246864.

A DNA that encodes a cargo domain can be prepared by a suitable method described above, including, e.g., cloning and restriction of appropriate sequences with restriction enzymes. Nucleic acids encoding a desired killing segment can be isolated by routine cloning methods. An exemplary nucleotide sequence of, e.g., a cell wall degrading polypeptide, e.g., in Accession Number YP_024486, can be used to design probes that specifically hybridize to a gene; or to an mRNA, encoding a killing protein or segment, in a total nucleic acid sample (e.g., in a Southern or Northern blot). Once the target nucleic acid encoding the killing protein or segment is identified, it can be isolated according to standard methods known to those of skill in the art. Further, the isolated nucleic acids can be cleaved with restriction enzymes to create nucleic acids encoding the full-length killing polypeptide, or subsequences thereof, e.g., containing subsequences encoding at least a subsequence of a catalytic domain of a killing polypeptide. These restriction enzyme fragments, encoding a killing polypeptide or subsequences thereof, can then be ligated, for example, to produce a nucleic acid encoding a killing polypeptide.

Similar methods can be used to generate appropriate linkers between fragments.

A nucleic acid encoding an appropriate polypeptide, or a subsequence thereof, can be characterized by assaying for the expressed product. Assays based on the detection of the physical, chemical, or immunological properties of the expressed polypeptide can be used. For example, one can identify a killing segment polypeptide by the ability of a polypeptide encoded by the nucleic acid to kill target bacterial cells, e.g., as described herein Also, a nucleic acid encoding a desired polypeptide, or a subsequence thereof, can be chemically synthesized. Suitable methods include the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding a desired polypeptide, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired polypeptide or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the cargo polypeptide or a polypeptide subsequence thereof by site-directed mutagenesis. The plasmid containing a cargo polypeptide-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al. (1987) U.S. Pat. No. 4,683,202; PCR Protocols A Guide to Methods and Applications (Innis et al., eds) Academic Press Inc. (1990); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87, 1874; Lomeli et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117.

Some nucleic acids encoding cargo polypeptides can be amplified using PCR primers based on the sequence of the identified polypeptides.

Other physical properties, e.g., of a recombinant cargo polypeptide expressed from a particular nucleic acid, can be compared to properties of known desired polypeptides to provide another method of identifying suitable sequences or domains, e.g., of the cargo proteins that are determinants of bacterial specificity, binding specificity, and/or catalytic activity. Alternatively, a cargo polypeptide encoding nucleic acid or recombinant cargo polypeptide gene can be mutated, and its role as a cargo polypeptide, or the role of particular sequences or domains established by detecting a variation in bacterial "function" normally enhanced by the unmutated, naturally-occurring, or control cargo polypeptide. Those of skill will recognize that mutation or modification of killing polypeptides of the invention can be facilitated by molecular biology techniques to manipulate the nucleic acids encoding the polypeptides, e.g., PCR. Other mutagenesis or gene shuffling techniques may be applied to the functional fragments described herein, including linker features compatible with chimeric constructs.

Functional domains of newly identified killing polypeptides can be identified by using standard methods for mutating or modifying the polypeptides and testing them for activities such as acceptor substrate activity and/or catalytic activity, as described herein. The sequences of functional domains of the various killing proteins can be used to construct nucleic acids encoding or combining functional domains of one or more killing polypeptides. These multiple activity polypeptide fusions can then be tested for a desired bacteriostatic or bacteriolytic activity. Particular examples of sources for killing polypeptides include prophage sequences, including incomplete remnants of functional phage genomes, or pyocin-like structures, including particles derived from phage-like genetic segments, e.g., deletion or mutated genetic remnants of phage remaining in the DNA of a bacterium.

Nucleic acids encoding killing polypeptides can be identified by alignment and comparison with known nucleic acid or amino acid sequences of killing polypeptides, e.g., to determine the amount of sequence identity between them. This information can be used to identify and select polypeptide domains that confer or modulate killing polypeptide activities, e.g., target bacterial or binding specificity and/or degrading activity based on the amount of sequence identity between the polypeptides of interest. For example, domains having sequence identity between the killing polypeptides of interest, and that are associated with a known activity, can be used to construct polypeptides containing that domain and other domains, and having the activity associated with that domain (e.g., bacterial or binding specificity and/or killing activity). Similar strategies may be applied to isolate appropriate domains or motifs, or to linkers for spacing between domains.

VIII. Expression of Desired Polypeptides in Host Cells

The proteins described herein can be expressed in a variety of host cells, including *E. coli*, other bacterial hosts, and yeast. The host cells can be microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus, Staphylococcus*, and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T candida, T. sphaerica, T. xylinus, T. famata*, and *T. versatilis*), Debaryomyces (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and Brettanomyces (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*. Eukaryotic cells, e.g., CHO or yeast cells, can also be used for production.

Once expressed in a host cell, the chimeric bacteriocin constructs can be used to prevent growth or kill target bacteria. In some embodiments, the described bacteriocin construct is used to decrease growth of a Gram-negative bacterium. In some embodiments, the protein is used to decrease growth of a *Klebsiella, Pseudomonas*, e.g., *Pseudomonas aeruginosa*, or *Escherichia* bacterium. Fusion constructs combining such fragments can be generated, including fusion proteins comprising a plurality of killing activities.

Typically, a polynucleotide that encodes the bacteriocin or chimeric bacteriocin construct is placed under the control of a promoter that is functional in the desired host cell. An extremely wide variety of promoters is well known, and can be used in expression vectors of the invention, depending on the particular application. Ordinarily, the promoter selected depends upon the cell in which the promoter is to be active. Other expression control sequences such as ribosome binding sites, transcription termination sites, etc., can be included. Constructs that include one or more of these control sequences are termed "expression cassettes." Accordingly, the invention provides expression cassettes into which the nucleic acids that encode fusion proteins, e.g., combining a killing fragment with an outer membrane translocating fragment, are incorporated for expression in a desired host cell.

Expression control sequences that are suitable for use in a particular host cell can be obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer et al., Proc. Natl. Acad. Sci. U.S.A. (1983) 80:21-25); and the lambda-derived $P_L$ promoter and N-gene ribosome binding site (Shimatake et al., Nature (1981) 292: 128.

For expression of bacteriocins or chimeric bacteriocin constructs in prokaryotic cells other than *E. coli*, a promoter that functions in the particular prokaryotic production species is used. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An exemplary RBS in *E. coli* consists of a nucleotide sequence 3-9 nucleotides in length located 3-11 nucleotides upstream of the initiation codon (Shine and Dalgarno (1975) Nature 254:34; Steitz, In Biological regulation and development: Gene expression (ed. R. F. Goldberger), vol. 1, p. 349, 1979, Plenum Publishing, NY).

For expression of proteins in yeast, convenient promoters include GAL1-10 (Johnson and Davies (1984) Mol. Cell. Biol. 4:1440-1448) ADH2 (Russell et al. (1983) J. Biol.

Chem. 258:2674-2682), PHO5 (EMBO J. (1982) 6:675-680), and MFα (Herskowitz and Oshima (1982) in The Molecular Biology of the Yeast Saccharomyces (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., Gene 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., EMBO J. 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous polypeptides slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the desired polypeptide. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) Gene 25: 167; de Boer et al. (1983) Proc. Nat'l. Acad. Sci. USA 80: 21), and the bacteriophage T7 promoter (Studier et al. (1986) J. Mol. Biol.; Tabor et al. (1985) Proc. Nat'l. Acad. Sci. USA 82: 1074-8). These promoters and their use are discussed in Sambrook et al., supra.

The construction of polynucleotide constructs generally requires the use of vectors able to replicate in bacteria. A plethora of kits are commercially available for the purification of plasmids from bacteria (see, e.g., EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a polypeptide, necessary for the survival or growth of transformed host cells grown in a selective culture medium. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill.

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

Expression vectors can be introduced into a chosen host cell using standard methods known to those of skilled in the art. For example, the expression vectors can be introduced into prokaryotic cells, including *E. coli*, by calcium chloride transformation, and into eukaryotic cells by calcium phosphate treatment or electroporation.

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et al. (1988), J. Biol. Chem. 263: 16297-16302.

The various polypeptides of the invention can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al. (1984) Bio/Technology 2:800; Schoner et al. (1985) Bio/Technology 3:151). In embodiments in which the polypeptide is secreted, either into the periplasm or into the extracellular medium, the DNA sequence is often linked to a cleavable signal peptide sequence. The signal sequence directs translocation of the fusion polypeptide through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al. (1985) Proc. Natl. Acad. Sci. USA 82:7212; Talmadge et al. (1980) Proc. Natl. Acad. Sci. USA 77:3988; Takahara et al. (1985) J. Biol. Chem. 260: 2670). In another embodiment, the fusion polypeptides are fused to a subsequence of protein A or bovine serum albumin (BSA), for example, to facilitate purification, secretion, or stability. Affinity methods, e.g., using substrate for the catalytic fragment may be appropriate.

The bacteriocin polypeptides of the invention can also be further linked to other polypeptide segments, e.g., biofilm depolymerase segments. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series. For certain applications, it may be desirable to cleave extraneous sequence from the fusion polypeptide after purification. This can be accomplished by any of several methods known in the art, including cleavage by cyanogen bromide, a protease, or by Factor $X_a$ (see, e.g., Sambrook et al., supra.; Itakura et al. (1977) Science 198:1056; Goeddel et al. (1979) Proc. Natl. Acad. Sci. USA 76:106; Nagai et al.

(1984) Nature 309:810; Sung et al. (1986) Proc. Natl. Acad. Sci. USA 83:561). Cleavage sites can be engineered into the gene for the fusion polypeptide at the desired point of cleavage.

More than one recombinant polypeptide may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al (1989) *Biotechnology* 7:698-704. In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

IX. Purification of Desired Polypeptides

A crude cellular extract containing the expressed intracellular or secreted polypeptides described herein can be used in the methods of the present invention.

The bacteriocin polypeptides can also be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)). Because the degrading segments, at least, derive from phage proteins selected for stability, purification can involve denaturation of contaminating materials. Substantially pure compositions are typically about 70, 75, 80, 85, 90, 92, 95, 98 to 99% or higher homogeneous. The purified polypeptides can also be used, e.g., as immunogens for antibody production, which antibodies may be used in immunoselection purification methods.

To facilitate purification of the polypeptides of the invention, the nucleic acids that encode them can also include a coding sequence for an epitope or "tag" for which an affinity binding reagent is available, e.g., a purification tag. Examples of suitable epitopes include the myc and V-5 reporter genes; expression vectors useful for recombinant production of fusion polypeptides having these epitopes are commercially available (e.g., Invitrogen (Carlsbad CA) vectors pcDNA3.1/Myc-His and pcDNA3.1/V5-His are suitable for expression in mammalian cells). Additional expression vectors suitable for attaching a tag to the polypeptides of the invention, and corresponding detection systems are known to those of skill in the art, and several are commercially available (e.g., FLAG, Kodak, Rochester NY). Another example of a suitable tag is a polyhistidine sequence, which is capable of binding to metal chelate affinity ligands. Typically, six adjacent histidines are used, although one can use more or fewer than six. Suitable metal chelate affinity ligands that can serve as the binding moiety for a polyhistidine tag include nitrilo-tri-acetic acid (NTA) (Hochuli (1990) Genetic Engineering: Principles and Methods, J. K. Setlow, Ed., Plenum Press, NY; commercially available from Qiagen (Santa Clarita, CA)). Purification tags also include maltose binding domains and starch binding domains. Purification of maltose binding domain proteins is known to those of skill in the art.

Other haptens that are suitable for use as tags are known to those of skill in the art and are described, for example, in the Handbook of Fluorescent Probes and Research Chemicals (6th Ed., Molecular Probes, Inc., Eugene OR). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that certain modifications can be made to the catalytic or functional domains of the bacteriocin polypeptides without diminishing their biological activity. Some modifications can be made to facilitate the cloning, expression, or incorporation of the catalytic domain into a fusion polypeptide. Such modifications are well known to those of skill in the art and include, for example, the addition of codons at either terminus of the polynucleotide that encodes the catalytic domain, e.g., a methionine added at the amino terminus to provide an initiation site, or additional amino acids (e.g., poly His) placed on either terminus to create conveniently located restriction enzyme sites or termination codons or purification sequences.

The following discussion of the invention is for the purposes of illustration and description, and is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. All publications, patents, patent applications, Genbank numbers, and websites cited herein are hereby incorporated by reference in their entireties for all purposes. Later versions of textbooks may include more recent methodologies.

EXAMPLES

Example I: *Klebsiella* Type Bacteriocins; Klebicins

Klebicins are high molecular weight (>30 kDa) bacteriocins produced by *Klebsiella* spp. Like other bacteriocins, klebicins are also modular proteins having three domains. Although Klebicins such as Klebicin B, C, CCL, and D were sequenced and some of them were proposed to be used for epidemiological typing of *Klebsiella* strains, very little is known about their antibacterial properties.

P628 (Wild-type Klebicin CCL):

Klebicin CCL is identical to bacteriocin Cloacin DF13, which is produced by *Enterobacter cloacae*. Cloacin DF13 utilizes the Tol-ABQR pathway for translocation and employs LutA as a cell surface receptor. The receptor for the Klebicin is expected to be modulated by the presence of iron. The bacteria uses siderophores to scavenge iron from the environment and these siderophores enter the cell using the receptor expressed on the cell surface.

The near-identity of DF13 and klebicin CCL suggest that the Tol pathway and the LutA receptor are shared between these species. The klebicin CCL is expected to be a nuclease with specific degradation of rRNA. Since LutA is distributed as a cell surface receptor in many Enterobacteriacea, the klebicin CCL might have broad killing range. The receptor for the Klebicin is expected to be modulated by the presence of iron. The bacteria uses these receptors to scavenge iron from the environment by releasing siderophores and these siderophores enter the cell using the receptor expressed on the cell surface.

Based on the published DNA sequence (AF190857.1), we isolated Klebicin CCL from *Klebsiella* spp. in GangaGen bacterial collection and cloned into an *E. coli* expression vector along with its immunity gene for heterologous expression.

Screening of Klebcin CCL Immunity Gene in *Klebsiella* Strains:

Primers were designed to screen for the presence of klebicin CCL, using the sequence available form the database. Since the immunity gene is a small product and always associated with the klebicin, immunity gene PCR was done. Several clinical *Klebsiella* spp. isolates were screened by colony PCR. Out of the 19 isolates tested, 4 were positive for immunity gene and these four strains are expected to harbour the klebicin CCL gene. The results are shown in Table 4. Strain B2092 was used for isolating the CCL gene for cloning.

TABLE 4

| Strains | Klebicin CCL Immunity PCR |
| --- | --- |
| B2092 | + |
| B2093 | − |
| NDM KL1 | − |
| NDM KL2 | + |
| B2095 | − |
| MTCC 109 | − |
| B2091 | − |
| B2107 | − |
| NDM KL3 | + |
| NDM KL5 | − |
| B2063 | + |
| B2062 | − |
| B2023 | − |
| B2058 | − |
| B236 | − |
| B2007 | − |
| B2108 | − |
| B2094 | − |
| NDM KL7 | − |

Cloning and Expression of Klebicin CCL:

The gene encoding the klebicin CCL along with its immunity gene was PCR amplified from *Klebsiella* strain B2092 and cloned into *E. coli* expression vector pET26b at NdeI-XhoI site, for expression in native form without any affinity tags. *E. coli* transformants were screened by PCR, plasmid DNA isolated from the positive clones and presence of the insert confirmed by restriction digestion analysis.

5 out of the 6 clones tested released the cloned insert of ~1.9 kb. The clones were sequence confirmed and test protein expression was done.

Protein Expression:

Test protein expression was performed in *E. coli* ER2566 by inducing with 1 mM IPTG at 37° C. for 4 hours. The expected size of fusion protein is ~60 kDa. After 4 hrs of IPTG induction, the cells were pelleted, resuspended in 20 mM sodium phosphate buffer pH 7 and sonicated to lyse the cells. The soluble and insoluble fraction of the cells was separated by centrifugation at 10000 rpm for 15 minutes. The supernatant and pellets were analyzed on a 12% acrylamide gel.

Clones 1, 3, and 4 expressed the protein of interest and is exclusively present in the soluble form. Clone #1 was designated as pGDC 628.

Purification of P628:

Since the P628 was expressed without any affinity tag, it was purified by conventional ion-exchange chromatography. Briefly, the sonicated supernatant fration was passed through anion exchange chromatography matrix, UnoQ and the flowthrough was collected. The collected flowthough was then loaded onto a cation exchange chromatography matrix, UnoS. The protein bound matrix was washed and the protein was eluted with increasing concentration of NaCl containing buffer. A step gradient elution with 100 mM, 300 mM, 500 mM and 1M NaCl was done and the samples were analyzed on a 12% acrylamide gel.

P628 bound to the cation exchange matrix and the bound protein was eluted in 300 and 500 mM NaCl. These fractions were dialyzed against 20 mM SPB pH 7.0 separately overnight to remove NaCl. Protein concentration was estimated by Bradford assay, 1 mg/ml and 1.3 mg/ml.

Activity of Purified P628:

The antibacterial activity of the purified P628 was determined by three assays—a) lawn inhibition assay, b) CFU drop assay and c) MIC assay.

a) Lawn Inhibition Assay

Lawn inhibition assay is a simple qualitative assay to determine the antibacterial activity of a test protein. In this assay, a bacterial lawn using a test isolate is made on LB agar plate and a defined concentration of the test protein is placed on the lawn, air dried, and incubated at 37° C. for 16-18 hrs. A positive result would indicate a clear inhibition zone on the lawn.

Since the cell surface receptor LutA is present in Enterobacteriacea family, the P628 was tested on lawns of *Klebsiella* spp. isolates and *E. coli* isolates. P628 was tested on 69 *Klebsiella* spp. clinical isolates and 41 *E. coli* clinical isolates. 20 μL of 1 mg/mL (20 μg) P628 was placed on the lawns of the clinical isolates made on LB agar. The plates were incubated at 37° C. for 16-18 hrs.

The P628 showed inhibition zone on 85 *Klebsiella* isolates corresponding to 70% of the total tested isolates and 6 *E. coli* isolates corresponding to 15% of the tested isolates. The lysis zone on lawns were variable with very clear lysis zones (rated 3+), moderate lysis zones (rated 2+) and turbid lysis zones (1+). The percentage is represented in table 5 below.

TABLE 5

Total Klebsiella isolates tested - 102
Sensitive isolates - 78/102 (76%)
*E. coli* isolates tested - 71
Sensitive isolates - 20/71 (28%)

P628 shows lysis on 76% of the tested *Klebsiella* spp., suggesting that this could be a potent protein. Although the LutA receptor is distributed in *E. coli* as well, only 28% of the tested *E. coli* strains are sensitive to P628.

b) CFU Drop Assay:

The antibacterial activity of P628 was tested against *Klebsiella pneumoniae* clinical isolate B2094 in both LB media and Fetal Bovine Serum (FBS). Briefly, ~$10^6$ cells/mL of B2094 were resuspended in LB or FBS and treated with 100 and 200 μg/mL of P628 in 20 mM SPB pH 7.0 in a volume of 200 μL. The reaction mixture was incubated at 37° C. for 2 hours and the remaining number of viable cells were enumerated by dilution plating on LB plates and incubated at 37° C. for 18 hrs.

P628 killed *K. pneumoniae* in both LB and FBS. However, the activity was much better in FBS with ~4 logs cell killing obtained in FBS and 1 log cell killing in LB media. The results are shown in FIG. 1.

P628 has potent antibacterial activity against clinical *K. pneumoniae* strain B2094 and it is active in serum.

c) CFU Drop Assay with Additional Strains:

CFU drop assay with additional strains were done in growth media and FBS. In this assay, antibacterial activity of P628 was tested on two additional clinicals isolates of *K. pneumoniae*, B2064 and B2065. These strains were treated with 200 μg/mL of P628 in Cation adjusted Muller Hinton Broth (CA-MHB medium), 50% FBS and 75% FBS. The reaction mixture was incubated at 37° C. for 2 hours and the remaining number of viable cells were enumerated by dilution plating on LB plates and incubated at 37° C. for 18 hrs.

Figure 2A:
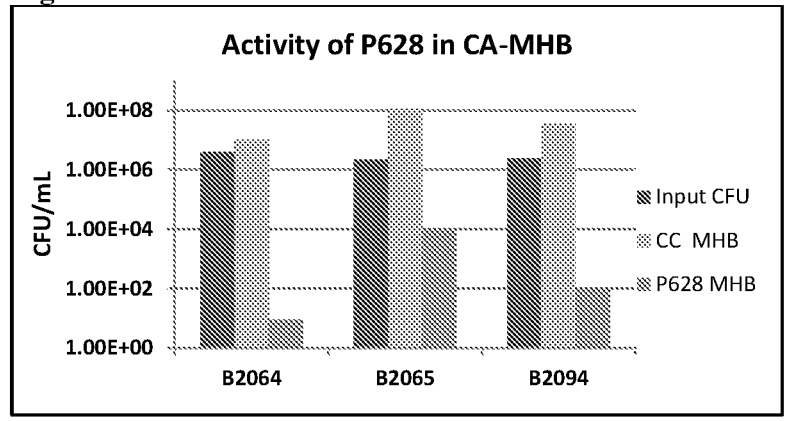
FIGS. 2A-2B show activity of P628 in CA-MHB (FIG. 2A) and FCS (FIG. 2B).
Figure 2B:
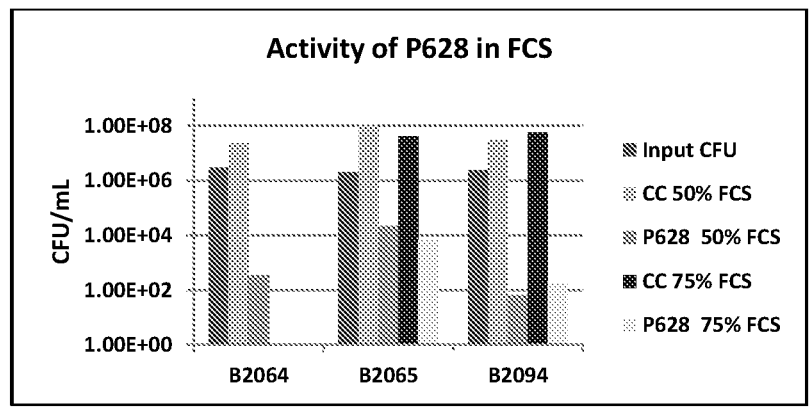

P628 is active in both CA-MHB and FBS on tested isolates with at least 2 logs cell killing obtained in both media (FIGS. 2A and 2B)

P628 demonstrates potent antibacterial activity against tested *K. pneumoniae* clinical isolates.

d) MIC:

Minimum inhibitory concentration (MIC) was determined using a modified Clinical and Laboratory Standards Institute (CLSI) broth microdilution procedure on *K pneumoniae* strain 2094 in CA-MHB, Casamino acids media (CAA) and FBS. A 10-point MIC was set up in microtitre plates in duplicates with two-fold dilutions starting at 875 μg/mL. Each well was inoculated with $5\times10^5$ cells of the test isolate. Microtiter plates were incubated at 35° C. for 18-20 hrs. The endpoint for this assay was complete inhibition of growth at the end of incubation as determined by colorless wells after addition of Iodonitro tetrazolium (INT) dye.

MIC was obtained at 100 μg/mL in CA-MHB, 14 μg/mL in CAA and 219 μg/mL in FBS on strain B2094.

Better MIC was obtained with CAA and FBS, indicating that P628 works better in iron replete conditions.

e) MIC on Additional Clinical Isolates:

16 additional clinical strains that are resistant to several antibiotics were tested for sensitivity to P628 by MIC in both CAMHB and FBS. The results are shown in Table 6

TABLE 6

| Isolates | Antibiogram | MIC at 6 h (μg/mL) | |
| --- | --- | --- | --- |
| | | CAMHB | 50% FBS |
| B2135 | Amp | 2.7 | 1.4 |
| B2437 | Amp, Amox, Cefuroxime, Ceftriaozone, Cefepime | 1.4 | <0.3 |
| B2138 | Ampicillin, cefuroxime, Ceftriaozone | 5.4 | 1.4 |
| B2139 | Ampicillin, Amoxicillin, Cefuroxime, Ceftriaozone, Gentamicin, Ciprofloxacin, Trimithoprim | 1.4 | <0.4 |
| B2143 | Ampicillin | 1.4 | <0.4 |
| B2152 | Ampicillin, Trimithoprim | 5.5 | 1.4 |
| B2153 | Ampicillin | 44 | 2.7/1.4 |
| B2154 | Ampicillin | 22 | 0.3 |
| B2157 | Ampicillin | 0.68 | 0.08 |
| ATCC 13883 | QC strain | 0.3 | <0.02 |
| B2107 | Ampicillin, Amoxicillin, Cefozitin, Cefilotine, Gentamicin, cefixime, Trimithoprim, Ticaricillin, Pipericillin, ceftazidime, Ceftriaxome, Ertapenem, Amikacin, Ciprofloxacin, Norfloxaccin | 87.5 | 44 |
| B2128 | Ampicillin | 350 | 5.4 |
| B2129 | Ampicillin, Ticaricillin, cefalotin, Cefixime, Ceftrioxone, Gentamicin, Nalidixic acid, Ciprofloxacin, Norfloxacin, Trimethoprim | 11 | 0.7 |

TABLE 6-continued

| Isolates | Antibiogram | MIC at 6 h (μg/mL) | |
| --- | --- | --- | --- |
| | | CAMHB | 50% FBS |
| B2162 | Not available | 0.7 | <0.3 |
| B2105 | Ampicillin, Amoxicillin, Cefozitin, Cefilotine, Gentamicin, Cefixime, Trimithoprim, Ticaricillin, Pipericillin, Ceftazidime, Ceftriaxome, Ertapenem, Amikacin, Ciprofloxacin, Norfloxaccin | 175 | 11 |
| B2163 | Not available | 11 | 44 |

Drug-resistant clinical *K. pneumoniae* clinical isolates are sensitive to P628.

f) Dose Response of P628 on *K. pneumoniae*:

The dose response of P628 in fetal calf serum (FCS) was evaluated with two *K. pneumoniae* strains using the CFU drop assay. Briefly, ~$10^6$ cells in 50% FCS at varying concentrations of protein was incubated at 37° C. for 2 hours and remaining number of viable cells were enumerated by plating on LB plates. The experiment was setup in duplicates and the results plotted as average of duplicates.

Figure 3:
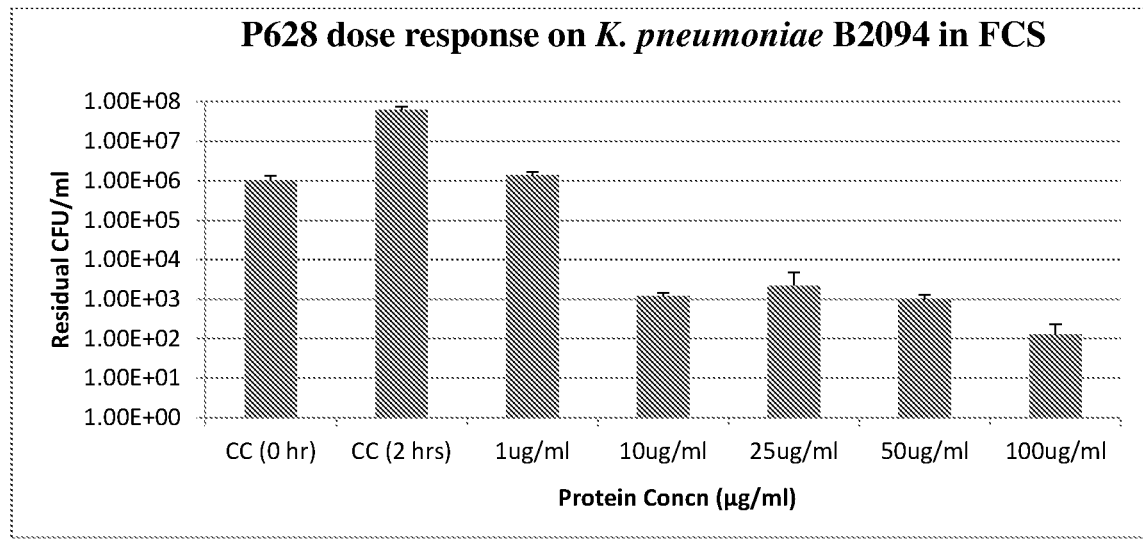
FIG. 3 shows P628 dose response on *K. pneumoniae* B2094 in FCS.

A dose response was performed on a clinical isolate of *K. pneumoniae*, B2094, isolated from a patient. P628 in the concentration range of 100 μg/ml to 1 μg/ml was used. The results are shown in FIG. 3.

While 1 μg/mL demonstrated a static effect, 3 log cell killing was obtained with 10 μg/mL of P628. With this strain, the killing seemed to be saturated at 10 μg/mL with similar killing obtained with 25, 50 and 100 μg/mL.

Figure 4:
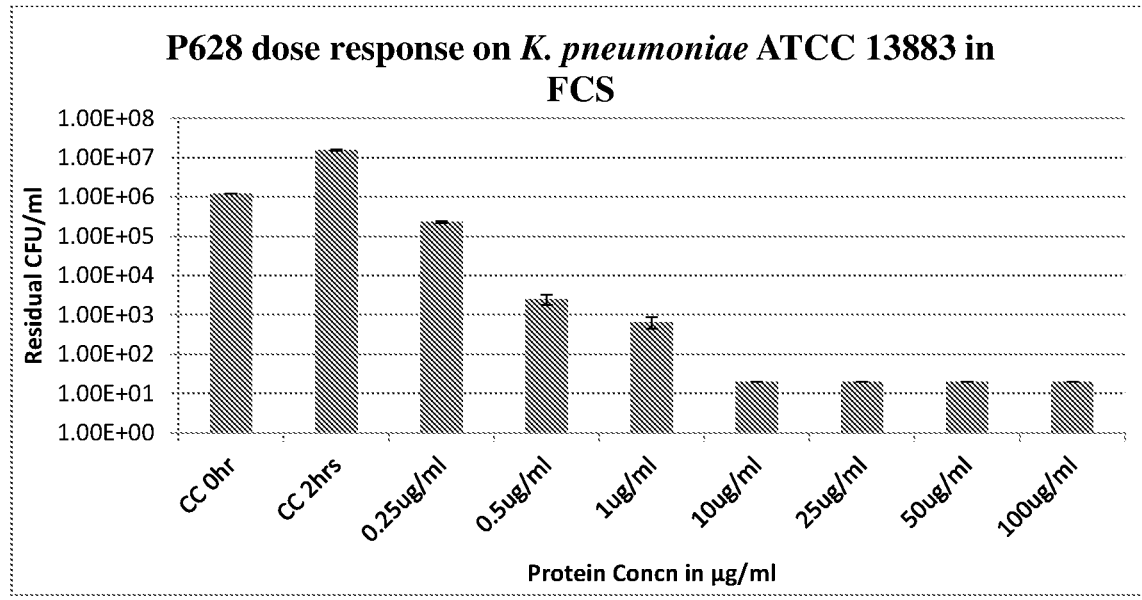
FIG. 4 shows P628 dose response on *K. pneumoniae* ATCC 13883 in FCS.
Figure 5:
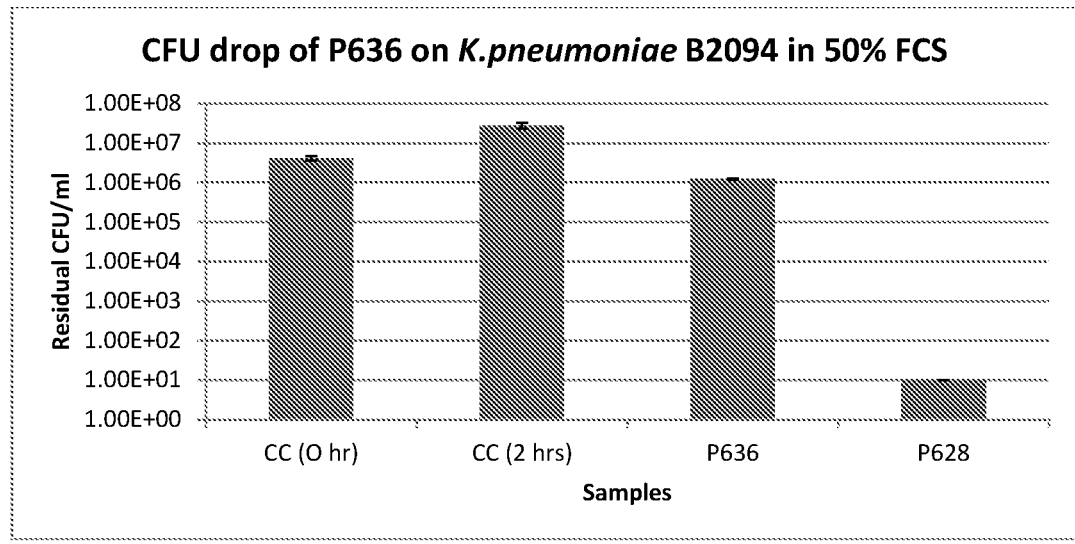
FIG. 5 shows CFU drop of P636 on *K. pneumoniae* B2094 in 50% FCS.

*K. pneumoniae* ATCC 13883 is a quality control strain for testing antibiotics and is highly sensitive to P628. P628 concentration of 100 μg/ml to 0.25 μg/ml was used. The results are shown in FIG. 4.

A dose-depended killing was obtained on ATCC 13883 with ~1 log cell killing obtained with 0.25 μg/ml. More than 5 log cell killing was obtained with 10 μg/ml of P628.

Example II: Evaluation of In Vivo Efficacy of P628 in Neutropenic Mouse Model of K. Pneumoniae Lung Infection A standard neutropenic mouse model of *Klebsiella pneumoniae* lung infection model was used for this study (W. A. Craig and D. R. Andes. 2008. In Vivo Pharmacodynamics of Ceftobiprole against Multiple Bacterial Pathogens in Murine Thigh and Lung Infection Models. Antimicrob. Agents And Chemother. 52, [10] 3492-3496)

Six to eight weeks old female BALB/c mice were rendered neutropenic by administration of cyclophosphamide. These immunocompromised mice were challenged intranasally with $10^6$ CFU of *Klebsiella pneumoniae* strain ATCC13883. At 2 hours post-infection, a group of animals were treated with P628 at 27 mg/kg via intravenous (IV) route, another group treated with 50 microliters of P628 at 0.27 mg via intranasal route and another group treated with ciprofloxacin at 10 mg/kg by oral route. In groups treated with IV P628 and ciprofloxacin, the treatment regimen was once in 12 hours for three days and the treatment regimen for group treated with intranasal P628 was once a day up to three days. All the animals in the infection control succumb to lung infection by 72 hours. While treatment of animals with intranasal administration of P628 completely protected the animals from lethal lung infection giving 100% protection, only one animal died in the group treated with IV P628 giving 83% protection. Treatment with oral ciprofloxacin also completely protected the mice from lethal infection. The results are presented in Table 7.

TABLE 7

| Group | Dosage and route | Survival (%) at 72 hours post-infection |
|---|---|---|
| Infection Control [~$10^6$ CFU/animal, intranasal] | Vehicle: IV | 0 |
| Infection + Reference standard | Ciprofloxacin (10 mg/kg, p.o.) | 100 |
| P628 Only, IV | 5 ml/kg [~27 mg/kg], IV | 100 |
| Infection plus P628 [IV] | 5 ml/kg [~27 mg/kg], IV | 83 |
| Infection plus P628 [Intranasal] | 50 µl per dose [~270 µg], intranasal | 100 |

P628 administered via both intranasal and intravenous routes protected the mice from *K. pneumoniae* induced lethal lung infection. P628 is efficacious in this animal model.

Example III: P636: Klebicn CCL TD Rd—Klebicin B KD

Introduction

Bacteriocins are a diverse family of protein antibiotics produced by bacteria, which kill members of the same or closely related species. There are few reports of bacteriocins (klebicins) from *Klebsiella* spp., none of them have been characterized and nothing is known about their antibacterial properties. Klebicins have been used for the purpose of typing *Klebsiella* spp for many decades, but have not been characterized in terms of their antibacterial properties in vitro or in vivo.

These proteins exert their antibacterial activity in a very specific manner by binding to a receptor and translocating into periplasm or cytoplasm where the killing domain of the klebicin exerts bactericidal effect by virtue of its DNAse/RNase activity. The domain organization in klebicins comprises of translocation domain, receptor binding domain and killing domain. The reason behind lack of killing in certain strains is due to either absence of a receptor or presence of an immunity protein. Hence, it should be possible to extend the host range by replacing the killing domain of the klebicin by a similar domain which cannot be neutralized by the immunity protein.

Klebicin CCL has RNase activity and is produced by *Klebsiella* spp. It has greater than 99% sequence homology with a bacteriocin, cloacin DF13 from *Enterobacter cloacae*. Klebicin B has DNase activity and is produced by *Klebsiella* spp. The strategy was to replace the killing domain of Klebicin CCL with a killing domain of Klebicin B to overcome the immunity problem thus increasing the antibacterial host range with this chimeric molecule.

Generating Klebicin CCL (Translocating Domain-Receptor Binding Domain)—Klebicin B (Killing Domain): Cloning Strategy:

The klebicin CCL translocating domain (TD)-receptor binding domain (RBD) was PCR amplified and fused to the PCR amplified product of Klebicin B killing domain (KD) along with the klebicin B immunity protein (The immunity protein is only transcriptionally fused and is essential for the expression of the fusion protein) by overlap extension PCR. The resulting PCR product was cloned into pET26b as NdeI-XhoI.

The clones were sequence confirmed and labelled as pGDC 636, Klebicin CCL (translocating domain-receptor binding domain)—Klebicin B (Killing domain)

Protein Expression Studies:

Protein expression was done in *E. coli* ER2566 by inducing with 1 mM IPTG at 37° C. at 0.8° Da) for 4 hours and checked on SDS-PAGE.

To determine if the protein was soluble, the cell pellet was sonicated, the supernatant and pellet separated by centrifugation and loaded on SDS-PAGE. The protein was observed in the supernatant fraction Induced protein cell pellet was resuspended in buffer, sonicated to lyse the cells, separated supernatant and pellet by centrifugation at 10,000 rpm. Protein purification was done from soluble fraction by anion exchange chromatography (unoQ) with Sodium phosphate buffer (pH 7) to retain the contaminating proteins on the matrix and allowing the protein of interest to flow through followed by cation Exchangechromatography (unoS) Sodium phosphate buffer (pH 7) with elution with sodium chloride. The protein purified to ~90% homogeneity Bactericidal Activity of P636 on *K. pneumoniae* 2094:

The antibacterial activity of P636 was tested using the CFU drop assay. ~$10^6$ cells in Cas amino acid (CAA) broth and 50% FCS at 200 µg/ml, was incubated at 37° C. for 2 hours and remaining number of viable cells were enumerated. The experiment was setup in duplicates and the results tabulated as average of duplicates. The results are shown in FIG. 5. P636 was active in CAA and showed 4 logs drop, however in 50% it did not show any significant drop in cfu.

Cell Binding Activity of P636:

Cell binding assays were carried out to determine the binding potential of P636 to *K. pneumoniae* cells. Cells of *Klebsiella pneumoniae* B2094 ($10^8$ cells) in 10 mM SPB containing 150 mM saline were incubated with protein P636 at 10 µg and incubated at 37° C. for 30 minutes, vials were centrifuged at 10,000 rpm to pellet cells and the cell pellet was washed with buffer. The supernatant and pellet were loaded on SDS-PAGE. Protein alone without cells were maintained as controls. P636 was observed in the supernatant indicating that the protein was soluble in the assay buffer. In addition, P636 observed in the supernatant indicating that the protein did not bind to cells under the conditions tested.

Example IV S5 Pyocin—Lysozyme Chimeric Fusions

Introduction

Bacteriocins are proteinaceous molecules produced by bacteria to kill closely related bacteria. Several bacteriocins are known, e.g.: Colicins, pyocins, pesticins, etc. Pyocins are bacteriocins produced by more than 70% of *Pseudomonas* spp. The high molecular weight pyocins are the R-type and F-type pyocins and the small molecular weight pyocins are the S-type pyocins. The specificity for the entry of S-type pyocins is determined by a receptor present on the cell surface. These receptors are utilized by the cell for the uptake of iron and referred to as iron-siderophore receptors. The domain organization of S-type pyocins are receptor binding domain (RD), translocation domain (TD), and killing domain (KD).

Cloning of S-Type Pyocins and S-Type Pyocin—Lysozyme Chimeric Fusions:

S-type pyocins and fusions of S-type pyocin translocation domain and binding domain with lysozyme domains (peptidoglycan degrading domains) were achieved by cloning into pET26b plasmid and sequence confirmed. The source of lysozyme domains were from:
   a. GP36 CD from *P. aeruginosa* phage P134
   b. Phi29 lysozyme from *B. subtilis* phage Phi29
   c. BP7e lysozyme from *E. coli* phage BP7

Figure 6:
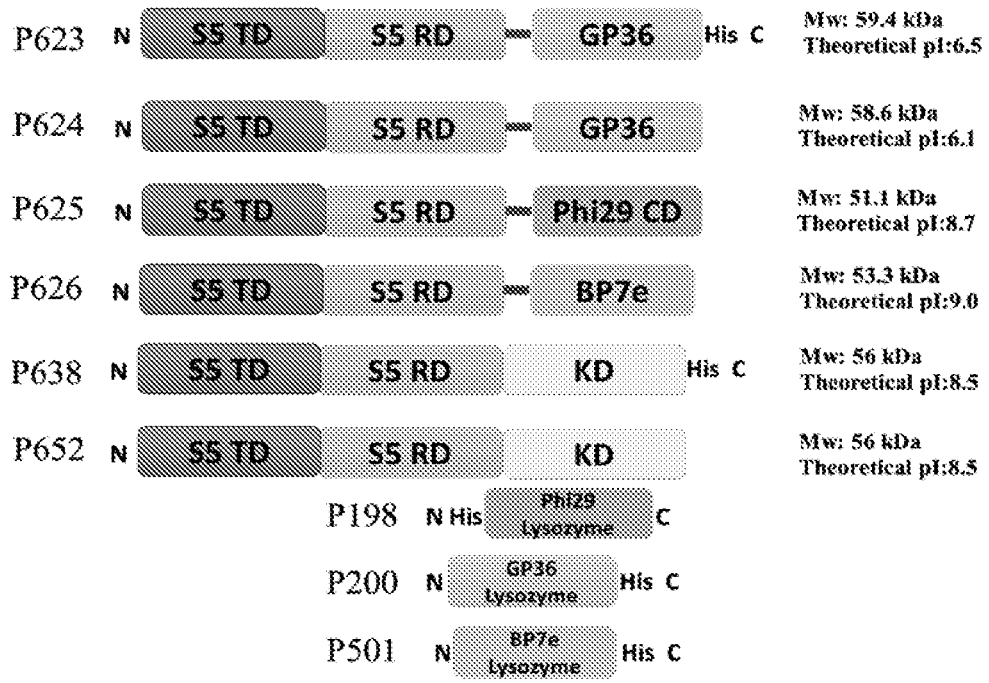
FIG. 6 shows physical map of constructs.

Physical map of constructs is presented in FIG. 6

Protein Purification:

Protein expression was done in *E. coli* ER2566 by inducing at 37° C. with 1 mM IPTG at $OD_{600}$ of 0.8 for 4 hours. Induced cell pellet was resuspended in 20 mM sodium phosphate buffer, sonicated to lyse the cells, separated supernatant and pellet by centrifugation at 10,000 rpm. Proteins P624, P625, P626, and P652 were purified from the soluble fraction using two-step ion exchange chromatography. Briefly, the clarified cell lysate was passed through an anion exchange chromatography using unosphere Q matrix (Biorad) and the flow through that contained the protein of interest was collected. The flow through was then passed through a cation exchange chromatography using unosphere S matrix (Biorad) and the bound protein was eluted with a step gradient of NaCl. The protein of interest was eluted in 300 mM NaCl for P624, P625, P626, and P652. The proteins were dialysed against 20 mM SPB, pH 7.0+150 mM NaCl for P624, P626, and P652, and with 20 mM SPB, pH 7.0 for P625.

Figure 7:
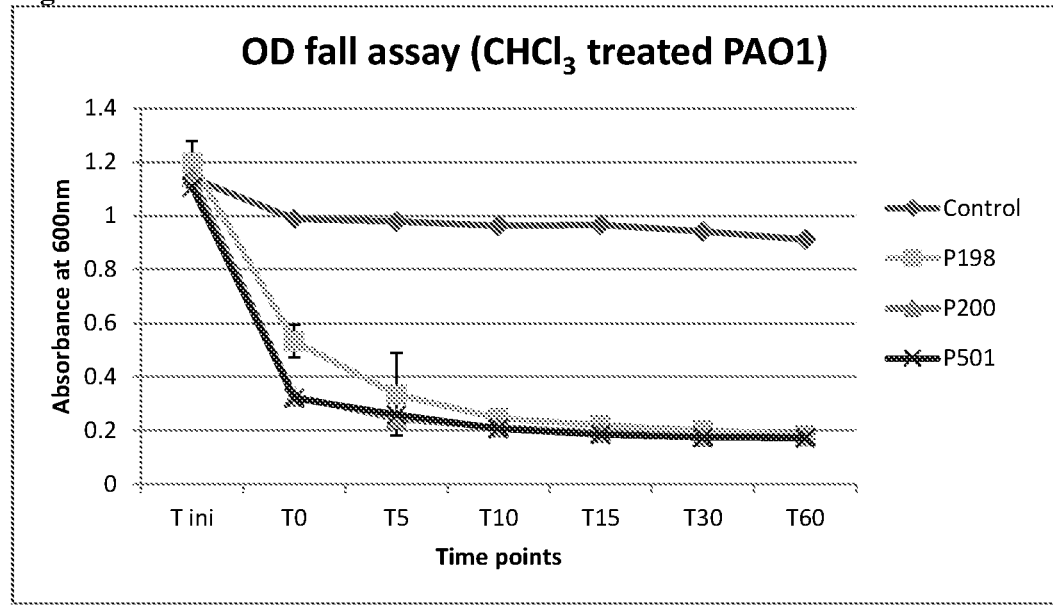
FIG. 7 shows OD fall assay using chloroform treated PAO1.

His tagged proteins P623 and P638 were purified by Ni-NTA chromatography, eluted in 300 mM Imidazole and dialysed against 20 mM SPB, pH 7.0+150 mM NaCl for P638 and 20 mM SPB, pH 7.0 for P623. All proteins were purified to ~80% homogeneity. OD fall assay:

The catalytic activity of all lysozyme domains—GP36 CD, Phi29 lysozyme, and BP7e lysozyme were determined by a turbidity reduction OD fall assay using chloroform treated *P. aeruginosa* PA01 cells as a substrate. 50 µg/ml of purified proteins were used in this assay. An active protein by OD fall assay will also suggest the correct folding of the lysozyme domain in the fusion proteins. All the three lysozyme domains were catalytically active. The results are shown in FIG. 7.

Lawn Inhibition Assay:

*P. aeruginosa* KGN 1665 lawn was prepared by growing colonies in LB broth to an $OD_{600}$ of 0.8 and a lawn was prepared on an LB agar plate. The fusion proteins were spotted at the below mentioned concentrations. P626 was spotted on CAA agar on *P. aeruginosa* PAO1, and P652 on LB agar on *P. aeruginosa* DSMZ 50071. P623: 20 µg; P624: 38 µg; P625: 32 µg; P626: 60 µg; P638: 12 µg; P652: 30 µg. Inhibition zone was observed with all the tested proteins except P625

Figure 8A:
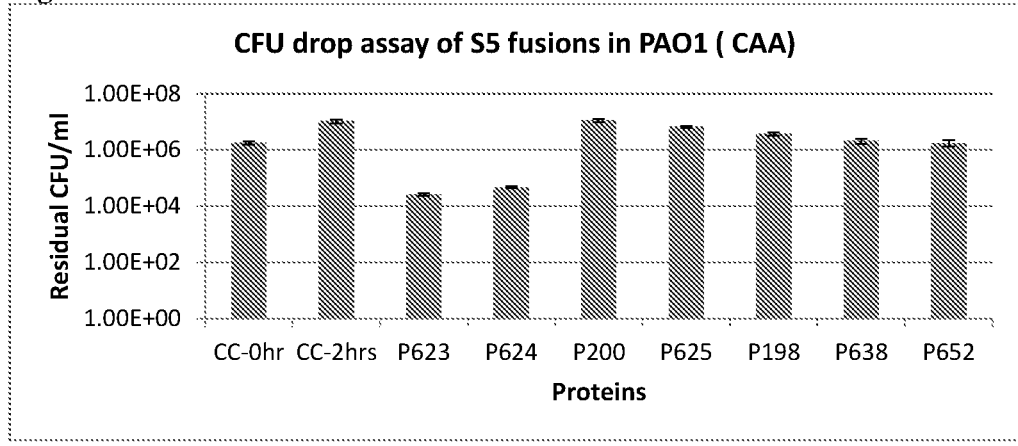
FIGS. 8A-8C show CFU drop assays of S5 fusions in PAO1 in CAA broth (FIG. 8A), P626 in PAO1 in CAA broth (FIG. 8B), and S5 fusions in PAO1 in 50% FCS.
Figure 8B:
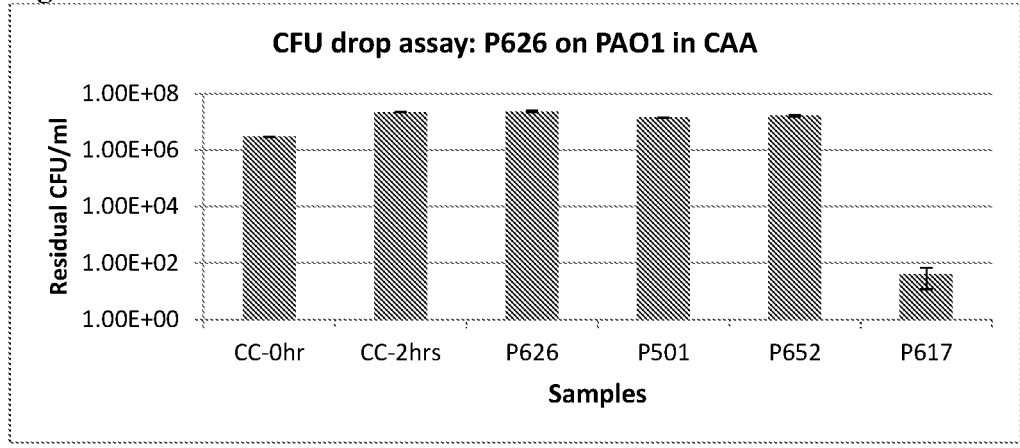
Figure 8C:
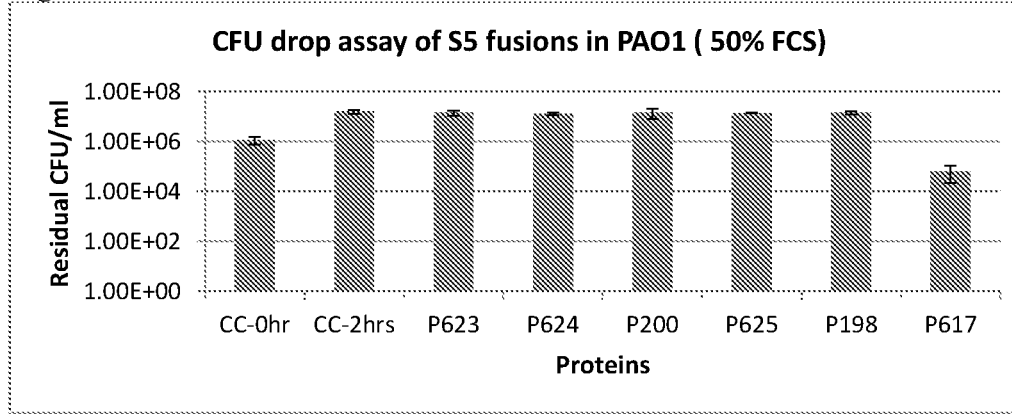

Bactericidal Activity:

The antibacterial activity of S5 pyocin and chimeric fusions P623, P624, P625, P626, P638, and P652 were tested against *P. aeruginosa* PAO1, using the CFU drop assay. Briefly, ~$10^6$ cells in CAA broth and 50% fetal calf serum (FCS) at 200 µg/ml were incubated at 37° C. for 2 hours and enumerated remaining number of viable cells by plating appropriate dilutions on LB agar plates. The experiment was set up in duplicates and the results tabulated as average of duplicates. The respective lysozymes (P200, P198, and P501) were used as negative controls. The results are shown in FIG. 8A-8C. P623 and P624 (S5 pyocin-GP36 fusion) were showing bactericidal activity on PA01 in CAA None of the proteins were bactericidal on PA01 in 50% FCS.

Example V Using Klebicin and Pyocin to Target Mixed Infections (*K. Pneumoniae* and *P. Aeruginosa*)

Introduction

*Klebsiella pneumoniae* and *Pseudomonas aeruginosa* are two biofilm-forming organisms that can coexist during infections of the urinary tract, respiratory tract, and burn wounds and associated with foreign bodies (Childers et al. (2013)).

Bacteriocins are proteinaceous molecules naturally produced by bacteria to kill closely related bacteria. Several bacteriocins are known, e.g., Klebicins, pyocins, colicins, pesticins, etc.

Klebicins have been used for the purpose of typing *Klebsiella* spp for many decades, but have not been characterized in terms of their antibacterial properties in vitro or in vivo.

Pyocins are bacteriocins produced by more than 70% of *Pseudomonas* spp. The high molecular weight pyocins are the R-type and F-type pyocins and the small molecular weight pyocins are the S-type pyocins. The specificity for the entry of S-type pyocins is determined by a receptor present on the cell surface.

Cloning of Klebicin CCL and S5 Pyocin

Klebcin CCL gene was PCR amplified from the genome of *K. pneumoniae*, with its immunity gene, and cloned into pET26b plasmid, expressed in *E. coli* ER2566, and purified by conventional chromatography (anion and cation exchange chromatography). The construct was sequence confirmed and labeled (designated) pGDC 628.

S5 type pyocin was PCR amplified from the genome of *P. aeruginosa* and cloned into pET26b plasmid, expressed in *E. coli* ER2566, and purified by conventional chromatography (anion and cation exchange chromatography). The construct was sequence confirmed and designated pGDC 652.

Lawn Inhibition Assay:

A lawn of *K. pneumoniae* B2094 and *P. aeruginosa* KGN 1665 was prepared on an LB agar plate. Both proteins at 25 µg concentration were spotted on a CAA agar plate. The combination of P628 and P652 showed lawn inhibition in mixed cultures.

Bactericidal Activity of P628 and P652 on *P. aeruginosa* KGN 1665 and *K. pneumoniae* B2094

Figure 9A:
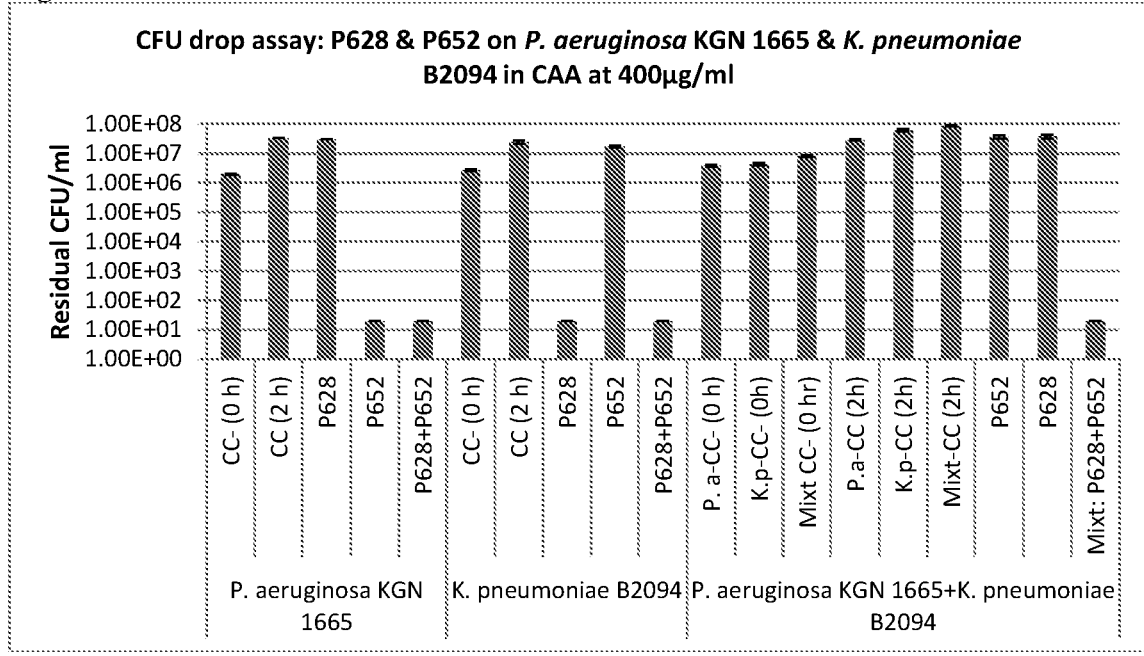
FIGS. 9A-9B show CFU drop assays of combination of P628 and P652 on *P. aeruginosa* KGN 1665 and *K. pneumoniae* B2094 in CAA at 400 ug/ml (FIG. 9A), and combination of P628 and P652 on *P. aeruginosa* KGN 1665 and *K. pneumoniae* B2094 in CAA at 200 ug/ml (FIG. 9B).
Figure 9B:
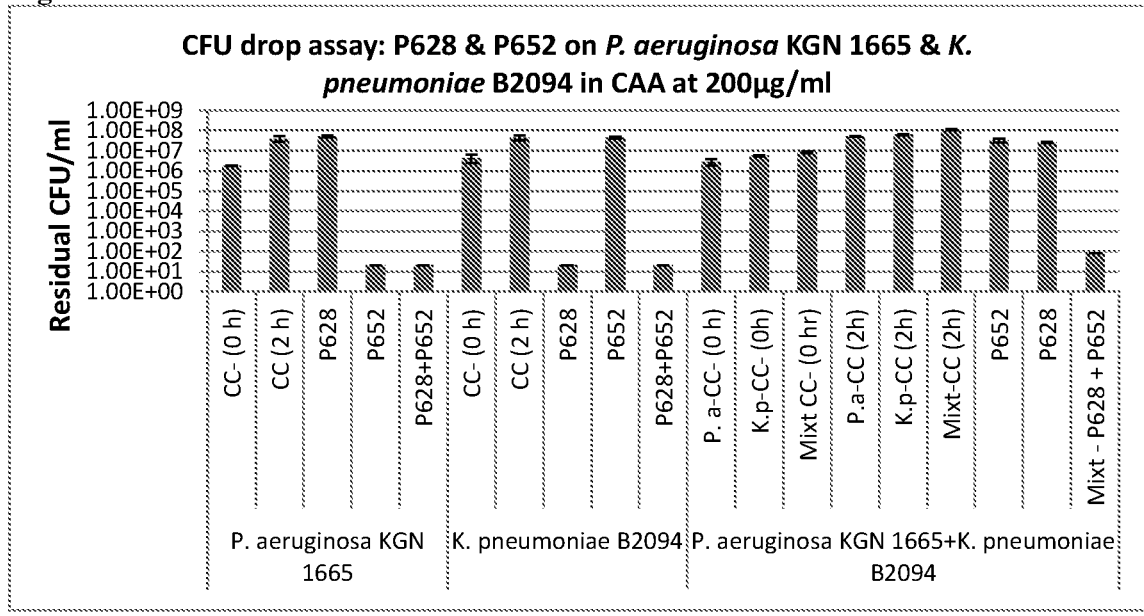
Figure 10A:
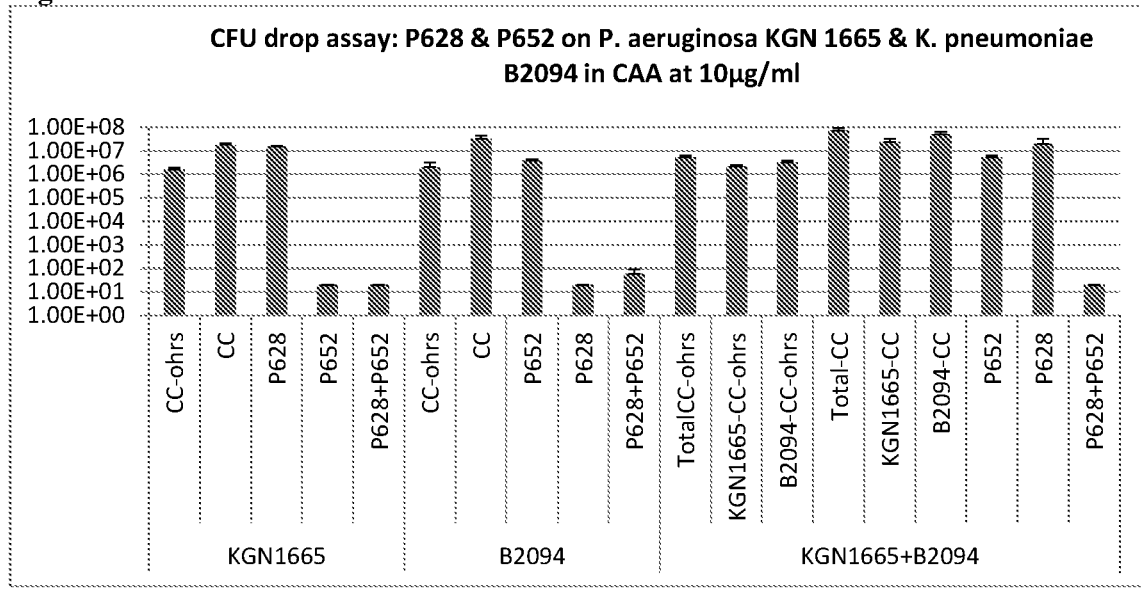
FIGS. 10A-10B show CFU drop assays of combination of P628 and P652 on *P. aeruginosa* KGN 1665 and *K. pneumoniae* B2094 in CAA at 10 ug/ml (FIG. 10A), and combination of P628 and P652 on *P. aeruginosa* KGN 1665 and *E. coli* B563 in CAA at 10 ug/ml (FIG. 10B).

The antibacterial activity of P628 and P652 were tested using the CFU drop assay. ~$10^6$ cells of *P. aeruginosa* KGN 1665(~$1 \times 10^6$) and *K. pneumoniae* B2094 (~$1 \times 10^6$) were mixed in CAA broth at 200 µg/mL and 400 µg/mL, was incubated at 37° C. for 2 hours and remaining number of viable cells were enumerated. The experiment was set up in duplicates and the results tabulated as average of duplicates. The results are shown in FIGS. 9A and 9B. The combination of P628 and P652 exhibit bactericidal activity in mixed cultures at 400 µg/ml and 200 µg/ml A dose-dependent study with mixed cultures was done to determine the minimum amount of P628 and P652 required to kill the cells by at least 3 orders of magnitude. The results are shown in FIG. 10A. Combination of P628 and P652 exhibit bactericidal activity in mixed cultures even at 10 µg/ml in both CAA and FCS.

Bactericidal Activity of P628 and P652 on *P. aeruginosa* KGN 1665 and *E. coli* B563

Figure 10B:
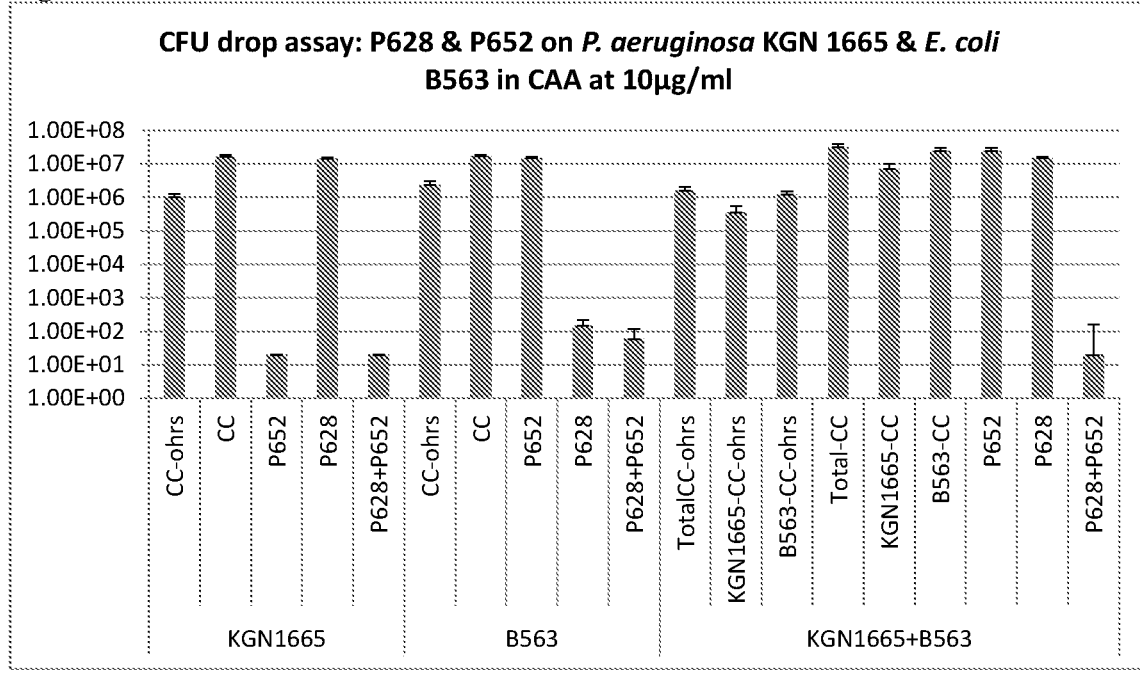

The antibacterial activity of P628 and P652 was tested using the CFU drop assay. ~$10^6$ cells of *P. aeruginosa* KGN 1665 (~$1 \times 10^6$) and *E. coli* B563 (~$1 \times 10^6$) were mixed in CAA broth and proteins added individually and in combination at 10 µg/ml, was incubated at 37° C. for 2 hours and remaining number of viable cells were enumerated. The experiment was setup in duplicates and the results tabulated as average of duplicates. The results are shown in FIG. 10B. The Combination of P628 and P652 exhibit bactericidal activity in mixed cultures at 10 µg/ml.

Example VI FYU a Binding Domain—Lysozyme Domain Fusions

Introduction

Bacteria utilize Iron through receptors on the cell surface for the uptake of iron. The uptake is mediated by molecules called siderophores wherein the siderophore binds to free iron and enters through the receptors following which the iron is released from the siderophore and utilized.

Pesticins are bacteriocins produced by *Yersinia pestis* and the receptor for pesticin uptake is the iron uptake receptor FyuA present in *Yersinia pseudotuberculosis* and certain pathogenic strains of *E. coli*. Pesticin contains a Fyu A binding domain (FyuA BD) and a peptidoglycan degrading domain (PGD). Lukacik et al. (2012) "Structural engineering of a phage lysin that targets Gram-negative pathogens" Proc Natl Acad Sci USA, 109:9857-62. The authors demonstrated that replacing the PGD domain with a heterologous lysozyme domain from the T4 lysozyme that is structurally similar to its native lysozyme domain was able to enter and kill bacterial cells.

Generating Fyu a Binding Domain—T4 Lysozyme and Fyu a Binding Domain—*P. aeruginosa* Phage P134 Virion Associated Lysozyme GP36 (Cloning Strategy)

Fyu A binding domain was fused with T4 lysozyme as NdeI-XhoI site in pET26b as synthetic construct. Fyu A binding domain was fused to the *P. aeruginosa* phage P134 virion associated lysozyme GP36 in the *E. coli* expression vector pET26b into the cloning sites NdeI-XhoI. The clones were sequence confirmed and designated as pGDC 558 (Fyu A BD—T4 lysozyme fusion) and pGDC 567 (Fyu A BD—GP36 fusion)

Protein Expression Studies:

Test protein expression was performed in *E. coli* ER2566 by inducing with 1 mM IPTG at 37° C. for 4 hours induced at $OD_{600}$ of 0.8. Induced cells were pelleted, resuspended in 20 mM Sodium phosphate buffer and sonicated to lyse the cells. The lysate was then pelleted by centrifugation at 10,000 rpm for 15 minutes and the supernatants and pellets were collected separately and analyzed on an SDS-PAGE gel. Protein expression was observed at ~37 kDa for P558 and 42 kDa for P567 on acrylamide gel in soluble fraction of the cells.

Purification of Proteins:

Protein expression was done in *E. coli* ER2566 by inducing with 1 mM IPTG at 37° C. at 0.8 $OD_{600}$ for 4 hours. Induced cell pellet was resuspended in 20 mM sodium phosphate buffer, sonicated to lyse the cells, separated supernatant and pellet by centrifugation at 10,000 rpm. Protein was purified from the soluble fraction using two-step ion exchange chromatography. Briefly, the clarified cell lysate was passed through an anion exchange chromatography using unosphere Q matrix (Biorad) and the flow through that contained the protein of interest was collected. The flow through was then passed through a cation exchange chromatography using unosphere S matrix (Biorad) and the bound protein was eluted with a step gradient of NaCl. The protein of interest was eluted in 500 mM NaCl. The proteins were dialysed against 20 mM SPB, pH 7.0+300 mM NaCl.

OD Fall Assay

Figure 11:
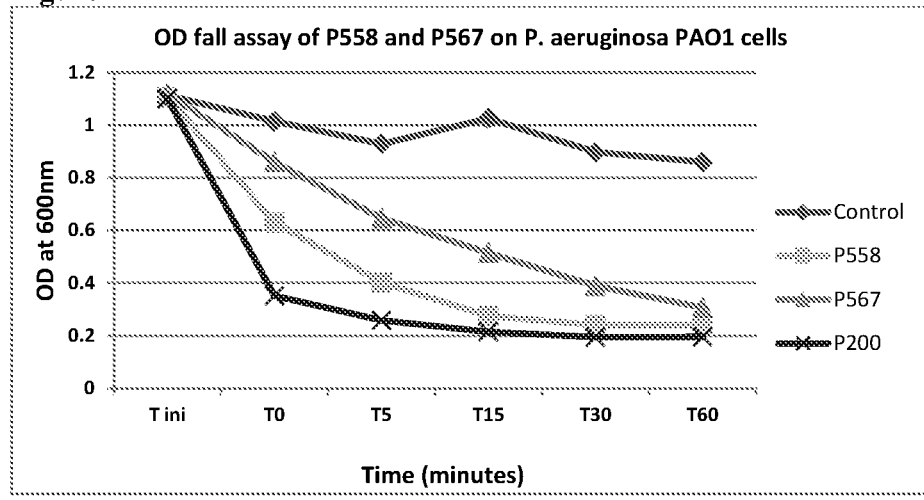
FIG. 11 shows OD fall assay of P558 and P567 on *P. aeruginosa* PAO1 cells.

The catalytic activity of T4 lysozyme and GP36 lysozyme in the fusion proteins were determined by a turbidity reduction OD fall assay using chloroform treated *P. aeruginosa* PA01 cells as substrate. 50 µg/ml of purified proteins were used in this assay. An active protein by OD fall assay will also suggest the correct refolding of the lysozyme domain in the fusion proteins. The results are shown in FIG. 11. The purified proteins P558 and P567 were catalytically active.

Cloning and Expression of FyuA Receptor in *E. coli* ER2566

The FyuA BD fusions utilize FyuA receptor for entry into bacteria. Lab strains of *E. coli* do not harbor this receptor and hence are not sensitive to these proteins. However, if the receptor could be expressed heterologously from a plasmid in lab *E. coli*, the strain may become sensitive to the fusion proteins. To this end, the FyuA receptor was isolated from an *E. coli* clinical isolate and cloned into pET26b as NcoI-XhoI for expression as a PelB signal sequence fusion tag for periplasmic localization of the receptor.

Protein Expression Studies

Test protein expression was performed in *E. coli* ER2566 by inducing with 1 mM IPTG at 37° C. for 4 hours induced at $OD_{600}$ of 0.8. Protein of expected size was observed in the induced cells. The clones were sequence confirmed and designated as pGDC 571.

Testing of P558 and P567 on FyuA Expressing ER2566/pGDC571 pGDC571 and pET26b were transformed into *E. coli* ER2566 and the resulting colonies were grown to an $OD_{600}$ of 0.8 and a lawn prepared on an LB plate. 50 µg of P558 and P567 were spotted on ER2566/pGDC 571+ and ER2566 pET26b (control). Lawn inhibition observed with P558 and P567 indicating that these proteins were active on a FyuA expressing *E. coli* strain.

Effect of P558 and P567 on FyuA Expressing *E. coli*

Figure 12:
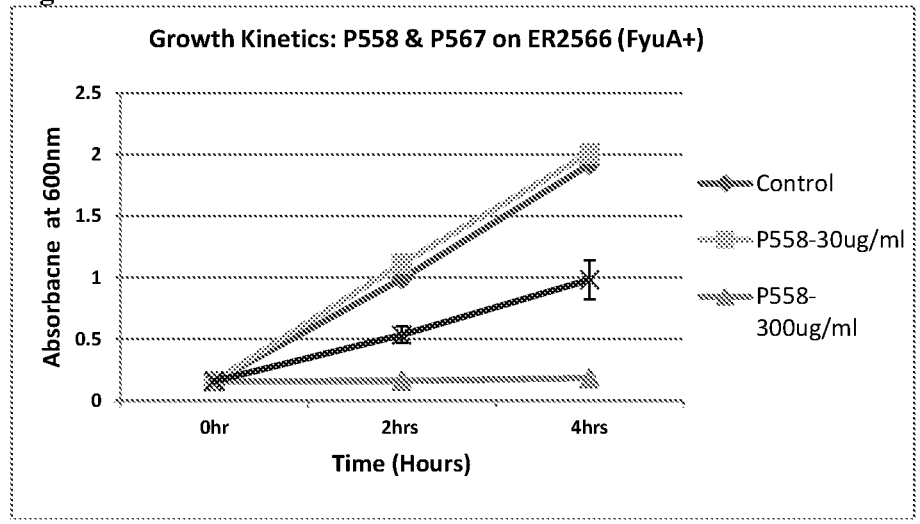
FIG. 12 shows effect of P558 and P567 on growth kinetics of *E. coli* ER2566 (FyuA+).

The antibacterial activities of P558 and P567 were tested against FyuA expressing *E. coli* using the CFU drop assay. ~$10^7$ cells of ER2566/pGDC 571 in LB broth were treated with 30 µg/ml and 300 µg/ml of P558 and with 300 µg/ml of P567, incubated at 37° C. for 2 and for 4 hours and enumerated remaining number of viable cells. The experiment was set up in duplicates and the results tabulated as average of duplicates. The results are shown in FIG. 12. A static effect observed with P558 at 300 µg/ml until 4 hours.

Figure 13:
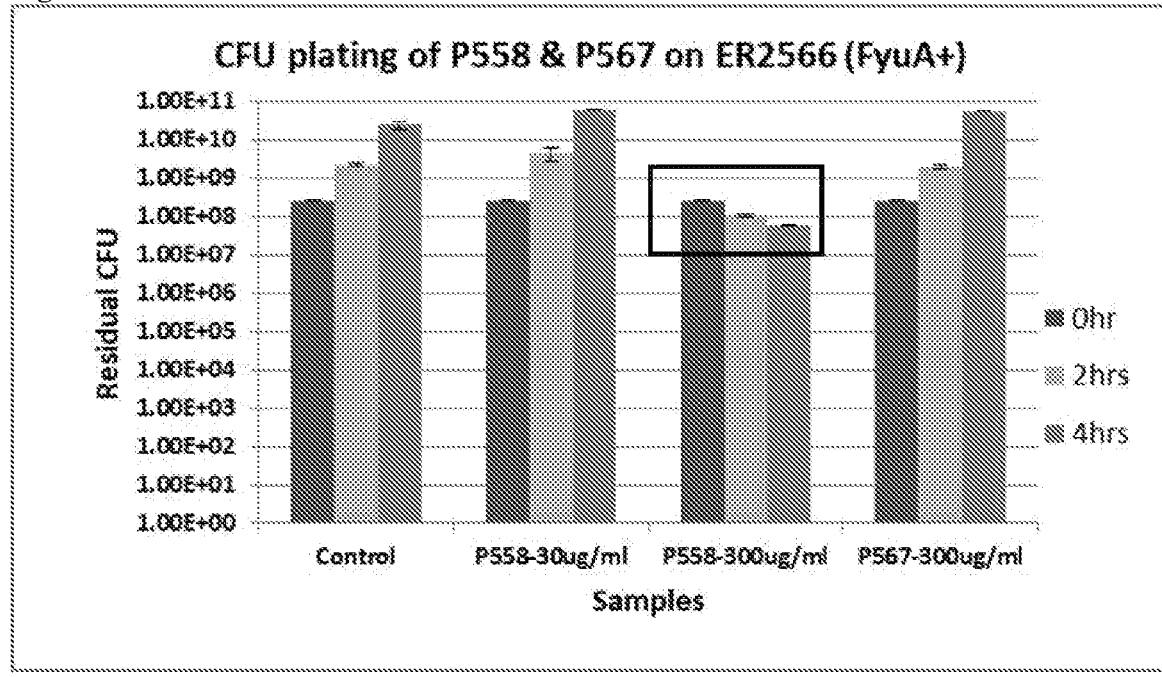
FIG. 13 shows CFU plating of P558 and P567 on *E. coli* ER2566 (FyuA+).

Viability of the cells at respective time points were determined by plating appropriate dilutions on LB plates and incubated these plates at 37° C., for 16-18 hrs. The results are shown in FIG. 13. A bacteriostatic effect was observed with P558 (300 µg/ml, with the cell numbers remaining constant even after 4 hours.

Figure 14:
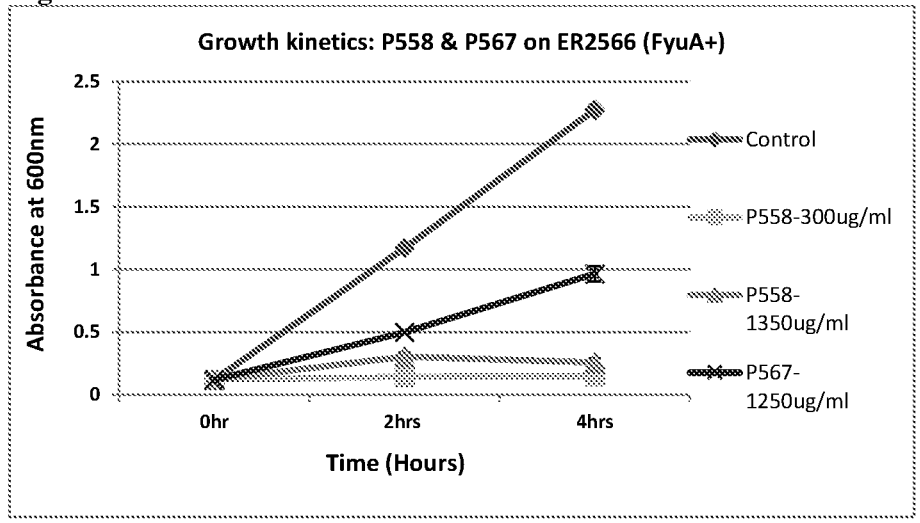
FIG. 14 shows effect of P558 and P567 on growth kinetics of *E. coli* ER2566 (FyuA+).

The effect of P558 and P567 on FyuA expressing *E. coli* as described above was carried out at protein concentrations of 300 µg/ml and 1350 µg/ml for P558 and 1250 µg/ml for P567. As a control, the ER2566 with the vector control (ER2566/pET26b) also was treated with P558 and P567 at the same concentrations. The results are shown in FIG. 14. P558 inhibited growth of ER2566 cells expressing FyuA receptor and no growth inhibition observed with control (ER2566/pET26b).

Activity of P558 on *E. coli* ER2566/FyuA+

Figure 15A:
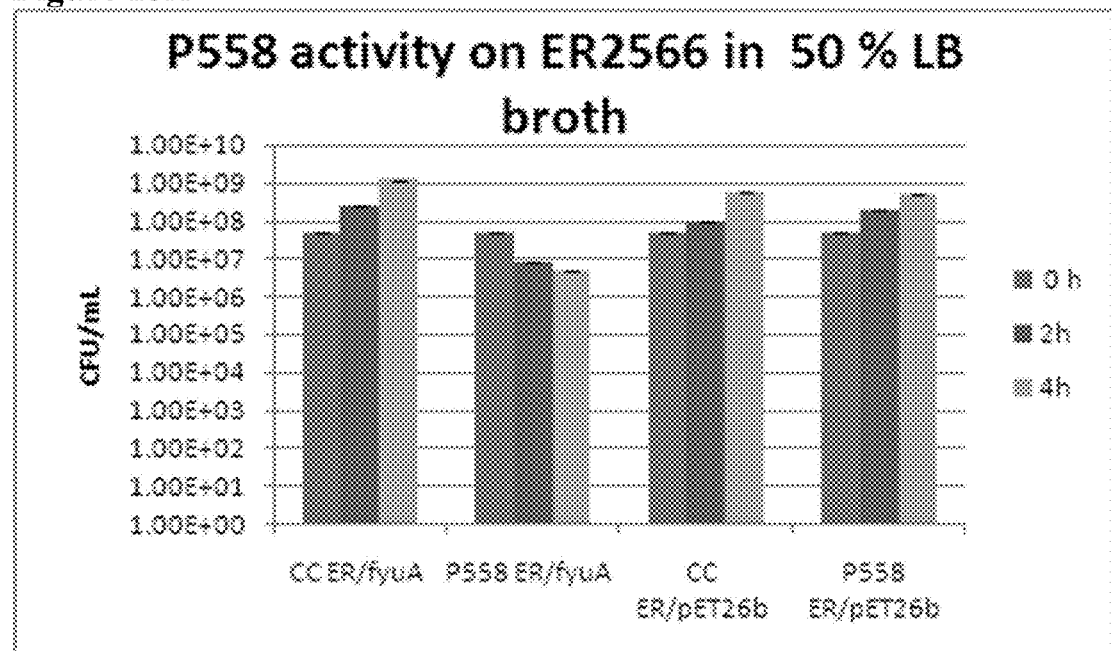
FIGS. 15A-15B show P558 activity on *E. coli* ER2566 in 50% LB broth (FIG. 15A) and P558 activity on *E. coli* ER2566 in 50% FCS (FIG. 15B).
Figure 15B:
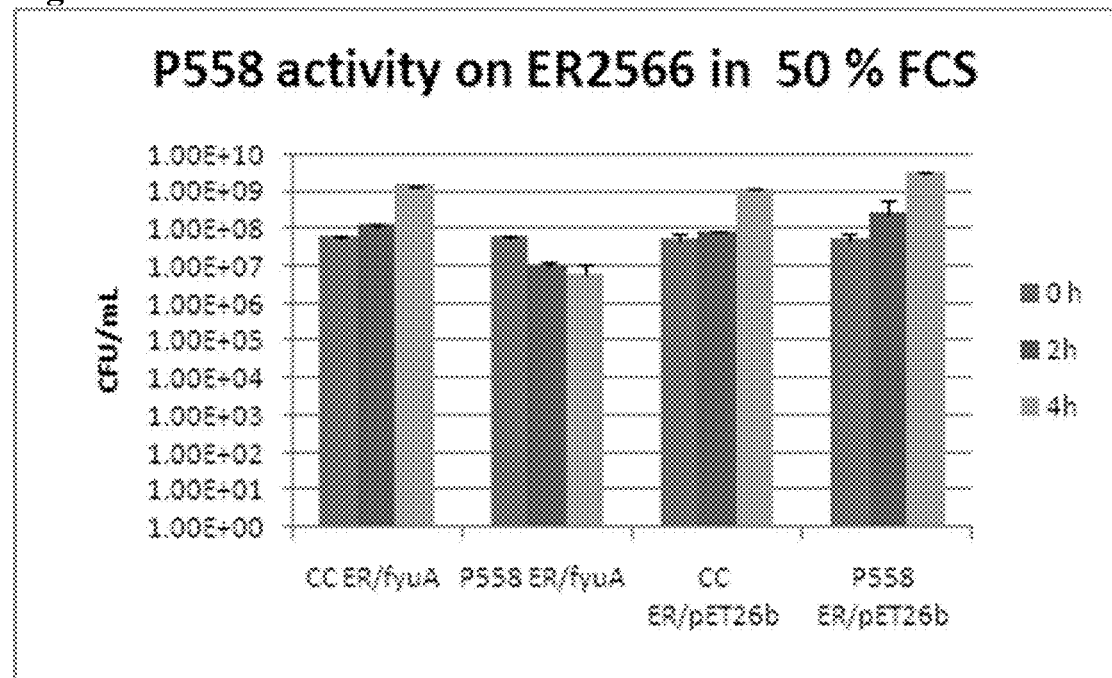

The antibacterial activity of P558 was tested against FyuA expressing *E. coli* using the CFU drop assay. Briefly, ~$10^7$ cells of ER2566/FyuA in 50% LB broth and 50% fetal calf serum (FCS) were treated with P558 at 300 µg/ml, incubated at 37° C. for 2 and 4 hours and the cell killing was determined by enumerating the remaining number of viable cells. The experiment was set up in duplicates and the results tabulated as average of duplicates. The results are shown in FIGS. 15A and 15B.

Figure 16:
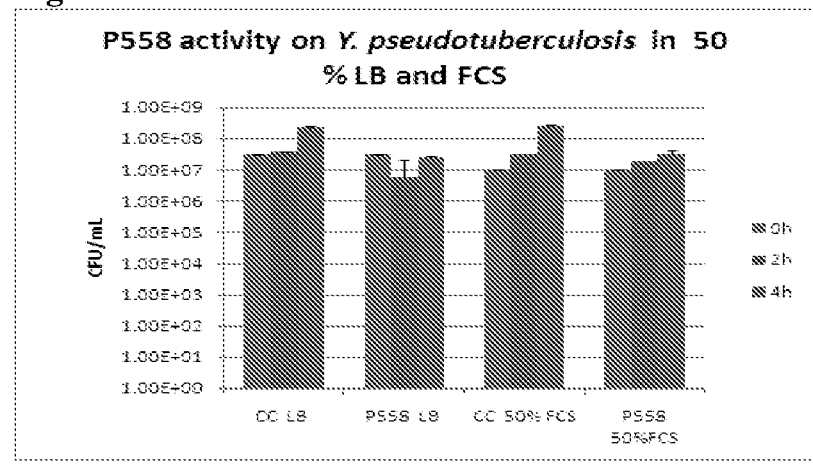
FIG. 16 shows P558 activity on *Y. pseudotuberculosis* in 50% LB and FCS.

Activity of P558 on *Yersinia pseudotuberculosis*:

The antibacterial activity of P558 was tested against *Yersinia pseudotuberculosis* using the CFU drop assay. Briefly, ~$10^7$ cells of *Y. pseudotuberculosis* in 50% LB broth and 50% fetal calf serum (FCS) were treated with P558 at 300 μg/ml, incubated at 37° C. for 2 and 4 hours and the cell killing was determined by enumerating the remaining number of viable cells. The experiment was set up in duplicates and the results tabulated as average of duplicates. The results are shown in FIG. 16. P558 showed static effect on *Y. pseudotuberculosis* in both 50% LB medium and 50 FCS.

Activity of P558 on *E. coli* SLC-6

Figure 17:
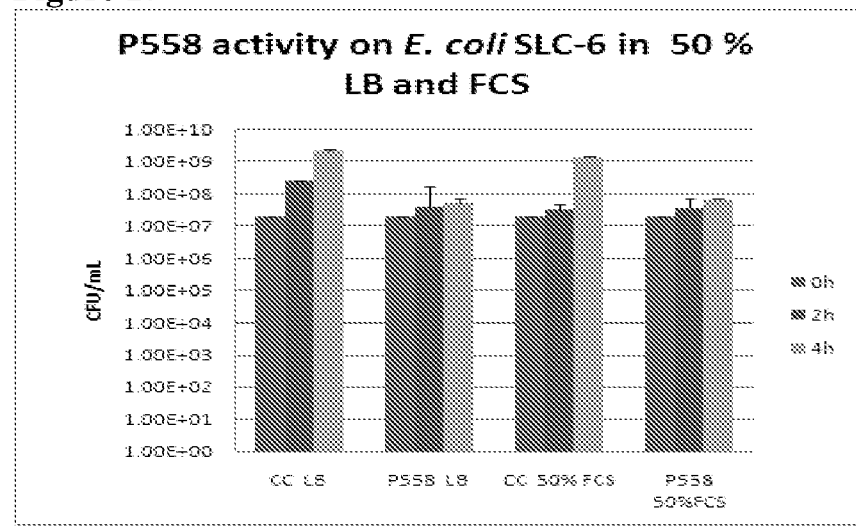
FIG. 17 shows P558 activity on *E. coli* SLC-6 in 50% LB and FCS.

The antibacterial activity of P558 was tested against *E. coli* SLC-6, a urinary tract infection isolate using the CFU drop assay. UTI isolates are known to harbor FyuA gene and express the receptor in the urinary tract that would aid the bacteria to colonize and survive. Briefly, ~$10^7$ cells in 50% LB broth and 50% fetal calf serum (FCS) at 300 μg/ml, incubated at 37° C. for 2 and 4 hours and enumerated remaining number of viable cells. The experiment was setup in duplicates and the results tabulated as average of duplicates. The results are shown in FIG. 17. P558 showed static effect on *E. coli* SLC-6 in both 50% LB medium and 50% FCS.

Activity of P558 on *E. coli* UTI Isolates Positive for fyuA Gene PCR

Figure 18A:
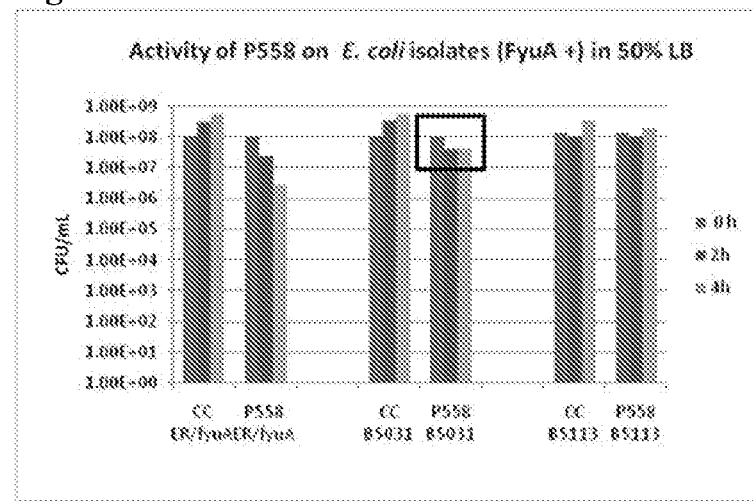
FIGS. 18A-18B show activity of P558 on *E. coli* isolates (FyuA+) in 50% LB (FIG. 18A); and activity of P558 on *E. coli* isolates (FyuA+) in 50% FCS (FIG. 18B).
Figure 18B:
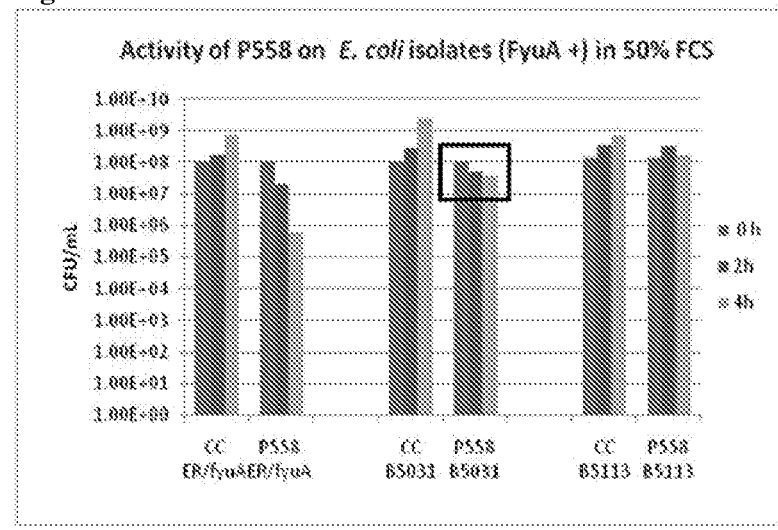

Clinical *E. coli* strains isolated from urine was screened for the presence of fyuA gene by PCR. Few of the positive ones were taken as test strains for determining the activity of P558. Assay Conditions: 50% LB broth and 50% Fetal calf serum (FCS), Reaction volume: 2 ml. Duration: 2 and 4 hours at 37° C., 200 rpm. Strains tested: *E. coli* ER2566/FyuA, B5031, B5113 (*E. coli* UTI isolate). The results are shown in FIGS. 18A and 18B. P558 showed static effect on *E. coli* B5031 in 50% LB and 50% FCS Activity of P558 on *Klebsiella* Clinical Isolates Positive for fyuA Gene PCR: (FyuA+)

Figure 19:
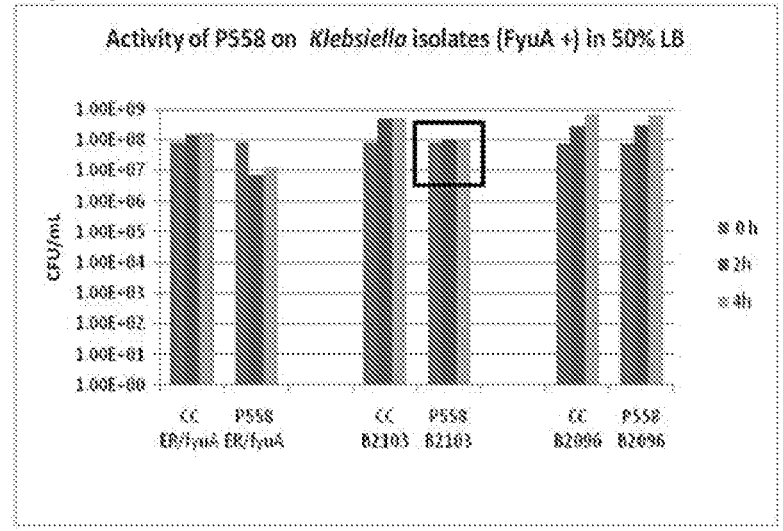
FIG. 19 shows activity of P558 on Klebsiella isolates (FyuA+) in 50% LB.

Clinical *Klebsiella* strains isolated from urine were screened for the presence of fyuA gene by PCR. Few of the positive ones were taken as test strains for determining the activity of P558. Assay Conditions: 50% LB broth and 50% Fetal calf serum (FCS), Reaction volume: 2 ml. Duration: 2 and 4 hours at 37° C., 200 rpm. Strains tested: *E. coli* ER2566/FyuA, *Klebsiella* spp B2103, Klebsiellaspp B2096 (*Klebsiella* PCR positive for FyuA+). The results are shown in FIG. 19. P558 showed static effect on *E. coli* B2103 in 50% LB.

MIC of P558 in LB (50%) and FCS (50%)

MIC assay was done with P558 in 50% LB and 50% FCS by the CLSI method on *E. coli* ER2566/FyuA, *E. coli* ER2566/pET26b, *Y. pseudotuberculosis* and *E. coli* SLC-6. MIC was observed at both 6 hours and 18 hours. The results are shown in Tables 8 and 9. P558 showed very low MIC on *E. coli* ER2566 (FyuA) only at 6 h, however no MIC observed on other strains tested.

TABLE 8

| | | P558 MIC in μg/mL at 6 h | |
|---|---|---|---|
| Sl. No | Isolates | 50% MHB | 50% FCS |
| 1 | *E. coli* ER2566/FyuA | 0.09 | 0.09 |
| 2 | *E. coli* ER2566/pET26b | >925 | >925 |

TABLE 8-continued

| | | P558 MIC in μg/mL at 6 h | |
|---|---|---|---|
| Sl. No | Isolates | 50% MHB | 50% FCS |
| 3 | *Y. pseudotuberculosis* | >925 | >925 |
| 4 | *E. coli* SLC-6 | >925 | >925 |

TABLE 9

| | | P558 MIC in μg/mL at 18 h | |
|---|---|---|---|
| Sl. No | Isolates | 50% MHB | 50% FCS |
| 1 | *E. coli* ER2566/FyuA | >950 | >950 |
| 2 | *E. coli* ER2566/pET26b | >950 | >950 |
| 3 | *Y. pseudotuberculosis* | >950 | >950 |
| 4 | *E. coli* SLC-6 | >950 | >950 |

Other FyuABD Fusions:

Fusions of FyuA binding domain and peptidoglycan degrading domains were generated by cloning into pET26b plasmid and sequence confirmed.
 a. FyuA BD—Phi29 lysozyme from *B. subtilis* phage Phi29
 b. FyuA BD—BP7e lysozyme from *E. coli* phage BP7
 c. FyuA BD—Phi6 P5 lytic enzyme from *P. syringiae* phage Phi6
 d. FyuA BD—GS linker—GP36 CD The proteins were purified by ion exchange chromatography to 90% homogeneity.

Figure 20:
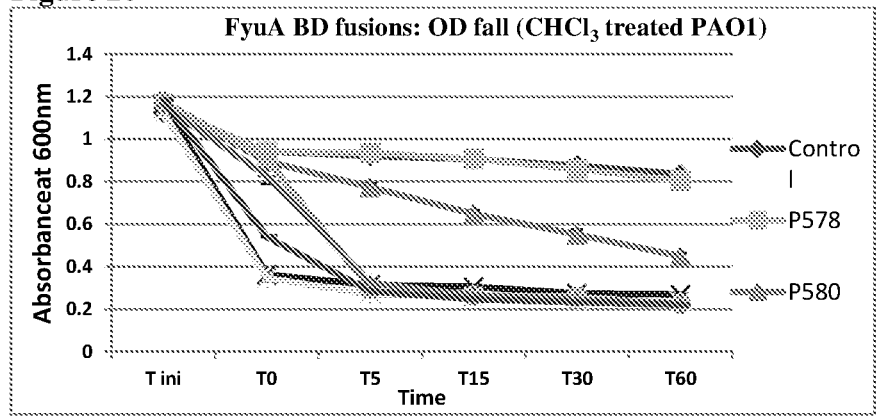
FIG. 20 shows catalytic activity of FyuA BD fusions as determined by OD fall assay using chloroform treated *P. aeruginosa* PAO1.

OD Fall Assay:

The catalytic activity of the FyuA fusions were determined by OD fall assay using chloroform treated *P. aeruginosa* cells as substrate. 50 μg/ml of purified proteins were used in this assay. An active protein by OD fall assay will also suggest the correct refolding of the lysozymes. The results are shown in FIG. 20. The purified proteins P581, P583, and P580 were catalytically active as observed by the OD fall obtained. P578 was not active indicating that the catalytic domain was non functional.

Figure 21:
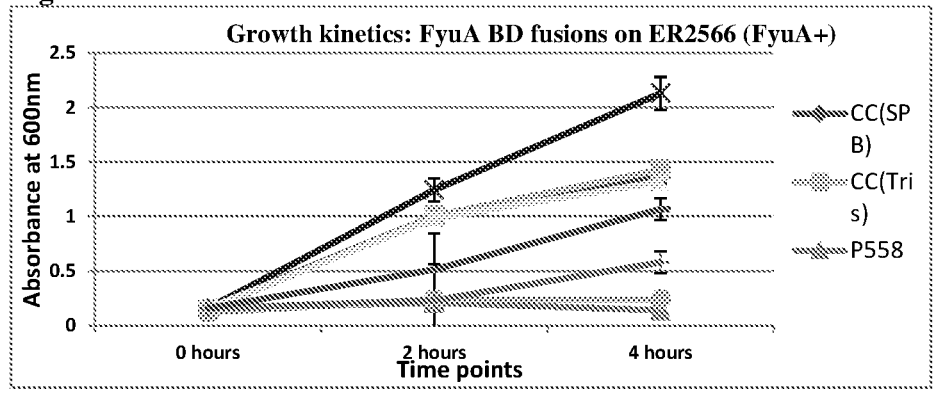
FIG. 21 shows effect of of FyuA BD fusions on growth kinetics of *E. coli* ER2566 (FyuA+).

Effect of FyuA BD Fusions on FyuA Expressing *E. coli*:

The antibacterial activity of the fusion proteins were tested against FyuA expressing *E. coli* using the CFU drop assay. Briefly, ~$10^7$ cells of ER2566/FyuA in 50% LB broth were treated with P558 at 300 μg/ml, incubated at 37° C. for 2 and 4 hours and the cell killing was determined by enumerating the remaining number of viable cells. The experiment was set up in duplicates and the results tabulated as average of duplicates. The results are shown in FIGS. 21. P558 and P581 inhibited growth of ER2566 cells expressing FyuA receptor. No inhibition was observed with other proteins.

Figure 22:
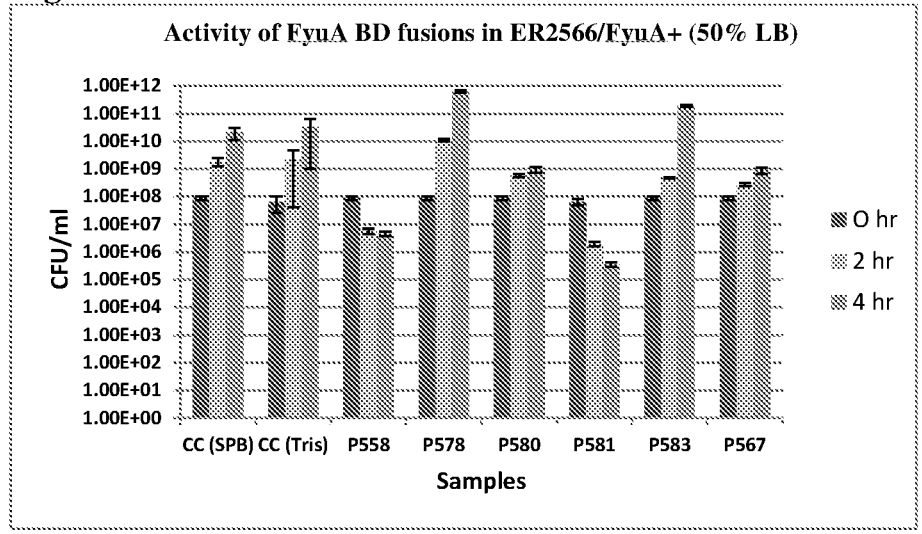
FIG. 22 shows activity of FyuA BD fusions on *E. coli* ER2566 (FyuA+) in 50% LB.

Viability of the cells at respective time points were determined by plating appropriate dilutions on LB plates and incubated these plates at 37° C., for 16-18 hrs. The results are shown in FIG. 22. P558 showed ~1 log drop and P581 ~2 logs drop in 50% LB medium Lawn Inhibition Assay:

The fyuA construct pGDC571 was transformed into *E. coli* ER2566 and the resulting colonies were grown in LB broth to an $OD_{600}$ of 0.8 and a lawn was prepared on an LB agar plate. The fusion proteins were spotted on ER2566/pGDC 571 and *Y. pseudotuberculosis*. Clear inhibition zone observed with P581 on FyuA expressing ER2566 and *Y. pseudotuberculosis*.

Activity of P581 on Clinical UTI Strains (FyuA+) in LB and FCS

Figure 23:
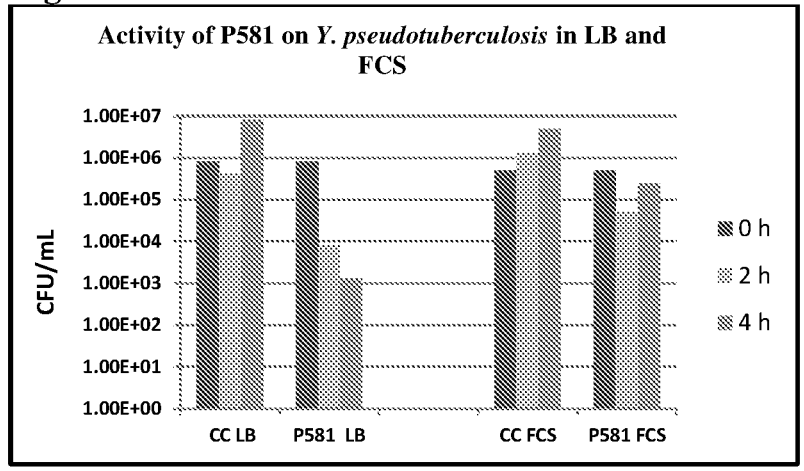
FIG. 23 shows activity of P581 on *Y. pseudotuberculosis* in LB and FCS.

*Yersinia pseudotuberculosis*, *E. coli* B5501, B5503, and B5504. Assay Conditions: 50% LB broth and 50% Fetal calf serum (FCS). Reaction volume: 2 ml. Duration: 2 and 4 hours at 37° C., 200 rpm. Cells: $10^5$ CFU/mL. Protein: 300 µg/mL. Incubation: 37° C., 200 rpm, 2 h, 4 h. The results are shown in FIG. 23. P581 was active on *Y. pseudotuberculosis* in both LB and FCS.

Exampe VII Transfer of a Selected Bacteriocin Receptor to a TargeT *Escherichia* Bacteria The gene encoding the FyuA receptor is PCR amplified from *Yersinia pseudotuberculosis* genome (Accession: Z35107.1) using primers containing *E. coli* signal sequence (e.g., pelB). A broad host range conjugative plasmid (e.g., pLM2) is isolated from *Salmonella typhimurium* LT2 and the above PCR product is cloned at a suitable restriction site, transformed by electroporation into *E. coli* lab strain and screened by PCR for recombinant clones. The colony containing the gene of interest is the "donor" bacteria. 5 ml of donor and recipient cells (*E. coli* in which the FyuA receptor has to be expressed) are grown to $OD_{600}$ of 0.5-0.7. 100 microliters of donor and recipient cultures are mixed (Controls: 100 microliters of donor and recipient cells alone), centrifuged to wash cells with 0.85% saline twice. The pellet is resuspended in 20 microliters of saline, and spotted on a well-dried LB agar petri plate. The plate is allowed to dry and incubated overnight at degrees centigrade following which the culture is scraped into 500 microliters saline and vortexed to disrupt mating pairs. The suspension is plated at various appropriate dilutions on respective selection plates, e.g., dual antibiotic plates. Appropriate colonies are typically confirmed for conjugation by PCR for the presence of conjugative plasmid. The transconjugant colony is grown in LB broth to an $OD_{600}$ of 0.8. The culture is diluted to $OD_{600}$ of 0.2 and spread plated on LB agar plate and allowed to dry. Protein P558 (FyuA binding domain— T4 lysozyme) fusion is spotted (10 μg) on the lawn and plate incubated at 37° C. for 17 hours. A zone of inhibition seen as clearance indicates the susceptibility of the bacteria due to the expression of the FyuA receptor. A control culture of the recipient bacteria is also spotted with P558.

Example VIII Construction of Bacteriocins Fused with Amps

The genes encoding bacteriocins are cloned into *E. coli* expression vectors such as pET plasmids and the expression of the recombinant bacteriocins are confirmed. DNA sequences encoding the AMPS are cloned either at the 5' or 3' end of the bacteriocins by PCR based methods to obtain a fusion gene. Different AMP sequences as listed in the table above are fused to various bacteriocins. These fusion genes are cloned into bacterial expression vectors and DNA sequence are confirmed. Alternatively, the DNA sequence encoding the AMPS is synthesized as oligos with appropriate restriction enzyme recognition sites to clone into plasmids that already harbor bacteriocin genes.

Protein Expression, Purification and Refolding:

All DNA sequence confirmed chimeric bacteriocins are expressed in appropriate laboratory *E. coli*. For example, *E. coli* ER2566 carrying the plasmids are grown, e.g., at 37° C. till $OD_{600}$ reached ~0.8 to 1.0 and the protein expression is induced by addition of IPTG to a final concentration of 1 mM and the induction is done, e.g., at 37° C. for 4 hours. After 4 hours of IPTG induction, the cells are harvested and protein expression checked on an acrylamide gel. Once the expression of the test recombinant chimeric bacteriocin is confirmed, it is purified, e.g., by affinity chromatography. Proteins that are expressed in the soluble fraction of the cells are purified, e.g., using native purification conditions and proteins expressed as inclusion bodies (IBs) are purified under denaturing conditions, using either urea or guanidine hydrochloride to denature the IBs. Refolding of the denatured proteins is done, e.g., by removal of the denaturant, e.g., by dialyzing against appropriate buffer at 4° C. for 16-18 hrs. After refolding the homogeneity of the purified, refolded proteins is analyzed on an acrylamide gel and the protein concentration determined by Bradford's assay.

Bactericidal Assays:

a) CFU drop assay in buffer and buffered saline:

Gram-negative cells grown, e.g., in LB medium, until mid-log phase ($OD_{600}$ of 0.6) are diluted 100-fold in appropriate buffer such as 20 mM HEPES pH 7.0 or 20 mM SPB pH 7.0 with and without 150 mM NaCl to a final density of ~$10^6$ CFU/ml. 100 μL of cells are treated with different concentrations (e.g., 50-200 μg/mL) of purified test proteins. The final volume of the reaction mixture is adjusted, e.g., to 200 μL with appropriate buffers. The reaction mixture is incubated, e.g., at 37° C. for 2 hours and enumerated remaining number of viable cells by plating of appropriate dilutions on LB plate followed by overnight incubation at 37° C. The antibacterial activity is calculated by dividing initial number of untreated cells with number of residual cells in log units and plotting the data as bar graph.

b) CFU drop assay in growth media:

Gram-negative cells grown, e.g., in LB medium, until mid-log phase ($OD_{600}$ of 0.6) are diluted 100-fold in either LB or CA-MHB media to a final density of ~$10^6$ CFU/ml. 100 μL of cells are treated with different concentrations (e.g., 50-200 μg/mL) of purified test proteins. The final volume of the reaction mixture is adjusted, e.g., to 200 with appropriate buffers. The reaction mixture is incubated, e.g., at 37° C. for 2 hours, and enumerated remaining number of viable cells by plating of appropriate dilutions on LB plate followed by overnight incubation at 37° C. The antibacterial activity is calculated by dividing initial number of untreated cells with number of residual cells in log units and plotting the data as bar graph.

c) CFU drop assay in Fetal Bovine Serum (FBS):

Gram-negative cells grown, e.g., in LB medium until mid-log phase ($OD_{600}$ of ~0.6) are diluted 100-fold in FBS to a final density of ~$10^6$ CFU/ml. 100 μL of cells are treated with different concentrations (e.g., 100-400 μg/mL) of purified test proteins. The final volume of the reaction mixture is adjusted, e.g., to 200 μL with CA-MHB media. The reaction mixture is incubated, e.g., at 37° C. for 2 hours and enumerated remaining number of viable cells by plating of appropriate dilutions on LB plate followed by overnight incubation at 37° C. The antibacterial activity is calculated by dividing initial number of untreated cells with number of residual cells in log units and plotting the data as bar graph.

Minimum Inhibitory Concentration (MIC) Determination:

MIC is determined, e.g., using a modified Clinical and Laboratory Standards Institute (CLSI) broth microdilution procedure on Gram-negative cells in Cation-adjusted Mueller Hinton Broth (CA-MHB media) or in 50% FBS. A 10-point MIC is set up in microtitre plates in duplicates with two fold dilutions. Wells of 96-well polystyrene plated are coated, e.g., with 0.5% BSA for 1 hour at 37° C. and each well is inoculated, e.g., with $5\times10^5$ cells/mL Gram-negative bacteria. A positive control for growth which is devoid of test proteins is included in the assay. The microtiter plates are incubated, e.g., at 35° C. for 18-20 hrs. The MIC is defined as the minimum concentration that completely inhibits bacterial growth at the end of incubation, e.g., as determined by colorless wells after addition of Iodonitro tetrazolium (INT) dye.

```
INFORMAL SEQUENCE LISTING
NCBI accession AF190857
DNA sequence:
                                                                SEQ ID NO: 1
ATGAGTGGTG GAGACGGTCG AGGTCCGGGT AATTCAGGTC TGGGACATAA TGGTGGTCAG

GCCAGTGGGA ATGTGAACGG TACGTCTGGT AAAGGCGGCC CTTCATCAGG TGGGGGTACG

GATCCAAACA GCGGGCCGGG CTGGGGTACG ACGCATACGC CTAACGGAGA TATTCATAAC

TACAATCCGG GGGAGTTTGG TCACGGAGGG AATAAACCCG GTGGCAATGG CGGTAACAGC

GGCAATCATC CCGGTAGTTC TGGTGGCAGA CAGTCTTCGG CCACAGCGAT GGCCTTCGGT

CTGCCTGCTC TGGCTACTCC GGGCTCCGGG GGGCTGGCTT TAGCCGTTTC CGGCGATGCG

TTGTCGGCAG CCGTTGCTAG TGTGCTGGCT GCCCTGAAAG GCCGTTTAA GTTTGGTCTG

TGGGGGATTG CGATCTACGG TGTGCTGCCT TCTGAGATTG CAAAAGATGA TCCGAAAATG

ATGTCAAAAA TTATGACGTC ATTACCGGCC GATGCGGTGA CGGAGACTCC GGCAAGTACT

TTACCACTGG ACCAGGCGAC GGTTCGTGTC AGACAACGGG TTGTGGATGT GGTGAAGGAT

GAGCGGCAGC ATATTGCGGT TGTCGCAGGT CGGCCAATGA GTGTCCCTGT GGTGGATGCG

AAACCGACAA AACGTCCGGG GGTATTCAGT GTGTCGATTC CGGGTCTCCC GTCTCTGCAG

GTGAGCGTAC CGAAAGGTGT TCCGACAGCG AAAGCCCCGC CAAAAGGCAT TGTTGCTGAA

AAAGGTGATT CACGTCCGGC TGGTTTTACA GCCGGTGGTA ACTCCCGTGA GGCCGTTATT

CGTTTCCCGA AAGAGACCGG ACAGAAGCCG GTTTATGTGT CGGTGACAGA TGTTCTTACC

CCGGCACAGG TAAAACAGCG TCAGGAGGAA GAAAAGCGTC GCCAGCAGGC ATGGGACGCC

GCTCATCCGG AAGAGGGGCT GAAAAGAGAC TATGATAAAG CGAAAGCCGA GCTGGATGCC

GAAGATAAAA ATATTGCGAC CTTAAACAGC CGCATTGCAT CGACAGAGAA GGCGCTCCCC

GGTGCAAGGG CTGCTGTTCA GGAAGCCGAT AAAAAGGTGA AGAGGCAGA GGCGAATAAG

GATGATTTTG TGACTTATAA CCCTCCTCAT GAATATGGCT CCGGGTGGCA GGATCAGGTT

CGCTATCTTG ATAAGGATAT TCAGAATCAG AATGCGAAAT TAAAAGCGGC TCAGGCATCT

TTAAACGCAA TGAATGAATC CTTATCCAGA GATAAGGCTT GCACTTCCCG GGCGATGGAG

AGCCGGAAAC AAAAGGAGAA AAAAGCGAAG GATGCAGAAA ATAAGTTAAA TGAGGAAAAG

AAAAAACCTC GCAAGGGAGC TAAAGACTAC GGCCATGATT ATCATCCAGC CCCGAAAACT

GAAGACATAA AGGGACTGGG TGACCTCAAA AAAGGTACAC CTAAAACACC AATGCAGGGA

TATCTTTAA GGCGTAAACG CTGGATTGGT GATAAAGGCC GTAAGATTTA TGAATGGGAC

GGTGGAGGTA GTGAGCTTGA AGGGTATCGT GCCAGTGATG GCGAACACCT CGGGGCATTT

TCCCAGCACG CGGGTAAGCA AATTAAAGGT CCGGATCCGA AAGGGCGAAA CATTAAAAAA

GATCCTAAAA

Amino acid sequence:
                                                                SEQ ID NO: 2
MSGGDGRGPG NSGLGHNGGQ ASGNVNGTSG KGGPSSGGGT DPNSGPGWGT THTPNGDIHN

YNPGEFGHGG NKPGGNGGNS GNHPGSSGGR QSSATAMAFG LPALATPGSG GLALAVSGDA

LSAAVASVLA ALKGPFKFGL WGIAIYGVLP SEIAKDDPKM MSKIMTSLPA DAVTETPAST

LPLDQATVRV RQRVVDVVKD ERQHIAVVAG RPMSVPVVDA KPTKRPGVFS VSIPGLPSLQ

VSVPKGVPTA KAPPKGIVAE KGDSRPAGFT AGGNSREAVI RFPKETGQKP VYVSVTDVLT

PAQVKQRQEE EKRRQQAWDA AHPEEGLKRD YDKAKAELDA EDKNIATLNS RIASTEKALP
```

-continued

GARAAVQEAD KKVKEAEANK DDFVTYNPPH EYGSGWQDQV RYLDKDIQNQ NAKLKAAQAS

LNAMNESLSR DKACTSRAME SRKQKEKKAK DAENKLNEEK KKPRKGAKDY GHDYHPAPKT

EDIKGLGDLK KGTPKTPMQG GGGRRKRWIG DKGRKIYEWD SQHGELEGYR ASDGEHLGAF

DPKTGKQIKG PDPKGRNIKK YL

NCBI accession: NC_002610.1
DNA sequence:

SEQ ID NO: 3

ATGGGTGGTG GATTTAACTA TAACGGGGAA GGTGCTACTG GCACCGGATT GGATCGTGAT

CCATATGTTC GCGACAGCAA TGGTAATGCT ATTGGTGTTA AATCACGCTA TCACGCGGAG

TCCTATGGGA CGTCAAGTCC AGCCTTAGGG CCTAATGGCG CTATTCAGAT TACTGCTGGG

GTTATTGCTG TGCCTGGAGA TAAGCCCCGA CCTGACGGTG GTAGTGGTGG TGGGAATACT

GTTAACACCG GACCTGCAGG ACAGCTCCTG GTGATGAATA AAGGTCAGCT TGGATACTGG

GAAACTCGTT CTACGGGCGC GGGTAACAAT GAGCATAATA CGAGTGTATT TGTTGCTGTA

GGTCCTTCTG AGGCAGAAAA AACTGCTTCT GCAGAGAAGG CGTTAAAGGA AAAACAGCAG

GCAGAAGCAG CAGCAAAAGA CTTTGCGGCT AAAACTGCTG CCGCATCAGC CACGGCGGAA

AAAGAACGCC AGCAGGCAAT TGCTGCTGCA ACTGCAGCGG GTCAGCATCA GTCAGTTTCT

GATGCCCGTA ATAGCCTGAA TAACGCGACG TCAGATGTGT CTCGTCTGAA ATCAGCTGCA

GACAGTGCAC TGCAGGAGGC AAAGGCAAAA CGGAAGGCTG CTATTGATGC TGTACCTGTT

GCAACCCAGG CGGAAAATAA ATATCAGGAG CTGCAGCAGA AGATTAAAGG CCTGAAGCTG

AAAAATGGTG AGTATGGTAC GGATAAATGG GAAATAATTG CTCTAATAA GGAGCATGAT

CACTGGGGAT ACAGGTTTTA TCCATCCGGA ATTACCAAAG CTCAGGTTGA TGCGGCGCAG

ATCGATGCTG TGAATAAGCG AAATCAGGCT ACCAGTCTTG CCAGTCAGGC AACAGCAGCA

GAACAGGACA GCCTGAAAGC TACAGCTGCC TATAATGCGG CAGAAACGCG CCGTCAGGCT

GCTCAGGCGG CGTTAAATTC TGCTGAACAG GCTGCTGCTG CTAACGTAA GCGGCAGGAA

GCTGAGGCGG CTGCAGCAGC TGCTGCTGAG AAAAAACGTC AGGCAGACGC AGCAGCAAAA

GCTGCAGAGG AAGCGCGTGC GGCAGCGGAA AAAGCCAGGC TGATGCAGGA GCGTCAGGCA

GCAGCAGATA AGCTGAAATC CACAGATATT CAGTCTGTTC GCGGGATCCC GTCTACGGCT

GCGCCTGCAG CGTCACCCAT TTCCTGGGCC GTTGCATCAC TTGGTGGTAT ATCGCTGGAT

AGTGTTACTG CAGGGAAAGC ATGGACGCAG ATTGCTGAGG TGATGGCTAA ACTACGAGGT

ATTGCCGGTG CGAGTCTTGT TGGTCCCGTG GTGGCAACTG CTGTAGGGCT GTTTTGGTCA

CGTGATGTTG GTATTGGCAG TGATGTGGTG CCCGGACGTG ACATCAGCGG GCTGATGCCG

GGTGATGCAC TGTCATTACC TGATCTGGCC ACTTTGATTA AAGCTGCTGA CAGTAAAACG

GGTGTCAGTA TGCCGGTTCG AGGCCGGATT ATCGTGCGTG AAGGCGATTA TCTGGAGTCT

CAGTTCGTTC GAACACCTGT TGCCGGTAGT GTTCCGGTTG TTCGGGCTGC TCTGGATAAA

GCTACTGGTT ACTGGGGATA TACGTTGCCG GCGATACAGG GTGTGCCCGG ACAGACAATA

CTGGTGAGTC CGTCAGATGC GCCGGGCGTT AATGGTCCTC TGGGACTTGC TGGGCCGGTT

CCTTTGCCTG AAACTATTAT ACATACCGGT GGGCAAACTA CGGTTCCTCA GGGGGGGACT

GTGACAGTTT CCCCGGCAGA AGACGATATT GATTTCAATG ATTTGATTCT GGTATTTCCG

CCCGGAGTCCG GTCTTAAACC GTTGTATGTG ATGTACCGTA GCCCTCGTAA CATGCCGGGG

ACAGCCAGTG GTAAAGGTCA GAACGTTGGA AATAACTGGA TGGGGGGGAC CAGTACCGGG

GATGGTGCTC CTGTTCCTTC CCAGATTGCA GATAAATTAC GTGGGAAGGC TTTCGGTAGT

TTTGATTCTT TCTGTCGGGC TTTCTGGAAA GCGGTTGCTG CTGATCCGGA CCTCAGTAAG

-continued

```
CAGTTTTATC CTGATGATAT AGAGCGAATG AAATTAGGGC GAGCTCCAAC AGTTCGATTC

CGAGATTCTG TAGGTAAAAG GGTTAAGGTT GAACTACACC ATAAAGTTGA AATTTCTAAA

GGTGGTGATG TCTATAACGT AGATAACCTG AATGCATTAA CACCTAAACG TCATATTGAA

ATTCATAAGG GGAACTGA
```

Amino acid sequence:

SEQ ID NO: 4

```
MGGGFNYNGE GATGTGLDRD PYVRDSNGNA IGVKSRYHAE SYGTSSPALG PNGAIQITAG

VIAVPGDKPR PDGGSGGGNT VNTGPAGQLL VMNKGQLGYW ETRSTGAGNN EHNTSVFVAV

GPSEAEKTAS AEKALKEKQQ AEAAAKDFAA KTAAASATAE KERQQAIAAA TAAGQHQSVS

DARNSLNNAT SDVSRLKSAA DSALQEAKAK RKAAIDAVPV ATQAENKYQE LQQKIKGLKL

KNGEYGTDKW EIIGSNKEHD HWGYRFYPSG ITKAQVDAAQ IDAVNKRNQA TSLASQATAA

EQDSLKATAA YNAAETRRQA AQAALNSAEQ AAAAERKRQE AEAAAAAAE KKRQADAAAK

AAEEARAAAE KARLMQERQA AADKLKSTDI QSVRGIPSTA APAASPISWA VASLGGISLD

SVTAGKAWTQ IAEVMAKLRG IAGASLVGPV VATAVGLEWS RDVGIGSDVV PGRDISGLMP

GDALSLPDLA TLIKAADSKT GVSMPVRGRI IVREGDYLES QFVRTPVAGS VPVVRAALDK

ATGYWGYTLP AIQGVPGQTI LVSPSDAPGV NGPLGLAGPV PLPETIIHTG GQTTVPQGGT

VTVSPAEDDI DFNDLILVFP PESGLKPLYV MYRSPRNMPG TASGKGQNVG NNWMGGTSTG

DGAPVPSQIA DKLRGKAFGS FDSFCRAFWK AVAADPDLSK QFYPDDIERM KLGRAPTVRF

RDSVGKRVKV ELHHKVEISK GGDVYNVDNL NALTPKRHIE IHKGN
```

NCBI accession: AY578793.1
DNA sequence:

SEQ ID NO: 5

```
ATGGCAGATA ATCAACCGGT TCCTCTTACC CCCGCACCAC CTGGAATGGT ATCACTTGGC

GTCAATGAAA ACGGCGAAGA GGAGATGACT GTCATTGGTG GAGATGGCAG CGGCACAGGG

TTTTCTGGGA ATGAAGCACC TATTATTCCT GGAAGTGGTA GCCTCCAGGC CGACTTAGGT

AAAAAGTCTC TAACCCGACT ACAGGCTGAA AGTTCAGCAG CAATTCATGC GACTGCAAAA

TGGACTACAG AGAATCTTGC AAAAACGCAG GCTGCGCAGG CTGAAAGGGC CAAGGCTGCC

ATGCTTTCTC AGCAGGCAGC AAAAGCAAAA CAGGCCAAAC TCACGCTACA TCTGAAAGAT

GTAGTGGATC GCGCGCTTCA GAACAACAAA ACGCGGCCTA CTGTTATTGA TCTTGCTCAT

CAGAATAACC AACAAATGGC CGCAATGGCC GAGTTTATAG GCCGTCAAAA GGCAATTGAA

GAAGCTCGTA AAAAGGCTGA AGGGAAGCC AAAAGGGCTG AAGAAGCTTA TCAGGCTGCT

TTGAGAGCGC AGGAAGAAGA ACAGCGCAAG CAGGCAGAAA TTGAACGGAA ATTGCAGGAG

GCAAGGAAGC AAGAGGCAGC GGCAAAAGCA AAAGCTGAAG CTGACAGAAT TGCGGCTGAG

AAAGCTGAAG CAGAGGCAAG AGCTAAAGCG AAGCTGAGC GACGGAAAGC AGAGGAGGCT

CGAAAGGCGC TTTTTGCAAA GGCTGGGATT AAGGACACTC CTGTTTATAC ACTGGAGAAG

ACAAAAGCAG CCACTACGTT GTTTTTAACA CCGGGTGTTA GGTTACTGAA TCGTGCTCCA

GCGATGATAC AGTTATCCGC TTTGGCTGCA GAAATTAATG GCGTCTTAAC TACTGCTGCT

AGTGCAGTAA TGACGGCTAC TGCTGAATTC TCAGGTTGGA TTGCCTCAGC GTTATGGCGA

GGTGTAGCTG GTGTTGCAAC AGCTAGTACT GTTGGTCCCA TGGTTGCCGC AGCATCGACG

CTATTCTTTT CACCTCGCGC AGGTGGCGGA AGCGACAGTA AGGTTCCTGG TAGGGATATC

GAGATGTTGG CTGCGCAAGC CAGGTTGTTC ACGGCGGGTA AGCTGAGTAT CGAACATGAA

GAGCGTCAAC CTCCCGGTAC GTGGCTTCAT CTCTTCGGAA ACTGATGGGC GCCAGTCTCT

GATGCTTGTA AAAACCGGTT CTGATGGAGT ACCTTCCACT GTTCCTGTAT TGGATGCTGT
```

-continued

```
ACGTGACAGT ACTACTGGCC TTGATAAAAT AACGGTACCG GCGATGTCTG GTGCGCCGTC

GCGGACCATC CTCGTGAATC CGGTTCCAAT TGGACCTGCT GCTCCGTGGC ATACCGGCAA

TAGCGGGCCA GTGCCAGTAA CACCTGTTCA CACCGGTACA GAGGTGAAGC AGGCTGACAG

TATCGTCACG ACAACTTTGC CGATTGCAGA CATTCCGCCA CTACAGGACT TCATCTACTG

GCAGCCGGAT GCTTCTGGGA CAGGTGTTGA ACCTATTTAT GTAATGACTA GTCAACCCAG

GAAAGGAGTA AAAGACTACG GACATGATTA TCATCCGGCT CCAAAAACTG AAGAAATTAA

GGGGTTGGGG GAGTTGATTG AGTCTCGGAA AAAAACTCCA AAACAAGGGG GAGGTGGACG

ACGAGATCGA TGGGTGGGAG ATAAAGGACG AAAAATCTAT GAGTGGGATT CGCAGCATGG

AGAACTTGAA GGTTACAGAG CTAGCGACGG CTCTCATCTT GGAGCATTTG ATCCAAACAC

CGGCAAGCAA CTTAAAGGTC CGGACCCTAA ACGTAACATC AAAAAATATC TTTGA
```

Amino acid sequence: SEQ ID NO: 6

```
MADNQPVPLT PAPPGMVSLG VNENGEEEMT VIGGDGSGTG FSGNEAPIIP GSGSLQADLG

KKSLTRLQAE SSAAIHATAK WTTENLAKTQ AAQAERAKAA MLSQQAAKAK QAKLTLHLKD

VVDRALQNNK TRPTVIDLAH QNNQQMAAMA EFIGRQKAIE EARKKAEREA KRAEEAYQAA

LRAQEEEQRK QAEIERKLQE ARKQEAAAKA KAEADRIAAE KAEAEARAKA EAERRKAEEA

RKALFAKAGI KDTPVYTLEK TKAATTLFLT PGVRLLNRAP AMIQLSALAA EINGVLTTAA

SAVMTATAEF SGWIASALWR GVAGVATAST VGPMVAAAST LFFSPRAGGG SDSKVPGRDI

EMLAAQARLF TAGKLSIEPG MKSVNLPVRG FISSETDGRQ SLMLVKTGSD GVPSTVPVLD

AVRDSTTGLD KITVPAMSGA PSRTILVNPV PIGPAAPWHT GNSGPVPVTP VHTGTEVKQA

DSIVTTTLPI ADIPPLQDFI YWQPDASGTG VEPIYVMTSQ PRKGVKDYGH DYHPAPKTEE

NTGKQLKGPD PKRNIKKYL GRRDRWVGDK GRKIYEWDSQ HGELEGYRAS DGSHLGAFDP

IKGLGELIES RKKTPKQGGG
```

NCBI accession: AY578792
DNA sequence: SEQ ID NO: 7

```
ATGAGTGATA TCACATATAA TCCTGAGGAC TATAACAATG GTATACCACC TGAGCCGGGT

CTGGTGTGGA AGCCGGGAGG CTCATTCCCC AATGGCAGTT ACGTTCCCGG CTCATGGGGC

TGGCCAACGC GCGGATACGA TGTTCCTCCG CTGCCGGGTG ATACCGAAAT GCTGACGGTC

ACCCCAAAAG GAACGCCGGC TGATACCTGG CCTAAAAGAC CTGATATCAA AGAGTGGTAT

GTTCCGGGTG AAAAACCCTT CGACCCGTCA ACAGGTAATG GATGGGTGCC TGATGTGGAC

GGCTACGCCG AATCGCTGCC TGCCGGTATA CCGGCTGTGG TACAGGCTGC AATCAGTAAG

GTGAAAGGTG CGCCACTGAA AGGCGGCATG TCCGCCGTGG ATATCTGGAA ACTGAAACCC

GCAACGGAGT ACCGGGGAG ATTTAACAGC ACCGACCCGG CATTCAGCTG GTTTCCGGTT

CGGGCGCTGA CTGACACTGA TATATCTGCG ATGCCCGTTG CCCCTGAGAC TGTTCCGGTG

CATACCCGTA TCCTTGATAA TGTTCATGAT GGTGTACAGT TGGTTTCTGC GGTGTTTGCG

GGTAGCATGC AGTACAATCT GCCGGTGGTG AAAGCGCAGG CCACTGCCGG CAGTGATTAT

TACACTATCG GACGTCTGCC GGGCATCATG AGTGCTTTCA CATTCTCTTT CTACACAAAA

GGAACACCAC AGGACTCCCG TTTCTTCCGG GATACAGTGA AGCCGGGGG AGATTTACGC

GAAGCAGGCT TCACTGTGGG GGCCAATACC AGCGATTTTA TCATCTGGTT CCGCAGGGG

AGCGGACTGG AGCCGCTGTA TTTTTCCATG ACCATGAATA TGCCGGCTGG GCCGCTGCAG

CGTCGCCAGG AAGCCGAAAA CAAGGCCAGA GCAGAAGCTG ACAGGCTCCG GCAGAGGCG

GAGGCAAAAA TTCGCGCTGA AGCAGAGGCC CGGGCGAAAG CAGAAGCAGA ACGCAAAGCC
```

```
CTGTTCGCTA AGGCCGGTAT TCAGGATACA CCGGTTTACA CGCCGGAGAT GGTGAAGGCG

GCAAATGCGG CGCTGTCTGC CGGAGGCTCA ATGGCGCTCA GCCGGGCCCC GGGGATGATA

CAGCACTCTG CTGCAGGCGT GGGGACGCTA CCCTTCAACA GTAGTCTGGC GGGATGGGAA

GCCGGCGCGC TCTGGCGCGG TGTCGACGTG CTTGCCAGGA TCGCGCCGGT CGCGTCCGCC

GTGGCCACGG TTGCCACAGT GCTCACCCTT GTCAGGGCTG CACTGGATAT CCCTGCAGCC

GGCGAGGGCA GTGACAGGGT TCCCGGACGC AACATTGACA TGCTTGCCGC CCAGGCCAGC

CTGTACACGG CCATGAAGAC GAACATTCAG CCGGGGATGA AGACCGTTGA CCTGCCAGTC

AGGGGATATA TCTCGTATGA CGGCAACGGC CGGCAGTCGG TCAACTTGGT CAGGACGGGG

ACGGGCGGGG TTTCGGCCAC GGTGCCGGTG CTGAGTGCCG TGCGTGACAA AACCACCGGC

CTGGATAAAA TCACGGTACC GGCCGTGGCG GGCGCCCCGT CGCGGACCAT CCTGATTAAC

CCTGTACCGG TCGGTCCTGC GACACCATCG CATACCGGCA GCAGTACGCC GGTTCCGGTG

ACGCCGGTGC ACACTGGTAC CGATGTTAAG CAGGCGGACA GCATCGTCAC CACAACGTTG

CCGGCGGCAG ATATTCCTGC GCTGCAGGAC TTCATCTACT GGCAGCCGGA TGCAACCGGG

ACGGGCGTGG AACCCATCTA TGTCATGCTG AGTGATCCGT GGATTCGGG GAAATATACC

CGCAGGCAGC TCCAGAAGAA GTACAAGCAT GCTATCGATT TGGTATCAC AGATACGAAG

ATAAATGGTG AAACACTTAC TAAGTTCCGG GATGCAATTG AAGCACATCT TTCAGATAAG

GATACCTTTG AAAAGGAAC ATATCGGCGT GATAAGGGAT CGAAGGTTTA TTTCAATCCT

AAAACAATGA ATGCTGTTAT TATTCAGGCT AATGGTGACT TTCTGTCTGG ATGGAAAATT

AATCCTGCGG CAGATAATGG TAGAATTTAT TTAGAAACGG GTGATTTATG A
```

Amino acid sequence: SEQ ID NO: 8

```
MSDITYNPED YNNGIPPEPG LVWKPGGSFP NGSYVPGSWG WPTRGYDVPP LPGDTEMLTV

TPKGTPADTW PKRPDIKEWY VPGEKPFDPS TGNGWVPDVD GYAESLPAGI PAVVQAAISK

VKGAPLKGGM SAVDIWKLKP ATEYPGRENS TDPAFSWFPV RALTDTDISA MPVAPETVPV

HTRILDNVHD GVQFVSAVFA GSMQYNLPVV KAQATAGSDY YTIGRLPGIM SAFTFSFYTK

GTPQDSRFFR DTVKAGGDLR EAGFTVGANT SDFIIWFPQG SGLEPLYFSM TMNMPAGPLQ

RRQEAENKAR AEADRLRAEA EAKIRAEAEA RAKAEAERKA LFAKAGIQDT PVYTPEMVKA

ANAALSAGGS MALSRAPGMI QHSAAGVGTL PFNSSLAGWE AGALWRGVDV LARIAPVASA

VATVATVLTL VRAALDIPAA GEGSDRVPGR NIDMLAAQAS LYTAMKTNIQ PGMKTVDLPV

RGYISYDGNG RQSVNLVRTG TGGVSATVPV LSAVRDKTTG LDKITVPAVA GAPSRTILIN

PVPVGPATPS HTGSSTPVPV TPVHTGTDVK QADSIVTTTL PAADIPALQD FIYWQPDATG

TGVEPIYVML SDPLDSGKYT RRQLQKKYKH AIDFGITDTK INGETLTKFR DAIEAHLSDK

DTFEKGTYRR DKGSKVYFNP KTMNAVIIQA NGDFLSGWKI NPAADNGRIY LETGDL
```

DNA sequence of Klebicin CCL along with immunity gene:
>AF190857.1:166-1854 *Klebsiella pneumoniae* cloacin operon, complete
sequence, 1956 bases

SEQ ID NO: 9

```
ATGAGTGGTG GAGACGGTCG AGGTCCGGGT AATTCAGGTC TGGGACATAA TGGTGGTCAG

GCCAGTGGGA ATGTGAACGG TACGTCTGGT AAAGGCGGCC CTTCATCAGG TGGGGGTACG

GATCCAAACA GCGGGCCGGG CTGGGGTACG ACGCATACGC CTAACGGAGA TATTCATAAC

TACAATCCGG GGGAGTTTGG TCACGGAGGG AATAAACCCG GTGGCAATGG CGGTAACAGC

GGCAATCATC CCGGTAGTTC TGGTGGCAGA CAGTCTTCGG CCACAGCGAT GGCCTTCGGT

CTGCCTGCTC TGGCTACTCC GGGCTCCGGG GGCTGGCTT TAGCCGTTTC CGGCGATGCG

TTGTCGGCAG CCGTTGCTAG TGTGCTGGCT GCCCTGAAAG GGCCGTTTAA GAAAAGAGAC
```

-continued

```
TATGATAAAG CGAAAGCCGA GCTGGATGCC GAAGATAAAA ATATTGCGAC CTTAAACAGC

CGCATTGCAT CGACAGAGAA GGCGCTCCCC GGTGCAAGGG CTGCTGTTCA GGAAGCCGAT

AAAAAGGTGA AGAGGCAGA GGCGAATAAG GATGATTTTG TGACTTATAA CCCTCCTCAT

GAATATGGCT CCGGGTGGCA GGATCAGGTT CGCTATCTTG ATAAGGATAT TCAGAATCAG

AATGCGAAAT TAAAAGCGGC TCAGGCATCT TTAAACGCAA TGAATGAATC CTTATCCAGA

GATAAGGCTT GCACTTCCCG GCGATGAG AGCCGGAAAC AAAAGGAGAA AAAAGCGAAG

GATGCAGAAA ATAAGTTAAA TGAGGAAAAG AAAAAACCTC GCAAGGGAGC TAAAGACTAC

GGCCATGATT ATCATCCAGC CCCGAAAACT GAAGACATAA AGGGACTGGG TGACCTCAAA

AAAGGTACAC CTAAAACACC AATGCAGGGA GGTGGAGGTA GGCGTAAACG CTGGATTGGT

GATAAAGGCC GTAAGATTTA TGAATGGGAC TCCCAGCACG GTGAGCTTGA AGGGTATCGT

GCCAGTGATG GCGAACACCT CGGGGCATTT GATCCTAAAA CGGGTAAGCA AATTAAAGGT

CCGGATCCGA AAGGGCGAAA CATTAAAAAA TATCTTTAAg aggtaagtat gggacttaaa ttaaatttaa cctggtttga taagaaaact gaagagttta aaggggaaga gtattctaaa gactttggtg atgatggttc tgtcattgaa agtcttggga tgcctttaaa ggataatatt aacaatggtt gttttgatgt gaaaaatgag tgggtttcat tattgcaacc ctactttaaa cataaaatca atctttctga tagttcatat tttgtttcat ttgattatcg ggatggtaac tggtaa
```

Amino acid sequence of klebicin CCL:
SEQ ID NO: 10

```
MSGGDGRGPG NSGLGHNGGQ ASGNVNGTSG KGGPSSGGGT DPNSGPGWGT THTPNGDIHN

YNPGEFGHGG NKPGGNGGNS GNHPGSSGGR QSSATAMAFG LPALATPGSG GLALAVSGDA

LSAAVASVLA ALKGPFKFGL WGIAIYGVLP SEIAKDDPKM MSKIMTSLPA DAVTETPAST

LPLDQATVRV RQRVVDVVKD ERQHIAVVAG RPMSVPVVDA KPTKRPGVFS VSIPGLPSLQ

VSVPKGVPTA KAPPKGIVAE KGDSRPAGFT AGGNSREAVI RFPKETGQKP VYVSVTDVLT

PAQVKQRQEE EKRRQQAWDA AHPEEGLKRD YDKAKAELDA EDKNIATLNS RIASTEKALP

GARAAVQEAD KKVKEAEANK DDFVTYNPPH EYGSGWQDQV RYLDKDIQNQ NAKLKAAQAS

LNAMNESLSR DKACTSRAME SRKQKEKKAK DAENKLNEEK KKPRKGAKDY GHDYHPAPKT

EDIKGLGDLK KGTPKTPMQG GGGRRKRWIG DKGRKIYEWD SQHGELEGYR ASDGEHLGAF

DPKTGKQIKG PDPKGRNIKK YL
```

6. Klebicin CCL TDRD + Kleb B KD + Imm: 2107 bases
DNA Sequence:
SEQ ID NO: 11

```
ATGAGTGGTG GAGACGGTCG AGGTCCGGGT AATTCAGGTC TGGGACATAA TGGTGGTCAG

GCCAGTGGGA ATGTGAACGG TACGTCTGGT AAAGGCGGCC CTTCATCAGG TGGGGGTACG

GATCCAAACA GCGGGCCGGG CTGGGGTACG ACGCATACGC CTAACGGAGA TATTCATAAC

TACAATCCGG GGGAGTTTGG TCACGGAGGG AATAAACCCG GTGGCAATGG CGGTAACAGC

GGCAATCATC CCGGTAGTTC TGGTGGCAGA CAGTCTTCGG CCACAGCGAT GGCCTTCGGT

CTGCCTGCTC TGGCTACTCC GGGCTCCGGG GGCTGGCTT TAGCCGTTTC CGGCGATGCG

TTGTCGGCAG CCGTTGCTAG TGTGCTGGCT GCCCTGAAAG GCCGTTTAA GTTTGGTCTG

TGGGGGATTG CGATCTACGG TGTGCTGCCT TCTGAGATTG CAAAGATGA TCCGAAAATG

ATGTCAAAAA TTATGACGTC ATTACCGGCC GATGCGGTGA CGGAGACTCC GGCAAGTACT

TTACCACTGG ACCAGGCGAC GGTTCGTGTC AGACAACGGG TTGTGGATGT GGTGAAGGAT

GAGCGGCAGC ATATTGCGGT TGTCGCAGGT CGGCCAATGA GTGTCCCTGT GGTGGATGCG
```

-continued

AAACCGACAA AACGTCCGGG GGTATTCAGT GTGTCGATTC CGGGTCTCCC GTCTCTGCAG
GTGAGCGTAC CGAAAGGTGT TCCGACAGCG AAAGCCCCGC CAAAAGGCAT TGTTGCTGAA
AAAGGTGATT CACGTCCGGC TGGTTTTACA GCCGGTGGTA ACTCCCGTGA GGCCGTTATT

CGTTTCCCGA AAGAGACCGG ACAGAAGCCG GTTTATGTGT CGGTGACAGA TGTTCTTACC

CCGGCACAGG TAAAACAGCG TCAGGAGGAA GAAAAGCGTC GCCAGCAGGC ATGGGACGCC
GCTCATCCGG AAGAGGGGCT GAAAAGAGAC TATGATAAAG CGAAAGCCGA GCTGGATGCC
GAAGATAAAA ATATTGCGAC CTTAAACAGC CGCATTGCAT CGACAGAGAA GGCGCTCCCC

GGTGCAAGGG CTGCTGTTCA GGAAGCCGAT AAAAAGGTGA AAGAGGCAGA GGCGAATAAG

GATGATTTTG TGACTTATAA CCCTCCTCAT GAATATGGCT CCGGGTGGCA GGATCAGGTT
CGCTATCTTG ATAAGGATAT TCAGAATCAG AATGCGAAAT TAAAAGCGGC TCAGGCATCT
TTAAACGCAA TGAATGAATC CTTATCCAGA GATAAGGCTT GCACTTCCCG GGCGATGGAG
AGCCGGAAAC AAAAGGAGAA AAAAGCGAAG GATGCAGAAA ATAAGTTAAA TGAGGAAAAG
AAAAAACCTC GCAAGGGAGC TAAAGACTAC GGCCATGAT
G GTCTTAAACC GTTGTATGTG
ATGTACCGTA GCCCTCGTAA CATGCCGGGG ACAGCCAGTG GTAAAGGTCA GAACGTTGGA
AATAACTGGA TGGGGGGGAC CAGTACCGGG GATGGTGCTC CTGTTCCTTC CCAGATTGCA
GATAAATTAC GTGGGAAGGC TTTCGGTAGT TTTGATTCTT TCTGTCGGGC TTTCTGGAAA
GCGGTTGCTG CTGATCCGGA CCTCAGTAAG CAGTTTTATC CTGATGATAT AGAGCGAATG
AAATTAGGGC GAGCTCCAAC AGTTCGATTC CGAGATTCTG TAGGTAAAAG GGTTAAGGTT
GAACTACACC ATAAAGTTGA AATTTCTAAA GGTGGTGATG TCTATAACGT AGATAACCTG

AATGCATTAA CACCTAAACG TCATATTGAA ATTCATAAGG GGAACTGA aa tcgctaataa aactttggct gactatacag agcaggaatt tattgagttt atcgaaaaaa ttaaaaaggc agactttgct actgagtctg agcatgatga ggctatttat gagttcagcc agttgactga gcatccagat gcttgggatc ttatttatca tectcaagca ggagccgata actctcctgc tggtgttgta aaaacagtaa aagagtggcg agcagctaac ggtaagccag gttttaaaaa atcgtga Kleb CCL TD RBD (1-1419); Klebicib B KD (1420-1849);
Klebicibn B Immunity protein (1850-end)

SEQ ID NO: 12

Amino Acid sequence; Theoretical pI/Mw: 9.54/65021.95
MSGGDGRGPG NSGLGHNGGQ ASGNVNGTSG KGGPSSGGGT DPNSGPGWGT THTPNGDIHN

YNPGEFGHGG NKPGGNGGNS GNHPGSSGGR QSSATAMAFG LPALATPGSG GLALAVSGDA

LSAAVASVLA ALKGPFKFGL WGIAIYGVLP SEIAKDDPKM MSKIMTSLPA DAVTETPAST

LPLDQATVRV RQRVVDVVKD ERQHIAVVAG RPMSVPVVDA KPTKRPGVFS VSIPGLPSLQ

VSVPKGVPTA KAPPKGIVAE KGDSRPAGFT AGGNSREAVI RFPKETGQKP VYVSVTDVLT

PAQVKQRQEE EKRRQQAWDA AHPEEGLKRD YDKAKAELDA EDKNIATLNS RIASTEKALP

GARAAVQEAD KKVKEAEANK DDFVTYNPPH EYGSGWQDQV RYLDKDIQNQ NAKLKAAQAS

LNAMNESLSR DKACTSRAME SRKQKEKKAK DAENKLNEEK KKPRKGAKDY GHDGLKPLYV

MYRSPRNMPG TASGKGQNVG NNWMGGTSTG DGAPVPSQIA DKLRGKAFGS FDSFCRAFWK

AVAADPDLSK QFYPDDIERM KLGRAPTVRF RDSVGKRVKV ELHHKVEISK GGDVYNVDNL

NALTPKRHIE IHKGN

-continued

P623: S5 TD-RD-Linker-GP36 CD-his: 1590 bases

SEQ ID NO: 13

ATGTCCAATG ACAACGAAGT ACCTGGTTCC ATGGTTATTG TCGCACAAGG TCCAGACGAT

CAATACGCAT ACGAGGTTCC CCCTATCGAT AGCGCGGCCG TTGCCGGGAA TATGTTTGGC

GACTTAATTC AAAGAGAAAT ATATCTACAG AAAAACATTT ATTATCCAGT CCGATCTATT

TTTGAACAAG GAACAAAAGA AAAGAAGGAG ATCAACAAGA AAGTATCTGA TCAAGTCGAT

GGCTTGCTAA AGCAGATCAC TCAAGGAAAA AGGGAGGCCA CAAGGCAAGA GCGAGTCGAT

GTCATGTCGG CAGTCCTGCA CAAGATGGAA TCTGATCTTG AAGGATACAA AAAGACCTTT

ACCAAAGGCC CATTCATTGA CTACGAAAAG CAGTCAAGCC TCTCCATCTA TGAGGCCTGG

GTCAAGATCT GGGAGAAGAA CTCTTGGGAA GAAAGAAAGA AGTACCCTTT TCAGCAGCTT

GTTAGAGATG AACTGGAGCG GGCGGTTGCC TACTACAAAC AAGATTCACT CTCTGAAGCG

GTAAAAGTGC TAAGACAGGA GCTCAACAAG CAAAAGCGC TAAAGGAAAA AGAGGACCTC

TCTCAACTGG AGCGGGACTA CAGAACCCGA AAGGCGAATC TCGAGATGAA AGTACAATCC

GAGCTTGATC AAGCGGGAAG TGCTTTGCCT CCATTGGTCA GTCCAACGCC AGAGCAATGG

CTTGAACGTG CCACAAGACT GGTTACGCAA GCAATTGCTG ATAAAAAGCA GCTGCAGACC

ACAAACAATA CTCTTATCAA GAATTCCCCA ACCCCTCTAG AAAAGCAGAA AGCCATCTAC

AATGGTGAGC TACTTGTGGA TGAGATAGCC AGTCTACAGG CCCGCTTAGT TAAGCTGAAC ggaggaggag gatcaGGTGT GGCCCTGGAC CGCACGCGGG TTGATCCCCA GGCAGTCGGC

AACGAGGTGC TCAAGCGCAA CGCGGATAAG CTGAATGCGA TGCGGGGCGC CGAGTACGGT

GCCAACGTCA AGGTCAGCGG CACGGACATT CGCATGAACG GGGTAACAG TGCCGGCATG

CTGAAGCAGG ACGTGTTCAA CTGGCGGAAG GAACTGGCTC AGTTCGAGGC TTACCGAGGG

GAGGCGTATA AGGATGCCGA TGGTTATAGT GTGGGCCTGG GCATTACCT GGGCAGTGGC

AATGCTGGGG CAGGTACTAC AGTCACGCCT GAGCAAGCCG CGCAGTGGTT CGCCGAGGAC

ACCGACCGCG CACTCGACCA GGGTGTGAGG TTGGCCGACG AGCTGGGCGT TACGAACAAT

GCCTCTATCC TGGGATTGGC CGGTATGGCC TTCCAGATGG GCGAAGGACG TGCCCGGCAG

TTCCGTAACA CCTTCCAGGC GATCAAGGAT CGCAACAAGG AAGCCTTCGA GGCTGGTGTG

CGAAACAGCA AGTGGTACAC GCAGACGCCC AACCGGGCCG AGGCATTCAT CAAGCGCATG

GCGCCCCACT TCGATACACC GAGTCAAATC GGTGTCGATT GGTACAGCGC CGCAACAGCG

GAGCTCGAGC ACCACCACCA CCACCACTAA

Protein; Theoretical pI/Mw: 6.56/59443.77

SEQ ID NO: 14

MSNDNEVPGS MVIVAQGPDD QYAYEVPPID SAAVAGNMFG DLIQREIYLQ KNIYYPVRSI

FEQGTKEKKE INKKVSDQVD GLLKQITQGK REATRQERVD VMSAVLHKME SDLEGYKKTF

TKGPFIDYEK QSSLSIYEAW VKIWEKNSWE ERKKYPFQQL VRDELERAVA YYKQDSLSEA

VKVLRQELNK QKALKEKEDL SQLERDYRTR KANLEMKVQS ELDQAGSALP PLVSPTPEQW

LERATRLVTQ AIADKKQLQT TNNTLIKNSP TPLEKQKATY NGELLVDEIA SLQARLVKLN

GGGGSGVALD RTRVDPQAVG NEVLKRNADK LNAMRGAEYG ANVKVSGTDI RMNGGNSAGM

LKQDVFNWRK ELAQFEAYRG EAYKDADGYS VGLGHYLGSG NAGAGTTVTP EQAAQWFAED

TDRALDQGVR LADELGVTNN ASILGLAGMA FQMGEGRARQ FRNTFQAIKD RNKEAFEAGV

RNSKWYTQTP NRAEAFIKRM APHFDTPSQI GVDWYSAATA ELEHHHHHH

P624: S5 TD-RD-Link-GP36 CD without his tag: 1572 bases

SEQ ID NO: 15

ATGTCCAATG ACAACGAAGT ACCTGGTTCC ATGGTTATTG TCGCACAAGG TCCAGACGAT

CAATACGCAT ACGAGGTTCC CCCTATCGAT AGCGCGGCCG TTGCCGGGAA TATGTTTGGC

-continued

```
GACTTAATTC AAAGAGAAAT ATATCTACAG AAAAACATTT ATTATCCAGT CCGATCTATT

TTTGAACAAG GAACAAAAGA AAAGAAGGAG ATCAACAAGA AAGTATCTGA TCAAGTCGAT

GGCTTGCTAA AGCAGATCAC TCAAGGAAAA AGGGAGGCCA CAAGGCAAGA GCGAGTCGAT

GTCATGTCGG CAGTCCTGCA CAAGATGGAA TCTGATCTTG AAGGATACAA AAAGACCTTT

ACCAAAGGCC CATTCATTGA CTACGAAAAG CAGTCAAGCC TCTCCATCTA TGAGGCCTGG

GTCAAGATCT GGGAGAAGAA CTCTTGGGAA GAAAGAAAGA AGTACCCTTT TCAGCAGCTT

GTTAGAGATG AACTGGAGCG GGCGGTTGCC TACTACAAAC AAGATTCACT CTCTGAAGCG

GTAAAAGTGC TAAGACAGGA GCTCAACAAG CAAAAAGCGC TAAAGGAAAA AGAGGACCTC

TCTCAACTGG AGCGGGACTA CAGAACCCGA AAGGCGAATC TCGAGATGAA AGTACAATCC

GAGCTTGATC AAGCGGGAAG TGCTTTGCCT CCATTGGTCA GTCCAACGCC AGAGCAATGG

CTTGAACGTG CCACAAGACT GGTTACGCAA GCAATTGCTG ATAAAAAGCA GCTGCAGACC

ACAAACAATA CTCTTATCAA GAATTCCCCA ACCCCTCTAG AAAAGCAGAA AGCCATCTAC

AATGGTGAGC TACTTGTGGA TGAGATAGCC AGTCTACAGG CCCGCTTAGT TAAGCTGAAC ggaggaggag gatcaGGTGT GGCCCTGGAC CGCACGCGGG TTGATCCCCA GGCAGTCGGC

AACGAGGTGC TCAAGCGCAA CGCGGATAAG CTGAATGCGA TGCGGGGCGC CGAGTACGGT

GCCAACGTCA AGGTCAGCGG CACGGACATT CGCATGAACG GGGTAACAG TGCCGGCATG

CTGAAGCAGG ACGTGTTCAA CTGGCGGAAG GAACTGGCTC AGTTCGAGGC TTACCGAGGG

GAGGCGTATA AGGATGCCGA TGGTTATAGT GTGGGCCTGG GCATTACCT GGGCAGTGGC

AATGCTGGGG CAGGTACTAC AGTCACGCCT GAGCAAGCCG CGCAGTGGTT CGCCGAGGAC

ACCGACCGCG CACTCGACCA GGGTGTGAGG TTGGCCGACG AGCTGGGCGT TACGAACAAT

GCCTCTATCC TGGGATTGGC CGGTATGGCC TTCCAGATGG GCGAAGGACG TGCCCGGCAG

TTCCGTAACA CCTTCCAGGC GATCAAGGAT CGCAACAAGG AAGCCTTCGA GGCTGGTGTG

CGAAACAGCA AGTGGTACAC GCAGACGCCC AACCGGGCCG AGGCATTCAT CAAGCGCATG

GCGCCCCACT TCGATACACC GAGTCAAATC GGTGTCGATT GGTACAGCGC GCAACAGCG

GAGTAA
```

Protein; Theoretical pI/Mw: 6.19/58620.92

SEQ ID NO: 16

```
MSNDNEVPGS MVIVAQGPDD QYAYEVPPID SAAVAGNMFG DLIQREIYLQ KNIYYPVRSI

FEQGTKEKKE INKKVSDQVD GLLKQITQGK REATRQERVD VMSAVLHKME SDLEGYKKTF

TKGPFIDYEK QSSLSIYEAW VKIWEKNSWE ERKKYPFQQL VRDELERAVA YYKQDSLSEA

VKVLRQELNK QKALKEKEDL SQLERDYRTR KANLEMKVQS ELDQAGSALP PLVSPTPEQW

LERATRLVTQ AIADKKQLQT TNNTLIKNSP TPLEKQKAIY NGELLVDEIA SLQARLVKLN

GGGGSGVALD RTRVDPQAVG NEVLKRNADK LNAMRGAEYG ANVKVSGTDI RMNGGNSAGM

LKQDVFNWRK ELAQFEAYRG EAYKDADGYS VGLGHYLGSG NAGAGTTVTP EQAAQWFAED

TDRALDQGVR LADELGVTNN ASILGLAGMA FQMGEGRARQ FRNTFQAIKD RNKEAFEAGV

RNSKWYTQTP NRAEAFIKRM APHFDTPSQI GVDWYSAATA E
```

P625: S5 TD-RD-Link-Phi29CD: 1365 bases

SEQ ID NO: 17

```
ATGTCCAATG ACAACGAAGT ACCTGGTTCC ATGGTTATTG TCGCACAAGG TCCAGACGAT

CAATACGCAT ACGAGGTTCC CCCTATCGAT AGCGCGGCCG TTGCCGGGAA TATGTTTGGC

GACTTAATTC AAAGAGAAAT ATATCTACAG AAAAACATTT ATTATCCAGT CCGATCTATT

TTTGAACAAG GAACAAAAGA AAAGAAGGAG ATCAACAAGA AAGTATCTGA TCAAGTCGAT
```

```
GGCTTGCTAA AGCAGATCAC TCAAGGAAAA AGGGAGGCCA CAAGGCAAGA GCGAGTCGAT
GTCATGTCGG CAGTCCTGCA CAAGATGGAA TCTGATCTTG AAGGATACAA AAAGACCTTT
ACCAAAGGCC CATTCATTGA CTACGAAAAG CAGTCAAGCC TCTCCATCTA TGAGGCCTGG
GTCAAGATCT GGGAGAAGAA CTCTTGGGAA GAAAGAAAGA AGTACCCTTT TCAGCAGCTT
GTTAGAGATG AACTGGAGCG GGCGGTTGCC TACTACAAAC AAGATTCACT CTCTGAAGCG
GTAAAAGTGC TAAGACAGGA GCTCAACAAG CAAAAAGCGC TAAAGGAAAA AGAGGACCTC
TCTCAACTGG AGCGGGACTA CAGAACCCGA AAGGCGAATC TCGAGATGAA AGTACAATCC
GAGCTTGATC AAGCGGGAAG TGCTTTGCCT CCATTGGTCA GTCCAACGCC AGAGCAATGG
CTTGAACGTG CCACAAGACT GGTTACGCAA GCAATTGCTG ATAAAAAGCA GCTGCAGACC
ACAAACAATA CTCTTATCAA GAATTCCCCA ACCCCTCTAG AAAAGCAGAA AGCCATCTAC
AATGGTGAGC TACTTGTGGA TGAGATAGCC AGTCTACAGG CCCGCTTAGT TAAGCTGAAC
ggaggaggag gatcaCAAAT TTCACAAGCG GGTATCAACT TAATTAAGAG CTTTGAGGGT
TTACAACTGA AAGCATATAA AGCTGTTCCG ACTGAGAAGC ATTACACCAT TGGTTACGGT
CATTACGGTT CCGATGTTTC ACCTAGGCAG GTTATCACTG CTAAACAGGC TGAAGACATG
TTGCGTGATG ATGTGCAGGC TTTTGTGGAT GGTGTAAATA AAGCATTAAA AGTATCTGTC
ACCCAAAATC AATTTGATGC ACTTGTCTCA TTCGCTTACA ACGTTGGGTT AGGGGCTTTC
AGGTCTTCTT CTCTACTGGA ATACTTGAAT GAAGGAAGAA CAGCTCTAGC GGCGGCTGAA
TTCCCTAAAT GGAATAAGTC AGGCGGTAAA GTTTATCAAG GGTTGATTAA CCGTAGAGCA
CAGGAGCAAG CCTTGTTTAA TAGTGGAACA CCTAAAAATG TTTAA
```

Protein; Theoretical pI/Mw: 8.71 QYAYEVPPID GLLKQITQGK/51160.99    SEQ ID NO: 18

```
MSNDNEVPGS MVIVAQGPDD QYAYEVPPID SAAVAGNMFG DLIQREIYLQ KNIYYPVRSI
FEQGTKEKKE INKKVSDQVD GLLKQITQGK REATRQERVD VMSAVLHKME SDLEGYKKTF
TKGPFIDYEK QSSLSIYEAW VKIWEKNSWE ERKKYPFQQL VRDELERAVA YYKQDSLSEA
VKVLRQELNK QKALKEKEDL SQLERDYRTR KANLEMKVQS ELDQAGSALP PLVSPTPEQW
LERATRLVTQ AIADKKQLQT TNNTLIKNSP TPLEKQKATY NGELLVDEIA SLQARLVKLN
GGGGSQISQA GINLIKSFEG LQLKAYKAVP TEKHYTIGYG HYGSDVSPRQ VITAKQAEDM
LRDDVQAFVD GVNKALKVSV TQNQFDALVS FAYNVGLGAF RSSSLLEYLN EGRTALAAAE
FPKWNKSGGK VYQGLINRRA QEQALFNSGT PKNV
```

P626: S5 TD-RD-Link-BP7e: 1422 bases    SEQ ID NO: 19

```
ATGTCCAATG CAACGAAGT ACCTGGTTCC ATGGTTATTG TCGCACAAGG TCCAGACGAT
CAATACGCAT ACGAGGTTCC CCCTATCGAT AGCGCGGCCG TTGCCGGGAA TATGTTTGGC
GACTTAATTC AAAGAGAAAT ATATCTACAG AAAAACATTT ATTATCCAGT CCGATCTATT
TTTGAACAAG GAACAAAAGA AAAGAAGGAG ATCAACAAGA AAGTATCTGA TCAAGTCGAT
GGCTTGCTAA AGCAGATCAC TCAAGGAAAA AGGGAGGCCA CAAGGCAAGA GCGAGTCGAT
GTCATGTCGG CAGTCCTGCA CAAGATGGAA TCTGATCTTG AAGGATACAA AAAGACCTTT
ACCAAAGGCC CATTCATTGA CTACGAAAAG CAGTCAAGCC TCTCCATCTA TGAGGCCTGG
GTCAAGATCT GGGAGAAGAA CTCTTGGGAA GAAAGAAAGA AGTACCCTTT TCAGCAGCTT
GTTAGAGATG AACTGGAGCG GGCGGTTGCC TACTACAAAC AAGATTCACT CTCTGAAGCG
GTAAAAGTGC TAAGACAGGA GCTCAACAAG CAAAAAGCGC TAAAGGAAAA AGAGGACCTC
TCTCAACTGG AGCGGGACTA CAGAACCCGA AAGGCGAATC TCGAGATGAA AGTACAATCC
GAGCTTGATC AAGCGGGAAG TGCTTTGCCT CCATTGGTCA GTCCAACGCC AGAGCAATGG
```

```
CTTGAACGTG CCACAAGACT GGTTACGCAA GCAATTGCTG ATAAAAAGCA GCTGCAGACC

ACAAACAATA CTCTTATCAA GAATTCCCCA ACCCCTCTAG AAAAGCAGAA AGCCATCTAC

AATGGTGAGC TACTTGTGGA TGAGATAGCC AGTCTACAGG CCCGCTTAGT TAAGCTGAAC ggaggaggag gatcaGGTGA CATTTTTGAT ATGCTGCGCC AAGACGAAGG CCTGGACCTG

AACCTGTATA AGACACGGA AGGCTACTGG ACGATTGGTA TTGGTCAGCT GGTCACCAAA

AACCCGAGTA AGATGTGGC ACGTGCTGAA CTGGACAAAC TGATGGGTCG TGTGTGCAAT

GGCCGCATTA CGATGGCGGA AGCCGAACAA CTGTTTAACC GTAGCGTTGA AAATGCACGT

CGCGCTATCC TGCGCAACCC GAAACTGAAA CCGGTGTATG ATGTTCTGGA CGAAGTGCGT

CGCTGTGCGC TGATCAACAT GGTTTTTCAG ATGGGCGAAG CGGGTGTCGC CGGCTTCACC

AATAGCCTGC GTATGCTGCA GCAAAAACGC TGGAACGATG CGGCCGTCAA TCTGGCACAG

TCTCGCTGGT ACAAACAAAC GCCGAATCGT GCGAAACGCG TTATTGCTAC CTTCAAAACG

GGCACCTGGG CGGCGTATCG TTGA

Protein; Theoretical pI/Mw: 9.05/53373.88
                                                                    SEQ ID NO: 20
MSNDNEVPGS MVIVAQGPDD QYAYEVPPID SAAVAGNMFG DLIQREIYLQ KNIYYPVRSI

FEQGTKEKKE INKKVSDQVD GLLKQITQGK REATRQERVD VMSAVLHKME SDLEGYKKTF

TKGPFIDYEK QSSLSIYEAW VKIWEKNSWE ERKKYPFQQL VRDELERAVA YYKQDSLSEA

VKVLRQELNK QKALKEKEDL SQLERDYRTR KANLEMKVQS ELDQAGSALP PLVSPTPEQW

LERATRLVTQ AIADKKQLQT TNNTLIKNSP TPLEKQKATY NGELLVDEIA SLQARLVKLN

GGGGSGDIFD MLRQDEGLDL NLYKDTEGYW TIGIGQLVTK NPSKDVARAE LDKLMGRVCN

GRITMAEAEQ LFNRSVENAR RAILRNPKLK PVYDVLDEVR RCALINMVFQ MGEAGVAGFT

NSLRMLQQKR WNDAAVNLAQ SRWYKQTPNR AKRVIATFKT GTWAAYR

P638: S5 Pyocin with 6X-His tag: 1497 bases
                                                                    SEQ ID NO: 21
ATGTCCAATG CAACGAAGT ACCTGGTTCC ATGGTTATTG TCGCACAAGG TCCAGACGAT

CAATACGCAT ACGAGGTTCC CCCTATCGAT AGCGCGGCCG TTGCCGGGAA TATGTTTGGC

GACTTAATTC AAAGAGAAAT ATATCTACAG AAAAACATTT ATTATCCAGT CCGATCTATT

TTTGAACAAG GAACAAAAGA AAAGAAGGAG ATCAACAAGA AAGTATCTGA TCAAGTCGAT

GGCTTGCTAA AGCAGATCAC TCAAGGAAAA AGGGAGGCCA CAAGGCAAGA GCGAGTCGAT

GTCATGTCGG CAGTCCTGCA CAAGATGGAA TCTGATCTTG AAGGATACAA AAAGACCTTT

ACCAAAGGCC CATTCATTGA CTACGAAAAG CAGTCAAGCC TCTCCATCTA TGAGGCCTGG

GTCAAGATCT GGGAGAAGAA CTCTTGGGAA GAAAGAAAGA AGTACCCTTT TCAGCAGCTT

GTTAGAGATG AACTGGAGCG GGCGGTTGCC TACTACAAAC AAGATTCACT CTCTGAAGCG

GTAAAAGTGC TAAGACAGGA GCTCAACAAG CAAAAAGCGC TAAAGGAAAA AGAGGACCTC

TCTCAACTGG AGCGGGACTA CAGAACCCGA AAGGCGAATC TCGAGATGAA AGTACAATCC

GAGCTTGATC AAGCGGGAAG TGCTTTGCCT CCATTGGTCA GTCCAACGCC AGAGCAATGG

CTTGAACGTG CCACAAGACT GGTTACGCAA GCAATTGCTG ATAAAAAGCA GCTGCAGACC

ACAAACAATA CTCTTATCAA GAATTCCCCA ACCCCTCTAG AAAAGCAGAA AGCCATCTAC

AATGGTGAGC TACTTGTGGA TGAGATAGCC AGTCTACAGG CCCGCTTAGT TAAGCTGAAC

GCCGAAACGA CACGACGCAG GACAGAAGCA GAACGCAAGG CGGCCGAGGA ACAAGCGTTG

CAAGATGCTA TTAAATTTAC TGCCGACTTT TATAAGGAAG TAACTGAGAA ATTTGGCGCA

CGAACATCGG AGATGGCGCG CCAACTGGCC GAAGGCGCCA GGGGGAAAAA TATCAGGAGT
```

-continued

```
TCGGCGGAAG CAATCAAGTC GTTTGAAAAG CACAAGGATG CGTTAAATAA AAAACTTAGC

CTTAAAGATA GGCAAGCCAT TGCCAAAGCC TTTGATTCTC TAGACAAGCA GATGATGGCG

AAGAGCCTTG AGAAATTTAG CAAAGGCTTT GGAGTTGTAG GCAAAGCTAT TGACGCCGCC

AGCCTGTACC AAGAGTTCAA GATATCTACG GAAACCGGGG ACTGGAAACC ATTCTTTGTA

AAAATTGAAA CACTAGCTGC TGGTGCGGCC GCCAGTTGGC TTGTGGGTAT TGCATTTGCC

ACGGCAACAG CCACTCCTAT AGGCATTCTG GGGTTCGCAC TGGTAATGGC AGTTACCGGG

GCGATGATTG ACGAAGACCT TCTAGAAAAA GCAAACAATC TTGTAATATC CATTCACCAC

CACCACCACC ACTAA
```

Theoretical pI/Mw: 8.50/56075.04

SEQ ID NO: 22

```
MSNDNEVPGS MVIVAQGPDD QYAYEVPPID SAAVAGNMFG DLIQREIYLQ KNIYYPVRSI

FEQGTKEKKE INKKVSDQVD GLLKQITQGK REATRQERVD VMSAVLHKME SDLEGYKKTF

TKGPFIDYEK QSSLSIYEAW VKIWEKNSWE ERKKYPFQQL VRDELERAVA YYKQDSLSEA

VKVLRQELNK QKALKEKEDL SQLERDYRTR KANLEMKVQS ELDQAGSALP PLVSPTPEQW

LERATRLVTQ AIADKKQLQT TNNTLIKNSP TPLEKQKATY NGELLVDEIA SLQARLVKLN

AETTRRRTEA ERKAAEEQAL QDAIKFTADF YKEVTEKFGA RTSEMARQLA EGARGKNIRS

SAEAIKSFEK HKDALNKKLS LKDRQAIAKA FDSLDKQMMA KSLEKFSKGF GVVGKAIDAA

SLYQEFKIST ETGDWKPFFV KIETLAAGAA ASWLVGIAFA TATATPIGIL GFALVMAVTG

AMIDEDLLEK ANNLVISIHH HHHH
```

P652: S5 Pyocin without His tag: 1497 bases

SEQ ID NO: 23

```
ATGTCCAATG ACAACGAAGT ACCTGGTTCC ATGGTTATTG TCGCACAAGG TCCAGACGAT

CAATACGCAT ACGAGGTTCC CCCTATCGAT AGCGCGGCCG TTGCCGGGAA TATGTTTGGC

GACTTAATTC AAAGAGAAAT ATATCTACAG AAAAACATTT ATTATCCAGT CCGATCTATT

TTTGAACAAG GAACAAAAGA AAAGAAGGAG ATCAACAAGA AAGTATCTGA TCAAGTCGAT

GGCTTGCTAA AGCAGATCAC TCAAGGAAAA AGGGAGGCCA CAAGGCAAGA GCGAGTCGAT

GTCATGTCGG CAGTCCTGCA CAAGATGGAA TCTGATCTTG AAGGATACAA AAAGACCTTT

ACCAAAGGCC CATTCATTGA CTACGAAAAG CAGTCAAGCC TCTCCATCTA TGAGGCCTGG

GTCAAGATCT GGGAGAAGAA CTCTTGGGAA GAAAGAAAGA AGTACCCTTT TCAGCAGCTT

GTTAGAGATG AACTGGAGCG GGCGGTTGCC TACTACAAAC AAGATTCACT CTCTGAAGCG

GTAAAGTGC TAAGACAGGA GCTCAACAAG CAAAAAGCGC TAAAGGAAAA AGAGGACCTC

TCTCAACTGG AGCGGGACTA CAGAACCCGA AAGGCGAATC TCGAGATGAA AGTACAATCC

GAGCTTGATC AAGCGGGAAG TGCTTTGCCT CCATTGGTCA GTCCAACGCC AGAGCAATGG

CTTGAACGTG CCACAAGACT GGTTACGCAA GCAATTGCTG ATAAAAAGCA GCTGCAGACC

ACAAACAATA CTCTTATCAA GAATTCCCCA ACCCCTCTAG AAAAGCAGAA AGCCATCTAC

AATGGTGAGC TACTTGTGGA TGAGATAGCC AGTCTACAGG CCCGCTTAGT TAAGCTGAAC

GCCGAAACGA CACGACGCAG ACAGAAGCA GAACGCAAGG CGGCCGAGGA CAAGCGTTG

CAAGATGCTA TTAAATTTAC TGCCGACTTT TATAAGGAAG TAACTGAGAA ATTTGGCGCA

CGAACATCGG AGATGGCGCG CCAACTGGCC GAAGGCGCCA GGGGGAAAAA TATCAGGAGT

TCGGCGGAAG CAATCAAGTC GTTTGAAAAG CACAAGGATG CGTTAAATAA AAAACTTAGC

CTTAAAGATA GGCAAGCCAT TGCCAAAGCC TTTGATTCTC TAGACAAGCA GATGATGGCG

AAGAGCCTTG AGAAATTTAG CAAAGGCTTT GGAGTTGTAG GCAAAGCTAT TGACGCCGCC

AGCCTGTACC AAGAGTTCAA GATATCTACG GAAACCGGGG ACTGGAAACC ATTCTTTGTA
```

```
AAAATTGAAA CACTAGCTGC TGGTGCGGCC GCCAGTTGGC TTGTGGGTAT TGCATTTGCC

ACGGCAACAG CCACTCCTAT AGGCATTCTG GGGTTCGCAC TGGTAATGGC AGTTACCGGG

GCGATGATTG ACGAAGACCT TCTAGAAAAA GCAAACAATC TTGTAATATC CATTTAA
```

Theoretical pI/Mw: 8.50/56075.04

SEQ ID NO: 24

```
MSNDNEVPGS MVIVAQGPDD QYAYEVPPID SAAVAGNMFG DLIQREIYLQ KNIYYPVRSI

FEQGTKEKKE INKKVSDQVD GLLKQITQGK REATRQERVD VMSAVLHKME SDLEGYKKTF

TKGPFIDYEK QSSLSIYEAW VKIWEKNSWE ERKKYPFQQL VRDELERAVA YYKQDSLSEA

VKVLRQELNK QKALKEKEDL SQLERDYRTR KANLEMKVQS ELDQAGSALP PLVSPTPEQW

LERATRLVTQ AIADKKQLQT TNNTLIKNSP TPLEKQKAIY NGELLVDEIA SLQARLVKLN

AETTRRRTEA ERKAAEEQAL QDAIKFTADF YKEVTEKFGA RTSEMARQLA EGARGKNIRS

SAEAIKSFEK HKDALNKKLS LKDRQAIAKA FDSLDKQMMA KSLEKFSKGF GVVGKAIDAA

SLYQEFKIST ETGDWKPFFV KIETLAAGAA ASWLVGIAFA TATATPIGIL GFALVMAVTG

AMIDEDLLEK ANNLVISI
```

Fyu A BD- T4 lysozyme fusion:
DNA sequence:

SEQ ID NO: 25

```
ATGAGCGACA CGATGGTTGT GAATGGCAGC GGCGGCGTTC CGGCGTTCCT GTTTAGCGGC

AGCACCCTGA GCAGCTATCG TCCGAATTTC GAGGCGAACA GCATCACCAT TGCGCTGCCG

CACTATGTGG ACCTGCCGGG CCGTAGCAAC TTCAAGCTGA TGTATATCAT GGGTTTTCCG

ATTGACACCG AGATGGAAAA GGATAGCGAG TACAGCAACA AAATCCGTCA AGAAAGCAAG

ATTAGCAAAA CCGAGGGCAC CGTGAGCTAC GAACAGAAAA TCACCGTTGA GACCGGCCAA

GAAAAGGATG GTGTGAAAGT TTATCGTGTG ATGGTTCTGG AGGGCACCAT CGCGGAGAGC

ATTGAACACC TGGACAAGAA AGAGAACGAA GACATCCTGA ACAACAACCG TAACCGTATT

GTGCTGGCGG ACAACACCGT TATCAACTTC GATAACATTA GCCAGCTGAA GGAATTTCTG

CGTCGTAGCG TGAACATCGT TATTTTCGAG ATGCTGCGTA TCGACGAACG TCTGCGTCTG

AAGATTTATA AAGATACCGA GGGCTACTAT ACCATCGGTA TTGGCCACCT GCTGACCAAA

AGCCCGAGCC TGAACGCGGC GAAGAGCGAA CTGGACAAAG CGATCGGCCG TAACTGCAAC

GGTGTGATTA CCAAGGATGA GGCGGAAAAA CTGTTTAACC AGGACGTGGA TGCGGCGGTT

CGTGGTATCC TGCGTAACGC GAAGCTGAAA CCGGTGTACG ACAGCCTGGA TGCGGTTCGT

CGTTGCGCGC TGATTAACAT GGTGTTCCAA ATGGGCGAGA CCGGCGTTGC GGGTTTTACC

AACAGCCTGC GTATGCTGCA GCAAAAGCGT TGGGACGAAG CGGCGGTTAA CCTGGCGAAA

AGCATCTGGT ATAACCAGAC CCCGAACCGT GCGAAACGTG TGATTACCAC CTTCCGTACC

GGCACCTGGG ATGCGTATAA AAACCTGTAA
```

Amino acid sequence:

SEQ ID NO: 26

```
MSDTMVVNGS GGVPAFLFSG STLSSYRPNF EANSITIALP HYVDLPGRSN FKLMYIMGFP

IDTEMEKDSE YSNKIRQESK ISKTEGTVSY EQKITVETGQ EKDGVKVYRV MLEGTIAES

IEHLDKKENE DILNNNRNRI VLADNTVINF DNISQLKEFL RRSVNIVIFE MLRIDERLRL

KIYKDTEGYY TIGIGHLLTK SPSLNAAKSE LDKAIGRNCN GVITKDEAEK LFNQDVDAAV

RGILRNAKLK PVYDSLDAVR RCALINMVFQ MGETGVAGFT NSLRMLQQKR WDEAAVNLAK

SIWYNQTPNR AKRVITTFRT GTWDAYKNL
```

Theoretical pI/Mw: 8.62/37291.55 Fyu A BD-
GP36 fusion:
DNA sequence:

SEQ ID NO: 27

ATGAGCGACA CGATGGTTGT GAATGGCAGC GGCGGCGTTC CGGCGTTCCT GTTTAGCGGC

AGCACCCTGA GCAGCTATCG TCCGAATTTC GAGGCGAACA GCATCACCAT TGCGCTGCCG

CACTATGTGG ACCTGCCGGG CCGTAGCAAC TTCAAGCTGA TGTATATCAT GGGTTTTCCG

ATTGACACCG AGATGGAAAA GGATAGCGAG TACAGCAACA AAATCCGTCA AGAAAGCAAG

ATTAGCAAAA CCGAGGGCAC CGTGAGCTAC GAACAGAAAA TCACCGTTGA GACCGGCCAA

GAAAAGGATG GTGTGAAAGT TTATCGTGTG ATGGTTCTGG AGGGCACCAT CGCGGAGAGC

ATTGAACACC TGGACAAGAA AGAGAACGAA GACATCCTGA ACAACAACCG TAACCGTATT

GTGCTGGCGG ACAACACCGT TATCAACTTC GATAACATTA GCCAGCTGAA GGAATTTCTG

CGTCGTAGCG TGAACATCGT TGGTGTGGCC CTGGACCGCA CGCGGGTTGA TCCCCAGGCA

GTCGGCAACG AGGTGCTCAA GCGCAACGCG GATAAGCTGA ATGCGATGCG GGGCGCCGAG

TACGGTGCCA ACGTCAAGGT CAGCGGCACG GACATTCGCA TGAACGGGGG TAACAGTGCC

GGCATGCTGA AGCAGGACGT GTTCAACTGG CGGAAGGAAC TGGCTCAGTT CGAGGCTTAC

CGAGGGGAGG CGTATAAGGA TGCCGATGGT TATAGTGTGG GCCTGGGGCA TTACCTGGGC

AGTGGCAATG CTGGGGCAGG TACTACAGTC ACGCCTGAGC AAGCCGCGCA GTGGTTCGCC

GAGGACACCG ACCGCGCACT CGACCAGGGT GTGAGGTTGG CCGACGAGCT GGGCGTTACG

AACAATGCCT CTATCCTGGG ATTGGCCGGT ATGGCCTTCC AGATGGGCGA AGGACGTGCC

CGGCAGTTCC GTAACACCTT CCAGGCGATC AAGGATCGCA ACAAGGAAGC CTTCGAGGCT

GGTGTGCGAA ACAGCAAGTG GTACACGCAG ACGCCCAACC GGGCCGAGGC ATTCATCAAG

CGCATGGCGC CCCACTTCGA TACACCGAGT CAAATCGGTG TCGATTGGTA CAGCGCCGCA

ACAGCGGAGT GA

Amino acid sequence:

SEQ ID NO: 28

MSDTMVVNGS GGVPAFLFSG STLSSYRPNF EANSITIALP HYVDLPGRSN FKLMYIMGFP

IDTEMEKDSE YSNKIRQESK ISKTEGTVSY EQKITVETGQ EKDGVKVYRV MVLEGTIAES

IEHLDKKENE DILNNNRNRI VLADNTVINF DNISQLKEFL RRSVNIVGVA LDRTRVDPQA

VGNEVLKRNA DKLNAMRGAE YGANVKVSGT DIRMNGGNSA GMLKQDVFNW RKELAQFEAY

RGEAYKDADG YSVGLGHYLG SGNAGAGTTV TPEQAAQWFA EDTDRALDQG VRLADELGVT

NNASILGLAG MAFQMGEGRA RQFRNTFQAI KDRNKEAFEA GVRNSKWYTQ TPNRAEAFIK

RMAPHFDTPS QIGVDWYSAA TAE

Theoretical pI/Mw: 5.51/42394.38
pelB-FyuA receptor: 2028 bases

SEQ ID NO: 29

ATGAAATACC TGCTGCCGAC CGCTGCTGCT GGTCTGCTGC TCCTCGCTGC CCAGCCGGCG

ATGGCCATGG CCAGACTTC ACAGCAAGAC GAAAGCACGC TGGTGGTTAC CGCCAGTAAA

CAATCTTCCC GCTCGGCATC AGCCAACAAC GTCTCGTCTA CTGTTGTCAG CGCGCCGGAA

TTAAGCGACG CCGGCGTCAC CGCCAGCGAC AAACTCCCCA GAGTCTTGCC CGGGCTCAAT

ATTGAAAATA GCGGCAACAT GCTTTTTTCG ACGATCTCGC TACGCGGCGT CTCTTCAGCG

CAGGACTTCT ATAACCCCGC CGTCACCCTG TATGTCGATG GCGTCCCTCA GCTTTCCACC

AACACCATCC AGGCGCTTAC CGATGTGCAA AGCGTGGAGT TGCTGCGAGG CCCACAGGGA

ACGTTATATG GCAAAAGCGC TCAGGGCGGG ATCATCAACA TCGTCACCCA GCAGCCGGAC

AGCACGCCGC GCGGCTATAT TGAAGGCGGC GTCAGTAGCC GCGACAGTTA TCGAAGTAAG

-continued

```
TTCAACCTGA GCGGCCCCAT TCAGGATGGC CTGCTGTACG GCAGCGTCAC CCTGTTACGC

CAGGTTGATG ACGGCGACAT GATTAACCCC GCGACGGGAA GCGATGACTT AGGCGGCACC

CGCGCCAGCA TAGGGAATGT GAAACTGCGT CTGGCGCCGG ACGATCAGCC CTGGGAAATG

GGCTTTGCCG CCTCACGCGA ATGTACCCGC GCCACCCAGG ACGCCTATGT GGGATGGAAT

GATATTAAGG GCCGTAAGCT GTCGATCAGC GATGGTTCAC CAGACCCGTA CATGCGGCGC

TGCACTGACA GCCAGACCCT GAGTGGGAAA TACACCACCG ATGACTGGGT TTTCAACCTG

ATCAGCGCCT GGCAGCAGCA GCATTATTCG CGCACCTTCC CTTCCGGTTC GTTAATCGTC

AATATGCCTC AGCGCTGGAA TCAGGATGTG CAGGAGCTGC GCGCCGCAAC CCTGGGCGAT

GCGCGTACCG TTGATATGGT GTTTGGGCTG TACCGGCAGA ACACCCGCGA AGTTAAAT

TCAGCCTACG ACATGCCGAC AATGCCTTAT TTAAGCAGTA CCGGCTATAC CACCGCTGAA

ACGCTGGCCG CATACAGTGA CCTGACCTGG CATTTAACCG ATCGTTTTGA TATCGGCGGC

GGCGTGCGCT TCTCGCATGA TAAATCCAGT ACACAATATC ACGGCAGCAT GCTCGGCAAC

CCGTTTGGCG ACCAGGGTAA GAGCAATGAC GATCAGGTGC TCGGGCAGCT ATCCGCAGGC

TATATGCTGA CCGATGACTG GAGAGTGTAT ACCCGTGTAG CCCAGGGATA TAAACCTTCC

GGGTACAACA TCGTGCCTAC TGCGGGTCTT GATGCCAAAC CGTTCGTCGC CGAGAAATCC

ATCAACTATG AACTTGGCAC CCGCTACGAA ACCGCTGACG TCACGCTGCA AGCCGCGACG

TTTTATACCC ACACCAAAGA CATGCAGCTT TACTCTGGCC CGGTCGGGAT GCAGACATTA

AGCAATGCGG GTAAAGCCGA CGCCACCGGC GTTGAGCTTG AAGCGAAGTG GCGGTTTGCG

CCAGGCTGGT CATGGGATAT CAATGGCAAC GTGATCCGTT CCGAATTCAC CAATGACAGT

GAGTTGTATC ACGGTAACCG GGTGCCGTTC GTACCACGTT ATGGCGCGGG AAGCAGCGTG

AACGGTGTGA TTGATACGCG CTATGGCGCA CTGATGCCCC GACTGGCGGT TAATCTGGTC

GGGCCGCATT ATTTCGATGG CGACAACCAG TTGCGGCAAG GCACCTATGC CACCCTGGAC

AGCAGCCTGG GCTGGCAGGC AACGGCAGCA GCGCCGTCGC GCAGGTCAAT ATGGGTCGCA

CCGTCGGTAT CAATACGCGA ATTGATTTCT TCTGA
```

Theoretical pI/Mw: 5.35/73772.10

SEQ ID NO: 30

```
MKYLLPTAAA GLLLLAAQPA MAMGQTSQQD ESTLVVTASK QSSRSASANN VSSTVVSAPE

LSDAGVTASD KLPRVLPGLN IENSGNMLFS TISLRGVSSA QDFYNPAVTL YVDGVPQLST

NTIQALTDVQ SVELLRGPQG TLYGKSAQGG IINIVTQQPD STPRGYIEGG VSSRDSYRSK

FNLSGPIQDG LLYGSVTLLR QVDDGDMINP ATGSDDLGGT RASIGNVKLR LAPDDQPWEM

GFAASRECTR ATQDAYVGWN DIKGRKLSIS DGSPDPYMRR CTDSQTLSGK YTTDDWVFNL

ISAWQQQHYS RTFPSGSLIV NMPQRWNQDV QELRAATLGD ARTVDMVFGL YRQNTREKLN

SAYDMPTMPY LSSTGYTTAE TLAAYSDLTW HLTDRFDIGG GVRFSHDKSS TQYHGSMLGN

PFGDQGKSND DQVLGQLSAG YMLTDDWRVY TRVAQGYKPS GYNIVPTAGL DAKPFVAEKS

INYELGTRYE TADVTLQAAT FYTHTKDMQL YSGPVGMQTL SNAGKADATG VELEAKWRFA

PGWSWDINGN VIRSEFTNDS ELYHGNRVPF VPRYGAGSSV NGVIDTRYGA LMPRLAVNLV

GPHYFDGDNQ LRQGTYATLD SSLGWQATER MNISVYVDNL FDRRYRTYGY MNGSSAVAQV

NMGRTVGINT RIDFF
```

We claim:

1. A method of killing *Klebsiella pneumoniae* or *Escherichia coli*, comprising contacting the *K pneumoniae* or *E. coli* with a bacteriocin that comprises:
   a) a receptor-mediated translocation domain comprising the amino acid sequence set forth in the 1-320 segment of SEQ ID NO:10;
   b) a receptor binding domain comprising the amino acid sequence set forth in the 322-457 segment of SEQ ID NO:10; and
   c) a cargo domain comprising the amino acid sequence set forth in the 475-559 segment of SEQ ID NO:10.

2. The method of claim 1, wherein the bacteriocin comprises:
   a) a receptor-mediated translocation domain comprising the amino acid sequence set forth in the 1-320 segment of SEQ ID NO:10;
   b) a receptor binding domain comprising the amino acid sequence set forth in the 322-457 segment of SEQ ID NO:10;
   c) a cargo domain comprising the amino acid sequence set forth in the 475-559 segment of SEQ ID NO:10; and
   d) a peptide linker connecting a) and b) or connecting b) and c), having an amino acid sequence different from the corresponding segment of SEQ ID NO:10 at the corresponding location.

3. The method of claim 1, wherein the bacteriocin comprises:
   a) a receptor-mediated translocation domain comprising the amino acid sequence of the 1-320 segment of SEQ ID NO:10;
   b) a receptor binding domain comprising the amino acid sequence of the 322-457 segment of SEQ ID NO:10;
   c) a cargo domain comprising the amino acid sequence of the 475-559 segment of SEQ ID NO:10; and
   d) a purification tag.

4. The method of claim 1, wherein the bacteriocin comprises the amino acid sequence of SEQ ID NO:10.

5. The method of claim 1, wherein the bacteriocin consists of the amino acid sequence of SEQ ID NO:10.

6. The method of claim 1, further comprising contacting the *K. pneumoniae* or *E. coli* with another antimicrobial, antibiotic, or other therapeutic agent.

7. The method of claim 1, further comprising contacting the *K. pneumoniae* in the presence of *Pseudomonas aeruginosa* with a pyocin.

8. The method of claim 7, wherein the pyocin is an S-type pyocin.

9. The method of claim 8, wherein the S-type pyocin is S5 pyocin.

10. The method of claim 1, wherein the *K. pneumoniae* or *E. coli* is drug-resistant *K. pneumoniae* or *E. coli*.

* * * * *